United States Patent
Matthiesen et al.

(10) Patent No.: US 9,297,035 B2
(45) Date of Patent: Mar. 29, 2016

(54) COMPOSITIONS AND METHODS FOR DETECTION OF CHROMOSOMAL ABERRATIONS WITH NOVEL HYBRIDIZATION BUFFERS

(75) Inventors: Steen Hauge Matthiesen, Hillerod (DK); Kenneth H. Petersen, Smorum (DK); Tim Svenstrup Poulsen, Horsholm (DK)

(73) Assignee: DAKO Denmark A/S, Glostrup (DK)

( * ) Notice: Subject to any disclaimer, the term of this patent is extended or adjusted under 35 U.S.C. 154(b) by 490 days.

(21) Appl. No.: 12/994,495

(22) PCT Filed: May 27, 2009

(86) PCT No.: PCT/IB2009/006548
§ 371 (c)(1),
(2), (4) Date: May 23, 2011

(87) PCT Pub. No.: WO2009/147537
PCT Pub. Date: Dec. 10, 2009

(65) Prior Publication Data
US 2011/0281263 A1    Nov. 17, 2011

Related U.S. Application Data

(60) Provisional application No. 61/056,089, filed on May 27, 2008, provisional application No. 61/155,683, filed on Feb. 26, 2009.

(30) Foreign Application Priority Data

May 27, 2008  (DK) ................................ 2008 00727
Feb. 27, 2009  (DK) ................................ 2009 00278

(51) Int. Cl.
C12Q 1/68    (2006.01)

(52) U.S. Cl.
CPC ............ C12Q 1/6832 (2013.01); C12Q 1/6841 (2013.01); *Y10T 436/143333* (2015.01)

(58) Field of Classification Search
CPC .... C12Q 1/6813; C12Q 1/6841; C07H 21/00; C07H 21/02; C07H 21/04
USPC ................................. 435/6.1; 536/23.1, 24.3
See application file for complete search history.

(56) References Cited

U.S. PATENT DOCUMENTS

| | | |
|---|---|---|
| 4,886,741 A | 12/1989 | Schwartz |
| 4,888,278 A | 12/1989 | Singer et al. |
| 4,996,359 A | 2/1991 | Kesling, Jr. et al. |
| 5,106,730 A * | 4/1992 | Van Ness et al. ............ 435/6.12 |
| 5,382,285 A | 1/1995 | Morrison |
| 5,521,061 A | 5/1996 | Bresser et al. |
| 5,525,492 A | 6/1996 | Hill |
| 5,527,675 A | 6/1996 | Coull et al. |
| 5,539,082 A | 7/1996 | Nielsen et al. |
| 5,582,985 A | 12/1996 | Thompson |
| 5,623,049 A | 4/1997 | Lobberding et al. |
| 5,633,129 A | 5/1997 | Karger et al. |
| 5,705,333 A | 1/1998 | Shah et al. |
| 5,714,331 A | 2/1998 | Buchardt et al. |
| 5,718,915 A | 2/1998 | Virtanen et al. |
| 5,736,336 A | 4/1998 | Buchardt et al. |
| 5,750,340 A * | 5/1998 | Kim et al. ..................... 435/6.13 |
| 5,766,855 A | 6/1998 | Buchardt et al. |
| 5,773,571 A | 6/1998 | Nielsen et al. |
| 5,786,461 A | 7/1998 | Buchardt et al. |
| 5,837,459 A | 11/1998 | Berg et al. |
| 5,856,089 A * | 1/1999 | Wang et al. .................. 435/6.16 |
| 5,869,237 A | 2/1999 | Ward et al. |
| 5,891,625 A | 4/1999 | Buchardt et al. |
| 5,925,744 A | 7/1999 | Haner et al. |
| 5,972,610 A | 10/1999 | Buchardt et al. |
| 5,986,053 A | 11/1999 | Ecker et al. |
| 6,107,470 A | 8/2000 | Nielsen et al. |
| 6,201,103 B1 | 3/2001 | Nielsen et al. |
| 6,228,982 B1 | 5/2001 | Norden et al. |
| 6,331,618 B1 | 12/2001 | Bloch et al. |
| 6,357,163 B1 | 3/2002 | Buchardt et al. |
| 6,475,720 B1 | 11/2002 | Gray et al. |
| 6,555,670 B1 | 4/2003 | Aizawa et al. |
| 6,656,685 B2 | 12/2003 | Utermohlen et al. |
| 6,670,461 B1 | 12/2003 | Wengel et al. |
| 6,794,499 B2 | 9/2004 | Wengel et al. |
| 7,034,133 B2 | 4/2006 | Wengel et al. |
| 7,374,945 B2 | 5/2008 | Becker |

(Continued)

FOREIGN PATENT DOCUMENTS

| EP | 1013772 | 6/2000 |
|---|---|---|
| WO | WO 91/02088 | 2/1991 |

(Continued)

OTHER PUBLICATIONS 2-pyrrolidone, Wikapedia Nov. 1, 2012.*
Olsen et al.,Amplification of HER2 and TOP2A and deletion of TOP2A genes in breast cancer investigated by new FISH probes. Acta Oncologia 43(1) : 35 (2004).*
Shapiro et al. Detection of N-myc gene amplification by fluorescence in situ hybridization. American Journal of Pathology 142 (5) : 1339 (1993).*
Tkachuk et al. Detection of bcr-abl fusion in Chronic Myelogenous Leukemia by in situ hybridization. Science 250 :559 (1990).*
Woenckhaus et al., Multitarget FISH and LOH analyses at chromosome 3p in non-small cell lung cancer and adjacent bronchial epithelium. Am. J. of Clin. Pathol. 123 :752 (2005).*
The Stratagene Catalog p. 39 (1988).*

(Continued)

*Primary Examiner* — Ethan C Whisenant

(57) ABSTRACT

The present invention provides compositions and methods for the detection of nucleic acid sequences associated with chromosomal aberrations. The invention may, for example, eliminate the use of or reduce the dependence on formamide in hybridization. Compositions for use in the invention include an aqueous composition comprising at least one nucleic acid sequence and at least one polar aprotic solvent in an amount effective to denature double-stranded nucleotide sequences.

52 Claims, 2 Drawing Sheets

(56) References Cited

U.S. PATENT DOCUMENTS

| | | |
|---|---|---|
| 7,572,582 B2 | 8/2009 | Wengel et al. |
| 7,750,208 B2 | 7/2010 | Huang et al. |
| 7,867,443 B2 | 1/2011 | Key et al. |
| 8,034,909 B2 | 10/2011 | Wengel et al. |
| 8,080,644 B2 | 12/2011 | Wengel et al. |
| 8,153,365 B2 | 4/2012 | Wengel et al. |
| 2001/0000487 A1 | 4/2001 | Essenfeld et al. |
| 2001/0007748 A1 | 7/2001 | An et al. |
| 2001/0009766 A1 | 7/2001 | Bard et al. |
| 2001/0010936 A1 | 8/2001 | Richards et al. |
| 2001/0011131 A1 | 8/2001 | Luyten et al. |
| 2001/0018512 A1* | 8/2001 | Blanchard ............... 536/25.3 |
| 2001/0026919 A1 | 10/2001 | Chenchik et al. |
| 2001/0027567 A1 | 10/2001 | Federoff |
| 2001/0056203 A1 | 12/2001 | Sezi et al. |
| 2002/0150904 A1 | 10/2002 | Bi et al. |
| 2002/0164614 A1* | 11/2002 | Becker ...................... 435/6 |
| 2002/0182613 A1 | 12/2002 | Mirkin et al. |
| 2002/0197629 A1 | 12/2002 | Gjerde |
| 2002/0198366 A1 | 12/2002 | Ashkenazi et al. |
| 2003/0108903 A1 | 6/2003 | Wang et al. |
| 2003/0175852 A1 | 9/2003 | Kalra et al. |
| 2004/0029184 A1 | 2/2004 | Gourevitch |
| 2004/0030093 A1 | 2/2004 | Sakurai et al. |
| 2004/0048376 A1 | 3/2004 | Chabot et al. |
| 2004/0053222 A1 | 3/2004 | Storhoff et al. |
| 2004/0096967 A1 | 5/2004 | Gryseels et al. |
| 2004/0210967 A1 | 10/2004 | Chen et al. |
| 2005/0014154 A1 | 1/2005 | Weizenegger |
| 2005/0191657 A1 | 9/2005 | Demorest et al. |
| 2005/0266459 A1 | 12/2005 | Poulsen et al. |
| 2006/0030541 A1 | 2/2006 | Garcia et al. |
| 2006/0147957 A1 | 7/2006 | Qian et al. |
| 2007/0148657 A1 | 6/2007 | Myerson et al. |
| 2007/0243545 A1* | 10/2007 | Kilpatrick et al. ................ 435/6 |
| 2008/0044385 A1 | 2/2008 | Nishi et al. |
| 2008/0227653 A1 | 9/2008 | Fodor et al. |
| 2009/0123913 A1 | 5/2009 | Barany et al. |
| 2009/0197346 A1* | 8/2009 | Winkler et al. ............... 436/176 |
| 2009/0221429 A1* | 9/2009 | Fujimoto et al. .................. 506/4 |
| 2009/0294305 A1* | 12/2009 | Bekki et al. ................... 205/792 |
| 2011/0250698 A1* | 10/2011 | Pollner et al. ................... 436/94 |
| 2011/0262930 A1 | 10/2011 | Deleersnijder et al. |
| 2011/0281263 A1 | 11/2011 | Matthiesen et al. |
| 2012/0331587 A1 | 12/2012 | Lassen et al. |
| 2013/0017176 A1 | 1/2013 | Hosoda et al. |
| 2013/0156695 A1 | 6/2013 | Sprecher et al. |
| 2013/0230918 A1 | 9/2013 | Wakamiya |

FOREIGN PATENT DOCUMENTS

| | | |
|---|---|---|
| WO | WO92/07956 | 5/1992 |
| WO | WO 92/07959 | 5/1992 |
| WO | WO 94/02638 | 2/1994 |
| WO | WO94/02639 | 2/1994 |
| WO | WO 94/02639 | 2/1994 |
| WO | WO 96/04000 | 2/1996 |
| WO | WO 99/14226 | 6/1999 |
| WO | WO 00/69899 | 11/2000 |
| WO | WO 01/66804 | 9/2001 |
| WO | WO 02/061137 | 8/2002 |
| WO | WO 03/014398 | 2/2003 |
| WO | WO 03/027328 | 4/2003 |
| WO | WO 03/054209 | 7/2003 |
| WO | WO 2006/007841 | 1/2006 |
| WO | WO 2006/066039 | 6/2006 |
| WO | WO 2006/117596 | 11/2006 |
| WO | WO 2007/058326 | 11/2006 |
| WO | WO 2007/019492 A2 | 2/2007 |
| WO | WO 2007/037341 A1 | 4/2007 |
| WO | WO2007/058326 * | 5/2007 |
| WO | WO 2007/109941 | 9/2007 |
| WO | WO 2009/074154 | 6/2009 |
| WO | WO 2009/144581 | 12/2009 |
| WO | WO 2009/147537 | 12/2009 |

OTHER PUBLICATIONS

Moroni et al., Gene copy number for epidermal growth factor receptor (EGFR) and clinical response to antiEGFR treatment in colorectal cancer: a cohort study. Lancet Oncology 6:279 (2005).*

Moroni et al. Gene copy number for epidermal growth factor receptor (EGFR) and clinical response to antiEGFR treatment in colorectal cancer: a cohort study. [Lancet Oncology 6 : 279 (2005)].*

Summersgill et al.Fluorescence and chromogenic in situ hybridization to detect genetic aberrations in formalin-fixed paraffin embedded material, including tissue microarrays. [Nature Protocols 3 (2) : 220 (Jan. 2008)] cited/provided in related U.S. Appl. No. 13/203,160.*

International Search Report for PCT/IB2009/005893, mailed Sep. 22, 2009.

International Search Report for PCT/IB2009/006548, mailed Feb. 15, 2010.

International Search Report for PCT/IB2009/007725, mailed May 7, 2010.

International Search Report for PCT/IB2009/007917, mailed Apr. 28, 2010.

International Search Report for PCT/IB2010/000659, mailed Jul. 12, 2010.

Boehringer Mannheim Biochemicals Catalog, "Nucleic Acid Hybridization—General Aspects," pp. 14-17, Jan. 1, 1992.

Chakrabarti R. et al., "The enhancement of PCR amplification by low molecular-weight sulfones," Gene, 274:293-98 (2001).

Chakrabarti R. et al., "The enhancement of PCR amplification by low molecular weight amides," Nucleic Acids Research, 29(11):2377-81 (2001).

Chardonnet Y. et al., "Human papillomavirus detection in cervical cells by in situ hybridization with biotinylated probes," Cytopathology, 3(6):341-50 (1992).

DAKO Catalog, "TOP2A Fish pharmDxTM Kit," pp. 1-33, May 24, 2007.

Luo H. et al., "Establishment of a simple and useful way for preimplantation genetic diagnosis of chromosomal diseases," Journal of Huazhong University of Science and Technology, 27(3):315-17 (2007).

Mochizuki S. et al., "Solvent effect on PCR from a viewpoint of a change of microscopic environment of Mg(2+) in a solution," Biochem Biophys Res Commun., Jun. 6, 2007 (Abstract only).

Nielsen K.V. et al., "PNA suppression method combined with fluorescence in situ hybridisation (FISH) technique," Chapter 10 in PRINS and PNA Technologies in Chromosomal Investigation (Ed. Franck Pellestor), 2006.

Olsen K.E. et al., "Amplification of HER2 and TOP2A and deletion of TOP2A genes in breast cancer investigated by new FISH probes," Acta Oncologica, 43(1):34-42 (2004).

Extended European Search Report from the European Patent Office for corresponding EP Application No. 13164099.7, Aug. 14, 2013 (5 pages).

Extended European Search Report from the European Patent Office for corresponding EP Application No. 13164094.8, Aug. 8, 2013 (5 pages).

Brown et al., Analysis of RNA by Northern and Slot Blot Hybridization, Current Protocols in Molecular Biology, Unit 4.9 (19 pages).

Markarian et al., "Effect of Diethylsulfoxide on the Thermal Denaturation of DNA," Department of Chemistry, Yerevan State University, Armenia, Jan. 19, 2006 (5 pages).

Office Action, issued Oct. 4, 2013, in U.S. Appl. No. 13/203,149 (19 pages).

Office Action, issued Sep. 18, 2013, in U.S. Appl. No. 13/203,137 (33 pages).

Office Action, issued Sep. 24, 2013, in U.S. Appl. No. 13/203,160 (31 pages).

Superscript™ First-Strand Synthesis System for RT-PCR, Invitrogen document dated Mar. 5, 2007 (4 pages).

Beebe, "Glycerin Antigen Retrieval," Microscopy Today, 9:30-31, 1999 (3 pages).

DOW Ethylene Glycols, Webpage, Jun. 28, 2012 (2 pages).

(56) References Cited

OTHER PUBLICATIONS

DOW Propylene Glycol, Webpage, Jun. 28, 2012 (2 pages).
Hayat, editor, "Factors Affecting Antigen Retrieval," Chapter 4 of Microscopy, Immunohistochemistry and Antigen Retrieval, New York, p. 71-93, 2002 (23 pages).
International Search Report issued Jun. 16, 2008 for International Application No. PCT/DK2008/000066 (3 pages).
Kurreck, "Improvement through novel chemical modifications," *Eur. J. Biochem.*, 270:1628-1644, 2003 (17 pages).
LyondellBassell, Webpage, Mar. 7. 2013 (1 page).
Notice of Allowance, Examiner-Initiated Interview Summary, and Reasons for Allowability, issued Feb. 20, 2013, in U.S. Appl. No. 12/526,323, filed Feb. 16, 2010 (10 pages).
Office Action, issued Jul. 17, 2012, in U.S. Appl. No. 12/526,323, filed Feb. 16, 2010 (16 pages).
Office Action issued Mar. 18, 2013, in U.S. Appl. No. 13/203,149, filed Aug. 24, 2011 (16 pages).
Optim synthetic Glycerine—Vapor Pressure and Boiling Point, Webpage, Jun. 28, 2012 (1 page).
Powell et al., "Metallographic in situ hybridization," *Human Pathol.*, 38:1145-1159, 2007 (15 pages).
Wahl, G. et al., "Efficient transfer of large DNA fragments from agarose gels to diazobenzyloxymethyl-paper and rapid hybridization by using dextran sulfate," *Proc. Natl. Acad. Sci.*, Aug. 1979, pp. 3683-3687, vol. 7, No. 8 (5 pages).
Kiyama, Hiroshi et al., "*In Situ Hybridization Method*," New Genetic Engineering Handbook, Experimental Medical Edition, Muramatsu Masami, et al. Editors, pp. 202-203, Apr. 20, 1996.
Toyozo, Takahashi, "*Principal Assay Method in Infection Diagnosis, Chapter 3. Diagnosis of infection by DNA Probe*," Applied DNA Probe Technology, pp. 36-39, Feb. 5, 1998
"*20X SSC Recipe*," Bioprotocols.info (retrieved on Jul. 28, 2014 from the internet: https://www.bioprotocols.info./reagent_and_buffer_recipes/20x-SSC.php) (1 page).
Ahern, Holly, "*Biochemical, reagents kits offer scientists good return on investment*," The Scientist, 9(15):20 (Jul. 24, 1995).
Cox, W., et al., "*Fluorescent DNA hybridization probe preparation using amine modification and reactive dye coupling*," Biotechniques, 36:114-122 (Jan. 2004).

Huber C. and Berti G., "*Detection of Partial Denaturation in AT-Rich DNA Fragments by Ion-Pair Reserved-Phase Chromatography*," Anal. Chem., 68(17):2959 (Sep. 1, 1996).
Rigby S. et al., "*Fluorescence In Situ Hybridization with Peptide Nucleic Acid Probes for Rapid Identifications of Candida albicans Directly from Blood Culture Bottles*," Journal of Clinical Microbiology, 4(6): 2182 (Jun. 2002).
Summersgill B. et al., "*Fluorescence and Chromogenic in situ hybridization to detect genetic aberrations in formalin-fixed paraffin embedded material, including tissue microarrays*," Natural Protocols, 3(2): 220 (Feb. 2008).
Xi C. et al., "*Use of DNA and Peptide Nucleic Acid Molecular Beacons for Detection and Quantification of rRNA in Solution and in Whole Cells*," Applied and Environmental Microbiology, 69(9): 5673 (Sep. 2003).
Office Action for U.S. Appl. No. 13/203,160 dated Jun. 25, 2014 (24 pages).
Office Action for U.S. Appl. No. 12/994,492 dated May 7, 2014 (7 pages).
Office Action for U.S. Appl. No. 13/203,137 dated Jun. 10, 2014 (20 pages).
Office Action for U.S. Appl. No. 13/203,149 dated Jul. 30, 2014 (31 pages).
Office Action for U.S. Appl. No. 13/513,164 dated Aug. 22, 2014 (51 pages).
European Office Action for Application No. 13 164 094.8, dated Dec. 19, 2014.
European Office Action for Application No. 13 164 099.7, dated Dec. 19, 2014.
Susan Rigby et al, "Fluorescence in Situ Hybridization with Peptide Nucleic Acid Probes for Rapid Identification of Candida albicans Directly from Blood Culture Bottles," Journal of Clinical Microbiology, vol. 40, No. 6, Mar. 26, 2002, pp. 2182-2186.
Office Action dated Apr. 28, 2015 from the Chinese Intellectual Property Office for Appl. No. 200980119333.3.
Office Action dated May 5, 2015 from the Federal Service for Intellectual Property (Russian Federation) for Appl. No. 2010151495/10(074408).

* cited by examiner

COMPOSITIONS AND METHODS FOR DETECTION OF CHROMOSOMAL ABERRATIONS WITH NOVEL HYBRIDIZATION BUFFERS

This application is a U.S. National Phase Application under 35 U.S.C. §371 of PCT/IB2009/006548, filed May 27, 2009, which claims priority to U.S. Provisional Application No. 61/056,089, filed May 27, 2008, U.S. Provisional Application No. 61/155,683, filed Feb. 26, 2009, Danish Application No. PA 2008 00727, filed May 27, 2008, and Danish Patent Application No. PA 2009 00278, filed Feb. 27, 2009, all of which are incorporated herein by reference in their entireties.

FIELD OF THE INVENTION

The present invention relates generally to compositions and methods for detecting chromosomal aberrations in vivo, in vitro, and in situ. The present invention further relates to compositions comprising molecular probes for the detection of particular nucleotide sequences (including normal sequences and those associated with chromosomal aberrations and/or infectious disease) and aqueous compositions comprising at least one polar aprotic solvent in an amount sufficient to denature double-stranded nucleotide sequence for use in hybridization, particularly for use in in situ hybridization (ISH).

In one embodiment, the present invention relates to molecular probes for use in, e.g., the fields of cytology, histology, and molecular biology, and to kits comprising such molecular probes. In other embodiments, the present invention relates to methods of detecting chromosomal aberrations or infectious disease using such molecular probes, methods of diagnosing a genetic defect or disease state using such molecular probes, and methods of providing a prognosis using such molecular probes.

BACKGROUND AND DESCRIPTION

Many pathological conditions, both congenital defects and acquired diseases, are associated with chromosomal aberrations such as amplifications, aneuploidy, potential breakpoints, insertions, inversions, deletions, duplications, rearrangements, and translocations. Moreover, pathogenic infections generally result in the presence of nucleic acid sequences of the infecting bacterium, virus, or fungus in the infected organism.

Establishing the presence or absence of a nucleotide sequence associated with a congenital defect, acquired disease, or infectious pathogen, through in vivo, in vitro, or in situ analysis of genomic DNA, chromosomes, chromosome fragments, or genes, can assist a clinician in reaching an appropriate diagnosis. For example, the expansion of a CGG trinucleotide repeat in the 5'UTR (UnTranslated Region) of mRNA of the fragile X mental retardation-1 (FMR1) gene allows the clinician to diagnose fragile X syndrome. This expansion leads to transcriptional silencing of the gene. However, other mechanisms, e.g. deletions of FMR1 and mutations, might also cause fragile X syndrome. The result, absence or reduced amounts of the gene product, FMRP, leading to the disease, is the same for both the expansion-caused silencing and for gene deletion. An example of a condition caused by a numerical anomaly is Down Syndrome, also known as Trisomy 21 (an individual with Down Syndrome has three copies of chromosome 21, rather than two). Turner Syndrome is an example of a monosomy where the individual is born with only one sex chromosome, an X. Other examples include Wolf-Hirschhorn syndrome, which is caused by partial deletion of the short arm of chromosome 4, and Jacobsen syndrome, also called the terminal 11 q deletion disorder. Some syndromes, such as Charcot-Marie-Tooth disease type 1A, may be caused by duplications, e.g., of the gene encoding peripheral myelin protein 22 (PMP22) on chromosome 17. In other syndromes, such as Robertsonian translocation, an entire chromosome has attached to another at the centromere. Robertsonian translocations may only occur with chromosomes 13, 14, 15, 21 and 22 and the progeny of a heterozygous carrier of a Robertsonian translocation might, e.g. inherit an unbalanced trisomy 21, causing Down Syndrome.

Establishing the presence or absence of a nucleotide sequence associated with a congenital defect, acquired disease, or infectious pathogen, through in vivo, in vitro, or in situ analysis of genomic DNA, chromosomes, chromosome fragments, or genes, can also be invaluable to the clinician in selecting an appropriate course of treatment where a disease state has been diagnosed. For example, a breast cancer patient in whom the HER2 gene has been amplified may benefit from treatment with Herceptin™ (trastuzumab), a monoclonal antibody that recognizes HER2 protein. In another example, a clinician may choose to prescribe Erbitux® (cetuximab) or Vectibix™ (panitumumab) (therapeutic monoclonal antibodies that specifically recognize epidermal growth factor receptor (EGFR)) to a colorectal cancer patient in whom the EGFR gene is amplified.

Establishing the presence or absence of a nucleotide sequence associated with a congenital defect, acquired disease, or infectious pathogen, through in vivo, in vitro, or in situ analysis of genomic DNA, chromosomes, chromosome fragments, or genes, can also assist a clinician in providing a prognosis. Thus, breast cancer patients in whom the TOP2A gene is amplified or deleted have a worse prognosis than those in whom it is not.

Detecting the presence or absence of a nucleotide sequence generally entails recognition of the sequence by hybridization, or stabilization of a nucleotide double helix structure by hydrogen bonding between bases on opposite strands (A+T or G+C). In a basic example of hybridization, nucleic acid fragments or sequences bind to a complementary nucleic acid fragment or sequence. Detection by hybridization generally involves the use of nucleic acid probes designed to bind to, or "hybridize" with, a nucleic acid target such as, e.g., a DNA or RNA sequence.

Well known techniques exist in the art of molecular biology for detecting chromosome aberrations. So far, however, a fast, convenient, cheap, and user-friendly test which allows for widespread and routine detection of chromosome aberrations has not been available.

The efficiency and accuracy of nucleic acid hybridization assays depend primarily on at least one of three factors: a) denaturation (i.e., separation of, e.g., two nucleic acid strands) conditions, b) renaturation (i.e., re-annealing of, e.g., two nucleic acid strands) conditions, and c) post-hybridization washing conditions.

Traditional hybridization experiments, such as ISH assays, use a formamide-containing buffer to denature doubled stranded nucleic acid chains. Formamide is a solvent that has a destabilizing effect on the helical state of, for example, DNA, RNA, and analogs thereof, by displacing loosely and uniformly bound hydrate molecules. Furthermore, formamide stabilizes the coil state of DNA, RNA, and analogs thereof by 'formamidation' of the Watson-Crick binding sites of the bases.

The denaturation step is followed by the re-annealing of two complementary strands of nucleic acid chains, which is by far the most time-consuming aspect of an assay using hybridization. For example, in a traditional fluorescence in situ hybridization (FISH) protocol, re-annealing takes 14-24 hours, and can even take up to 72 hours. Examples of traditional hybridization times are shown in FIGS. 1 and 2.

Until now it was believed that the use of chaotropic agents, such as formamide (other chaotropic agents include guanidinium hydrogen and urea), which interfere with the Watson-Crick binding sites of nucleic acid bases and thereby disturb the hydrogen bonds between complementary nucleic acid bases, was the only way to lower the melting temperature (Tm) of the complementary chains, as is necessary for the denaturation step. However, although the use of chaotropic agents lowers the Tm, these agents appear to significantly prolong the hybridization time, as compared to hybridization in an aqueous solution without a chaotropic agent.

Formamide has disadvantages beyond a long processing time. Formamide is a toxic, hazardous material, subject to strict regulations for use and waste. Furthermore, the use of a high concentration of formamide appears to incur morphological destruction of cellular, nuclear, and/or chromosomal structure.

The aqueous compositions described herein allow the detection of nucleic acid sequences under conditions that have several potential advantages over the prior art, such as faster hybridization times, lower hybridization temperatures, and less toxic hybridization compositions.

SUMMARY OF THE INVENTION

The present invention provides compositions and methods for the detection of nucleic acid sequences associated with chromosomal aberrations. The compositions and methods of the invention are applicable to any hybridization technique, and to any molecular system that hybridizes or binds using base pairing, such as, for example, DNA, RNA, PNA, LNA, and synthetic and natural analogs thereof. The compositions and methods of the invention allow for the highly sensitive, technically easy, flexible, reliable, and/or rapid detection of nucleic acid sequences associated with chromosomal aberrations. In one embodiment, the invention provides the ability to tailor the hybridization time by varying the temperature of the hybridization reaction to a much greater degree than is available using prior art methods. The hybridization compositions and methods of the invention preserve the morphology of a biological sample, provide a non-toxic hybridization composition and procedure, provide a low evaporation hybridization technique, reduce and/or remove the need for blocking of unspecific binding, and/or permit the use of heterogeneous probes without the need to block, remove, or otherwise disable the binding of, e.g., repetitive sequences in a biological sample.

In one embodiment, the invention provides a composition comprising a first molecular probe that detects a nucleotide sequence associated with a chromosomal aberration, and an aqueous composition comprising at least one polar aprotic solvent in an amount effective to denature double-stranded nucleotide sequences. In another embodiment, the invention provides a kit comprising such a composition. In yet another embodiment, the invention provides a kit comprising a first composition comprising a first molecular probe that detects a nucleotide sequence associated with a chromosomal aberration, and a second composition, wherein the second composition is an aqueous composition comprising at least one polar aprotic solvent in an amount effective to denature double-stranded nucleotide sequences.

The compositions and kits provided herein are useful for the in vivo, in vitro, and/or in situ analysis of nucleic acids, such as, e.g., genomic DNA, chromosomes, chromosome fragments, and genes using techniques such as PCR, in situ PCR, northern blot, Southern blot, flow cytometry, autoradiography, fluorescence microscopy, chemiluminescence, immunohistochemistry, virtual karyotype, gene assay, DNA microarray (e.g., array comparative genomic hybridization (array CGH)), gene expression profiling, Gene ID, Tiling array, gel electrophoresis, capillary electrophoresis, and in situ hybridizations such as FISH, SISH, CISH. In one embodiment, the compositions and kits are useful for the in vivo, in vitro, or in situ analysis of nucleic acids for chromosomal aberrations such as aneuploidy, potential breakpoint, insertion, inversion, deletion, duplication, gene amplification, rearrangement, and translocation associated with a normal condition or disease (such as, e.g. a congenital disease, cancer, or infection). The compositions and kits provided herein are also useful for the detection of changes in RNA expression levels, e.g., mRNA and its complementary DNA (cDNA). The compositions and kits of the invention may be used on in vitro, in vivo, or in situ samples (including, e.g., mammalian samples such as, e.g., human samples) such as bone marrow smears, blood smears, paraffin embedded tissue preparations, enzymatically dissociated tissue samples, bone marrow, amniocytes, cytospin preparations, imprints, etc.

Other uses include solution-based hybridization assays using FRET and other quenching techniques; detecting biotin labels with strepavidin conjugates, e.g., using the in situ Dako GenPoint™ amplified detection system or the Tyramide Signal Amplification (TSA) system (K0620, Dako); or direct labeling with metals, e.g., gold and silver.

In one embodiment, the invention provides a method of detecting a target in chromosomal DNA comprising:
  providing at least one molecular probe that hybridizes to the target in chromosomal DNA,
  providing chromosomal DNA,
  providing a hybridization composition comprising at least one polar aprotic solvent in an amount effective to denature double-stranded nucleotide sequences, wherein the polar aprotic solvent is not dimethyl sulfoxide (DMSO),
  combining the molecular probe, the chromosomal DNA and the hybridization composition for at least a time period sufficient to hybridize the molecular probe to the target, and
  detecting the target.

In another embodiment, the invention provides a method of determining the presence of a chromosomal aberration in a nucleic acid sequence, the method comprising:
  providing at least one molecular probe,
  providing the nucleic acid sequence,
  providing a hybridization composition comprising at least one polar aprotic solvent in an amount effective to denature double-stranded nucleotide sequences, wherein the polar aprotic solvent is not dimethyl sulfoxide (DMSO),
  combining the molecular probe and the nucleic acid sequence and the hybridization composition for at least a time period sufficient to hybridize the molecular probe and the nucleic acid sequence, and
  detecting the at least one molecular probe,
  and determining the presence of the chromosomal aberration.

In yet another embodiment, the invention provides a method of determining the presence of a chromosomal aberration in a nucleic acid sequence, the method comprising:

providing the nucleic acid sequence,
providing a hybridization composition comprising at least one molecular probe and at least one polar aprotic solvent in an amount effective to denature double-stranded nucleotide sequences,
applying the hybridization composition to said nucleic acid for at least a time period sufficient to hybridize the molecular probe and nucleic acid sequence, and
detecting the at least one molecular probe,
and determining the presence of the chromosomal aberration, wherein the polar aprotic solvent is not dimethyl sulfoxide (DMSO).

In another embodiment, the invention provides a method of determining the presence of a chromosomal aberration in a nucleic acid sequence, the method comprising:
providing the nucleic acid sequence,
applying a composition according to any one of claims 1 to 50 to said nucleic acid sequence for at least a time period sufficient to hybridize the molecular probe and nucleic acid sequence, and
determining whether the chromosomal aberration is present in the nucleic acid sequence.

In a further embodiment, the invention provides a method of diagnosing a congenital genetic disorder, cancer, or infection associated with a chromosomal aberration, the method comprising providing a tissue sample from a subject, wherein the tissue sample comprises a nucleic acid sequence, determining whether a chromosomal aberration is present in the nucleic acid sequence, and diagnosing the congenital genetic disorder, cancer, or infection if the chromosomal aberration is present in the tissue sample. The sample may be a mammalian sample. In one embodiment, the sample is a human sample.

The hybridization compositions and methods of the invention may, for example, eliminate the use of, or reduce the dependence on, formamide. For example, the methods and compositions of the invention may lower the energy barrier to hybridization without the use of formamide. The lower energy barrier may reduce the time and or temperature necessary for hybridization. For example, the invention may allow for hybridization at lower temperatures, including room temperature, or may allow for rapid hybridization at higher temperatures. Thus, in some aspects, the present invention overcomes a major time consuming step in hybridization assays.

One aspect of the invention is a composition or solution for use in hybridization. Compositions for use in the invention include an aqueous composition comprising at least one nucleic acid sequence and at least one polar aprotic solvent in an amount effective to denature double-stranded nucleotide sequences. An amount effective to denature double-stranded nucleotide sequences is an amount that enables hybridization. For example, one way to test for whether the amount of polar aprotic solvent is effective to enable hybridization is to determine whether the polar aprotic solvent, when used in the hybridization methods and compositions described herein, such as example 1, yield a detectable signal and/or an amplified nucleic acid product.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, or 50% to 60% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

According to another aspect of the present invention the aqueous composition comprising a polar aprotic solvent has reduced toxicity. For example, a less-toxic composition than traditional hybridization solutions may comprise a composition with the proviso that the composition does not contain formamide, or with the proviso that the composition contains less than 10%, or less than 5%, or less than 2%, or less than 1%, or less than 0.5%, or less than 0.1%, or less than 0.05%, or less than 0.01% formamide. A less-toxic composition may also comprise a composition with the proviso that the composition does not contain dimethyl sulfoxide (DMSO), or with the proviso that the composition contains less than 10%, 5%, 2%, or less than 1%, or less than 0.5%, or less than 0.1%, or less than 0.05%, or less than 0.01% DMSO.

In one aspect of the invention, suitable polar aprotic solvents for use in the invention may be selected based on their Hansen Solubility Parameters. For example, suitable polar aprotic solvents may have a dispersion solubility parameter between 17.7 to 22.0 $MPa^{1/2}$, a polar solubility parameter between 13 to 23 $MPa^{1/2}$, and a hydrogen bonding solubility parameter between 3 to 13 $MPa^{1/2}$.

According to one aspect of the present invention, suitable polar aprotic solvents for use in the invention are cyclic compounds. A cyclic compound has a cyclic base structure. Examples include the cyclic compounds disclosed herein. In other embodiments, the polar aprotic solvent may be chosen from Formulas 1-4 below:

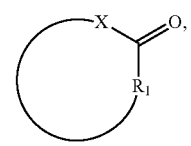

Formula 1

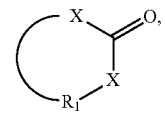

Formula 2

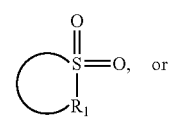

Formula 3

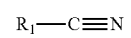

Formula 4 where X is O and R1 is alkyldiyl.

According to another aspect of the invention, suitable polar aprotic solvents for use in the invention may be chosen from Formula 5 below:

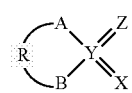

Formula 5 where X is optional and if present, is chosen from O or S;
where Z is optional and if present, is chosen from O or S;

where A and B independently are O or N or S or part of the alkyldiyl or a primary amine;
where R is alkyldiyl; and
where Y is O or S or C.

Examples of suitable polar aprotic solvents according to Formula 5 are provided in Formulas 6-9 below:

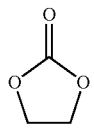

Formula 6 where:
X is non-existing;
A, B, and Z are O;
Y is C; and
R is Ethane-1,2 diyl;

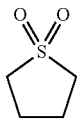

Formula 7 where:
Z and X are O;
A and B are part of the alkyldiyl;
Y is S; and
R is Butane-1,4 diyl;

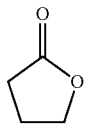

Formula 8 where:
X is non-existing;
A is part of the alkyldiyl;
Y is C;
B and Z is O; and
R is Propane-1,3 diyl;

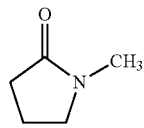

Formula 9 where:
X is non-existing;
A is part of the alkyldiyl;
Y is C;
B is methylamine;
Z is O; and
R is Propane-1,3 diyl According to yet another embodiment of the invention the polar aprotic solvent has lactone, sulfone, nitrile, sulfite, or carbonate functionality. Such compounds are distinguished by their relatively high dielectric constants, high dipole moments, and solubility in water.

According to another aspect of the invention the polar aprotic solvent having lactone functionality is γ-butyrolactone (GBL), the polar aprotic solvent having sulfone functionality is sulfolane (SL), the polar aprotic solvent having nitrile functionality is acetonitrile (AN), the polar aprotic solvent having sulfite functionality is glycol sulfite/ethylene sulfite (GS), and the polar aprotic solvent having carbonate functionality is ethylene carbonate (EC), propylene carbonate (PC), or ethylene thiocarbonate (ETC).

DETAILED DESCRIPTION

I. Definitions

Figure 1:
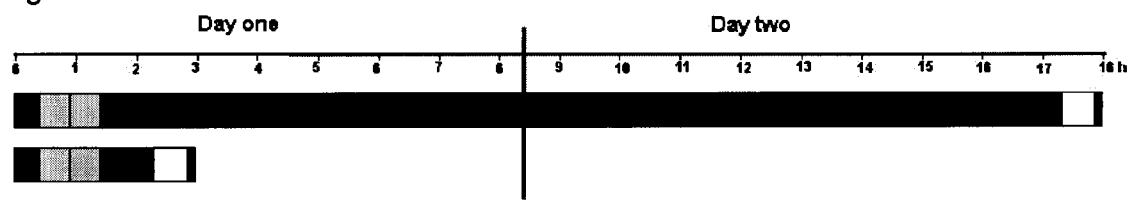
FIG. 1 depicts a typical time-course for single locus detection with primary labeled FISH probes on formaldehyde fixed paraffin embedded tissue sections (histological specimens). The bars represent a hybridization performed using a traditional solution (top) and a typical time-course for a hybridization performed using a composition of the invention (bottom). The first bar on the left in each time-course represents the deparaffination step; the second bar represents the heat-pretreatment step; the third bar represents the digestion step; the fourth bar represents the denaturation and hybridization step; the fifth bar represents the stringency wash step; and the sixth bar represents the mounting step.

In the context of the present invention the following terms are to be understood as follows:

"Biological sample" is to be understood as any in vivo, in vitro, or in situ sample of one or more cells or cell fragments. This can, for example, be a unicellular or multicellular organism, tissue section, cytological sample, chromosome spread, purified nucleic acid sequences, artificially made nucleic acid sequences made by, e.g., a biologic based system or by chemical synthesis, microarray, or other form of nucleic acid chip. In one embodiment, a sample is a mammalian sample, such as, e.g., a human, murine, feline, rat, or canine sample.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., a peptide nucleic acid (PNA) or locked nucleic acid (LNA)), or any derivatized form of a nucleic acid.

As used herein, the term "peptide nucleic acid" or "PNA" means a synthetic polymer having a polyamide backbone with pendant nucleobases (naturally occurring and modified), including, but not limited to, any of the oligomer or polymer segments referred to or claimed as peptide nucleic acids in, e.g., U.S. Pat. Nos. 5,539,082, 5,527,675, 5,623,049, 5,714, 331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163, WO96/04000, all of which are herein incorporated by reference, or any of the references cited therein. The pendant nucleobase, such as, e.g., a purine or pyrimidine base on PNA may be connected to the backbone via a linker such as, e.g., one of the linkers taught in PCT/US02/30573 or any of the references cited therein. In one embodiment, the PNA has an N-(2-aminoethyl)-glycine) backbone. PNAs may be synthesized (and optionally labeled) as taught in PCT/US02/30573 or any of the references cited therein. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270:1628-44 (2003).

Examples of nucleic acids and nucleic acid analogs also include polymers of nucleotide monomers, including double and single stranded deoxyribonucleotides (DNA), ribonucleotides (RNA), α-anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof. DNA, RNA, or other nucleic acids as defined herein can be used in the method and compositions of the invention.

"Polar aprotic solvent" refers to an organic solvent having a dipole moment of about 2 debye units or more, a water solubility of at least about 5% (volume) at or near ambient temperature, i.e., about 20° C., and which does not undergo significant hydrogen exchange at approximately neutral pH, i.e., in the range of 5 to 9, or in the range 6 to 8. Polar aprotic solvents include those defined according to the Hansen Solubility Parameters discussed below.

"Alkyldiyl" refers to a saturated or unsaturated, branched, straight chain or cyclic hydrocarbon radical having two monovalent radical centers derived by the removal of one hydrogen atom from each of two different carbon atoms of a parent alkane, alkene, or alkyne.

"Aqueous solution" is to be understood as a solution containing water, even small amounts of water. For example, a solution containing 1% water is to be understood as an aqueous solution.

"Hybridization" is to be understood to incorporate both the denaturation and re-annealing steps of the hybridization procedure unless otherwise specified.

"Hybridization composition" refers to an aqueous solution of the invention for performing a hybridization procedure, for example, to bind a probe to a nucleic acid sequence. Hybridization compositions may comprise, e.g., at least one polar aprotic solvent, at least one nucleic acid sequence, and a hybridization solution. Hybridization compositions do not comprise enzymes or other components, such as deoxynucleoside triphosphates (dNTPs), for amplifying nucleic acids in a biological sample.

"Hybridization solution" refers to an aqueous solution for use in a hybridization composition of the invention. Hybridization solutions are discussed in detail below and may comprise, e.g., buffering agents, accelerating agents, chelating agents, salts, detergents, and blocking agents.

"PCR composition" refers to an aqueous solution of the invention for performing a hybridization procedure to amplify a nucleic acid sequence. PCR compositions may comprise, e.g., at least one polar aprotic solvent, at least one enzyme for amplifying nucleic acids, a set of nucleic acid oligonucleotide primers, a mixture of dNTPs, and a PCR solution.

"PCR solution" refers to an aqueous solution for use in a PCR composition of the invention. PCR solutions may comprise e.g., buffering agents, accelerating agents, chelating agents, salts, and detergents.

The term "detecting," as used, for example, in the context of a molecular probe detecting a nucleotide sequence associated with a chromosomal aberration, means that the molecular probe hybridizes to at least a portion of the nucleotide sequence or a nucleotide sequence in proximity to such sequence, which would allow a user to determine the presence or absence of the sequence.

The term "marker," such as a marker for a chromosomal aberration, is any sequence that is associated with a chromosomal aberration that may be used to detect the presence or absence of a chromosomal aberration with, or without, the use of one or more other markers.

"Hansen Solubility Parameters" and "HSP" refer to the following cohesion energy (solubility) parameters: (1) the dispersion solubility parameter ($\delta_D$, "D parameter"), which measures nonpolar interactions derived from atomic forces; (2) the polar solubility parameter ($\delta_P$, "P parameter"), which measures permanent dipole-permanent dipole interactions; and (3) the hydrogen bonding solubility parameter ($\delta_H$, "H parameter"), which measures electron exchange. The Hansen Solubility Parameters are further defined below.

"Repetitive Sequences" is to be understood as referring to the rapidly reannealing (approximately 25%) and/or intermediately reannealing (approximately 30%) components of mammalian genomes. The rapidly reannealing components contain small (a few nucleotides long) highly repetitive sequences usually found in tandem (e.g., satellite DNA), while the intermediately reannealing components contain interspersed repetitive DNA. Interspersed repeated sequences are classified as either SINEs (short interspersed repeat sequences) or LINEs (long interspersed repeated sequences), both of which are classified as retrotransposons in primates. SINEs and LINEs include, but are not limited to, Alu-repeats, Kpn-repeats, di-nucleotide repeats, tri-nucleotide repeats, tetra-nucleotide repeats, penta-nucleotide repeats and hexa-nucleotide repeats. Alu repeats make up the majority of human SINEs and are characterized by a consensus sequence of approximately 280 to 300 by that consist of two similar sequences arranged as a head to tail dimer. In addition to SINEs and LINEs, repeat sequences also exist in chromosome telomeres at the termini of chromosomes and chromosome centromeres, which contain distinct repeat sequences that exist only in the central region of a chromosome. However, unlike SINES and LINES, which are dispersed randomly throughout the entire genome, telomere and centromere repeat sequences are localized within a certain region of the chromosome.

"Non-toxic" and "reduced toxicity" are defined with respect to the toxicity labeling of formamide according to "Directive 1999/45/EC of the European Parliament and of the Council of 31 May 1999 concerning the approximation of the laws, regulations and administrative provisions of the Member States relating to the classification, packaging, and labelling of dangerous preparations" (ecb.jrc.it/legislation/1999L0045EC.pdf) ("Directive"). According to the Directive, toxicity is defined using the following classification order: T+ "very toxic"; T "toxic", C "corrosive", Xn "harmful", .Xi "irritant." Risk Phrases ("R phrases") describe the risks of the classified toxicity. Formamide is listed as T (toxic) and R61 (may cause harm to the unborn child). All of the following chemicals are classified as less toxic than formamide: acetonitrile (Xn, R11, R20, R21, R22, R36); sulfolane (Xn, R22); γ-butyrolactone (Xn, R22, R32); and ethylene carbonate (Xi, R36, R37, R38). At the time of filing this application, ethylene trithiocarbonate and glycol sulfite are not presently labeled.

A "molecular probe" refers to a "nucleic acid" probe or to a "nucleic acid analog" probe. As used herein, the term "probe" is to be understood as a nucleic acid chain, which may be composed entirely of DNA, RNA, PNA, LNA, synthetic or natural analogs thereof, or mixtures thereof, that detects a particular nucleotide sequence. In addition, bases in a probe may be joined by a linkage other than a phosphodiester bond, so long as it does not prevent hybridization. A molecular probe that detects a particular mutation is one that binds a target sequence characteristic of that mutation. The term "bind" is synonymous with "hybridize." When two molecules hybridize, they form a combination of the two molecules through one or more types of chemical bonds, through complementary base pairing, or through hydrogen bond formation. The term "target sequence" refers to the nucleobase sequence sought to be determined.

A "chromosomal aberration" or chromosomal abnormality is a variation from a normal chromosomal sequence, such as, e.g. a change in chromosome number (aneuploidy), a change in a gene copy number (amplification, deletion, duplication, aneuploidy), potential breakpoint, insertion, inversion, rearrangement, or translocation.

II. Compositions

The present invention provides compositions comprising molecular probes and aqueous compositions (comprising at least one polar aprotic solvent in an amount effective to denature double-stranded nucleotide sequences) for use in hybridization. In general, such compositions may comprise any molecular probe(s) and any aqueous composition described herein.

A. Molecular Probes

Molecular probes that are suitable for use in the invention are described, e.g., in U.S. Patent Publication No. 2005/0266459, which is incorporated herein by reference. In general, a molecular probe is typically a double or single stranded nucleic acid, including, e.g., DNA, RNA, PNA, and LNA. A probe may be any suitable length for detecting the target. Generally, a probe is made up of smaller fragments of varying sizes (e.g., about 50 by to about 500 by each) such that the probe will, in total, span about 30 kb to about 2 Mb. For example, a probe may be 1-100, 1-10, 7-15, 10-200, 10-20, 10-30, 10-50, 20-40, 30-50, 40-60, 50-70, 50-100, 50-150, 60-80, 70-90, or 80-100 kb in length. The probes may be used to detect, quantify, identify, or analyze nucleic acid molecules or other molecules that bind to the probes.

In general, probes may be prepared by chemical synthesis or by amplifying a specific DNA sequence by cloning, inserting the DNA into a vector, and amplifying the vector an insert in appropriate host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted and purified for use as a probe. Methods for preparing and/or synthesizing probes are known in the art, e.g., as disclosed in PCT/US02/30573.

The probes used in the methods and compositions of the invention will, in one embodiment, comprise both unique fragments as well as repeated fragments. Nucleic acid analog probes, such as PNA probes, are generally shorter, well-defined probes typically comprising from about 10 to 15 nucleobases. A PNA probe is usually composed of several individual probes, each having 10 to 25 nucleobase units.

In one embodiment, the invention provides a single molecular probe. In another embodiment, the invention provides a pair of molecular probes. In other embodiments, the invention provides 2, 3, 4, 5, 10, or more probes or pairs of probes. In one embodiment, a distinct and balanced pair of probes is used, as taught in U.S. Pat. No. 6,730,474, which is incorporated herein by reference. Each of the distinct and balanced pairs of probes may, for example, hybridize to different chromosomes involved in a translocation, or to flanking regions of a potential breakpoint. In another embodiment, two sets of hybridization probes may be employed, one or more of which comprise PNA probes, as in U.S. Pat. No. 7,105,294, which is incorporated herein by reference. In one embodiment, at least two sets of hybridization probes are used, at least one set capable of hybridizing to specific nucleic acid sequences related to a potential aberration in a chromosome, and at least another set capable of hybridizing to specific nucleic acid sequences related to another or the same potential aberration in a chromosome.

There are several types of probes that may be used for hybridizing to a nucleic acid sample (See generally Szeles, Acta Microbiol. Immunol. Hungarica, 49:69-80 (2002)). These probes include short sequences of genomic DNA or cDNA, whole chromosome paints, chromosome repeats, and whole genomes. In the case of genomic probes, frequently repeated sequences in mammalian genomes have relatively little evolutionary conservation. Thus, total nuclear or genomic DNA can be used as a species-specific probe. Chromosome paints are collections of DNA sequences derived from a single chromosome type and can identify that specific chromosome type in metaphase and interphase nuclei. Different chromosomal types also have unique repeated sequences that may be targeted for probe hybridization (See Cremer et al., Hum. Genet., 74:346-52 (1986)). Large insert probes that target unique single-copy sequences are another example of a probe type that may be used in hybridization assays. These probes may be in cosmids, bacterial artificial chromosomes (BACs), PI diverted artificial chromosomes (PACs), or yeast artificial chromosomes (YACs). With these large probes, the hybridization efficiency is inversely proportional to the probe size. Nonetheless, probes as small as 2 kb have been used (See Id.).

In general, the type of probe determines the type of feature the probe can detect. Probes that hybridize along an entire chromosome (whole chromosome painting) are used to count the number of a certain chromosome, show translocations, or identify extra-chromosomal fragments of chromatin. Smaller probes can also be used to detect aberrations such as deletions, amplifications, inversions, duplications, and aneuploidy. In another example, locus-specific probe mixtures may be used to detect and count specific chromosomes. Two or more differently-colored locus-specific probes, for example, can be used to detect translocations via split-signal in situ hybridization, and repetitive sequence specific centromeric probe mixtures may be used to detect and count specific chromosomes.

In general, the ability to discriminate between closely related sequences is inversely proportional to the length of the hybridization probe because the difference in thermal stability decreases between wild type and mutant complexes as probe length increases. Probes of greater than 10 by in length are generally required to obtain the sequence diversity necessary to correctly identify a unique organism or clinical condition of interest. For example, specific DNA sequences, such as the ABL gene, can be reliable stained using probes that are 15 kb long. On the other hand, sequence differences as subtle as a single base (point mutation) in very short oligomers (<10 base pairs) can be sufficient to enable the discrimination of the hybridization to complementary nucleic acid target sequences as compared with non-target sequences.

In one embodiment, at least one set of the in situ hybridization probes may comprise one or more PNA probes, as described in U.S. Pat. No. 7,105,294. PNA is a synthetic polymer having a peptide (N-(2-aminoethyl)-glycine) backbone with pendant purine and pyrimidine bases. Because the PNA backbone is uncharged, in contrast to DNA and RNA, PNA/DNA and PNA/RNA interactions are stronger than the corresponding DNA/DNA or DNA/RNA interactions would be. Consequently, PNA probes may be shorter than DNA or RNA probes while retaining similar specificity. PNA probes also show greater specificity in binding to complementary DNA or RNA, since PNA/DNA (or PNA/RNA) base mismatches are more destabilizing than similar mismatches in a DNA/DNA (or RNA/RNA) duplex. In addition, PNAs are relatively resistant to enzymatic degradation by proteases and nucleases.

Alternatively, or in addition, at least one set of the hybridization probes in any of the techniques discussed above may comprise one or more locked nucleic acid (LNA) probes, as described in WO 99/14226, which is incorporated herein by reference. LNAs contain an additional bridging bond between the 2' and 4' carbons, resulting in a rigid 3'-endo conformation and consequent pre-organization of the nucleotide backbone for hybridization. LNA/DNA and LNA/RNA interactions are stronger than the corresponding DNA/DNA and DNA/RNA interactions, as indicated by a higher melting temperature. Thus, the methods and compositions of the invention, which decrease the energy required for hybridization, are particularly useful for hybridizations with LNA probes.

In one embodiment, a probe may comprise a detectable label (a molecule that provides an analytically identifiable signal that allows the detection of the probe-target hybrid). As used herein, a detectable label refers to moieties that can be attached directly or indirectly to an oligomer or polymer to thereby render the oligomer or polymer detectable by an instrument or method. Any labeling method known to those in the art, including enzymatic and chemical processes, can be used for labeling probes used in the methods and compositions of the invention.

In one embodiment, a detectable label may be directly attached to a probe. In another embodiment, a detectable label may be indirectly attached to a probe, e.g., by using a linker. In other embodiments, the probes are not labeled.

A detectable label may be, for example, a fluorochrome, a chromophore, a spin label, a radioisotope, an enzyme, a hapten, Quantum Dot, beads, aminohexyl, pyrene, and a chemiluminescence compound, such as acridine orange. Fluorochromes that may be used in the method of the present invention include, but are not limited to, IR dyes, Dyomics dyes, phycoerythrine, cascade blue, Oregon green 488, pacific blue, rhodamine green, 5(6)-carboxyfluorescein, cyanine dyes (i.e., Cy2, Cy3, Cy 3.5, Cy5, Cy5.5, Cy 7) (diethylamino)coumarin, fluorescein (i.e., FITC), tetramethylrhodamine, lissamine, Texas Red, AMCA, TRITC, and Alexa dyes. Haptens that may be used in the present invention include, but are not limited to, 5(6)-carboxyfluorescein, 2,4-dinitrophenyl, digoxigenin, rhodamine, bromodeoxy uridine, acetylaminoflurene, mercury trinitrophenol, estradiol, and biotin. Enzymes that may be used in the present invention include, but are not limited to, soybean peroxidase, alkaline phosphatase, and horseradish peroxidase. In one embodiment, the label may be a radioactive label such as, e.g., $^{31}$P, $^{33}$P, or $^{32}$S. In another embodiment, a probe may be labeled with a hapten such as, e.g., digoxigenin or biotin. A probe may also be labeled with heavy metal particles or with an enzyme having chromogenic or fluorogenic substrates. A probe may also be labeled with any other label known to those skilled in the art.

Where more than one probe is present, each probe may be labeled with a distinct label. For example, in one embodiment, where FISH is performed and the hybridization mixture contains sets of distinct and balanced pairs of probes, as described in U.S. Pat. No. 6,730,474, the probes may be labeled with distinct labels of comparable intensity.

In an embodiment using chromogenic in situ hybridization (CISH), the hybridization mixture may contain at least one set of probes configured for detection with one or more conventional organic chromogens, and for silver in situ hybridization (SISH), the hybridization mixture may contain at least one set of probes configured for detection with silver particles, as described in Powell RD et al., "Metallographic in situ hybridization," Hum. Pathol., 38:1145-59 (2007).

In one embodiment, the formation of a probe-nucleic acid sequence hybrid is detected upon addition of a visualization reagent, such as, e.g., an antibody (which may be monoclonal, and which may itself comprise a label), a fluorogenic or chromogenic substrate for an enzyme, or any other suitable visualization reagent known to the skilled artisan.

In some embodiments, the probes may be used to detect changes in chromosomal structure by detecting a change in the pattern of staining of the sample compared to a normal control sample. Non-exhaustive examples of chromosomal alterations that may be detected with molecular probes include aneuploidy, gene amplifications, deletions including gene deletions, gene fusions, translocations, duplications, insertions, or inversions. As used herein, aneuploidy refers to any deviation from the normal euploid state or the condition of having less than or more than the normal diploid number of chromosomes. As used herein, an amplification refers to an increase in the number of copies of a specific DNA fragment. Such DNA fragments include, for example, a gene or an entire chromosome. As used herein, a deletion refers to a genetic event in which a nucleic acid sequence has been removed from a chromosome. As used herein, a gene fusion refers to an accidental joining of the DNA of two genes. Gene fusions may occur by translocations or inversions and may give rise to hybrid proteins or the misregulation of the transcription of one gene due to the juxtaposition of cis regulatory elements (e.g., enhancers or promoters) of another gene. As used herein, a translocation refers to a genetic event in which a part of the nucleic acid sequence of one chromosome is removed from that chromosome and attached to a different chromosome. As used herein, a duplication refers to the repetition of a nucleotide sequence in a chromosome or a chromosome segment. A duplication may result in the repetition of a nucleotide sequence in linear juxtaposition to the duplicated sequence. As used herein, an insertion refers to a genetic event in which a nucleic acid sequence has been introduced between two points in a chromosome. As used herein, an inversion is a genetic event in which a nucleic acid sequence's orientation in a chromosome has been reversed. As used herein, a chromosomal breakpoint refers to a location in the chromosome where the chromosome breaks into two pieces.

In some embodiments, the molecular probes may flank regions, for example, about 500,000 by on each side of the gene. An example of probes for the TYMS marker comprising about 500,000 by flanking regions are: CTD-2304H22; RP11-841C6; RP11-464L8; RP11-631M21; CTD-2573M23; CTD-3162G8G8; CTD-3232F7; RP11-170J2; RP11-252G7; RP11-699P24; RP11-805B24; CTD-3237F7; RP11-230P17; CTD-2359H18; RP11-1120H10; CTD- 2509F1; RP11-431C15; RP11-361O6; RP11-1066C16; CTD-2359H18; RP11-1066G14; RP11-1034P14; RP11-1034P22; CTD-3114P12; RP11-787A12; RP11-787C12; CTD-3149J12; RP11-195P12; CTD-2595P20; CTD-2168E8; RP11-621G7; CTD-3023M8; RP11-748B19; CTD-2064P19; RP11-461K16; RP11-630F5; CTD-3021E11; CTD-3028I7; RP11-1021K17; RP11-729G15; RP11-104I5; RP11-595D13; RP11-436O7; CTD-2646F10; RP11-104A15; CTD-2024F12; CTD-2169M24; RP11-140D22; RP11-848A7; CTD-2060D6; CTD-2298K5; CTD-3022J6; RP11-29P22; RP11-790O10; RP11-89P6; RP11-91I8; RP11-694N4; RP11-752I11; RP11-324G2; CTA-186D6; RP11-88C10; RP11-608N7; RP11-732L14; RP11-324G2; RP11-705O1; RP11-839O23; RP11-683J11; RP11-815L4; RP11-720L2; RP11-179K3; RP11-778P8; RP11-823F8; RP11-791M5; RP11-672L10; RP11-827M19; RP11-19J12; RP11-607C2; RP11-267C19; CTD-3214N24; RP11-1035E2; CTD-2004F18; CTD-3155L20; CTD-2281A22; CTD-3231L23; CTD-2014P18; RP11-1150C18; RP11-170J1; CTC-790I9; RP11-76H24; RP11-48I21; CTC-775A10; CTD-2034O18; RP11-431C11; RP11-50C2; CTD-2208G7; CTD-2345G8; RP11-797C9; RP11-133D9; RP11-655D4; RP11-14P20; RP11-103B23; RP11-806L2; RP11-145B19; CTD-2593J12; CTD-3215I7; RP11-381D10; RP11-769O8; RP11-95H4; RP11-552E8; RP11-914P23; RP11-904F1; RP11-164C14; CTD-3040A20; RP11-1152E8; CTD-3065D24; CTD-3243B17; CTD-3243D18; CTD-32431D19; CTD-3113H2; RP11-1120E20; CTD-3046I16; RP11-635J20; RP11-114M20; RP11-1018M4; CTA-344N3; RP11-137K7; RP11-689C9; RP11-1005B18; RP11-126M20; CTD-2134I3; RP11-701F4; CTD-3236J23; CTD- 3047L19; CTD-3240G16; CTD-3148N6; RP11-22J24; RP11-1094D2; CTD-2182K19; RP11-107A13; RP11-134P22; RP11-636P15; RP11-78F17; CTD-2221P22; CTD-2011M14; RP11-626B11; and RP11-27K24.

In other embodiments, the probes may bind within a chromosomal region encoding a gene or not encoding a gene. For example, the probes may bind to chromosomal regions associated with the 5-FU pathway including thymidylate synthase (TYMS), dihydrofolate reductase (DHFR), thymidine phosphorylase (TP), dihydropyrimidine dehydrogenase (DPD), methylenetetrahydrofolate reductase (MTHFR), thymidine kinase (TK), and 5-methyltetrahydrofolate-homocysteine me-thyltransferase (methionine synthase, MTR).

In one embodiment, a molecular probe detects a congenital genetic disorder such as, e.g., fragile X syndrome. Other congenital genetic disorders that may be detected include, e.g., Down Syndrome, Turner Syndrome, Wolf-Hirschhorn syndrome, Jacobsen syndrome, Charcot-Marie-Tooth disease type 1A, and Robertsonian translocation.

In one embodiment, a molecular probe detects a cancerous condition such as, e.g., a solid tumor including, e.g., bladder, breast, cervical, colorectal, liver, lung, pancreatic, prostate, skin, or uterine cancer. In one embodiment, the molecular probe detects a hematopoietic malignancy, such as, e.g., acute lymphoblastic leukemia, chronic lymphocytic leukemia, lymphoma, multiple myeloma, or non-Hodgkin's lymphoma. In one embodiment, the molecular probe detects a B-cell malignancy or a T-cell malignancy.

In another embodiment, a molecular probe detects an infectious pathogen, such as, e.g., a bacterium, virus, or fungus. For example, the pathogen may be, e.g., Epstein-Barr virus, human papilloma virus, or herpes simplex virus. In another example, the pathogen may be, e.g., *Escherichia coli, Klebsiella pneumoniae, Pseudomonas aeruginosa, Helicobacter pylori, Histoplasma capsulatum, Blastomyces dermatitidis, Coccidioides* species, *Cryptococcus neoformans, Cryptococcus gattii*, or herpes simplex virus.

In one embodiment, the molecular probe detects aberrations (including, e.g., rearrangements, amplifications, or deletions) of ALK, BCL2, BCL3, BCL6, BCL10, BCL12, BCR (22q11), CCND1, cyclinD1 (11q23), E2A (19p13), EGFR (7p11.2), ETV6 (TEL) (12p13), FIP1L1, HER2 (ERBB2) (17q21.1), IGH (14q32), IGK (2p11), IGL (22q11), MALT1, MLL (ALL-1, HTRX1, HRX) (11q23), MYC (c-Myc) (8q24), PAX5, PDGFRA, PDGFRB, SIL, TCF3 (E2A, ITF1), TCL1A, TCRAD, TCRB, TCRG, telomere, TLX1, TLX3 (HOX11L2, RNX), or TOP2A. For example, the probes may be used to detect a common gene rearrangement in childhood caner characterized by the fusion of ETV6 and AML1 (also known as RUNX1 and CBFA2).

In one embodiment (including, e.g., in the context of a hemoatopoietic malignancy), a molecular probe detects a translocation, such as, e.g., a translocation chosen from t(1; 14) (q34;q11), t(1;19) (q23;p13), t(2;5), t(2;18) (q12;q21), t(2;8), t(4;11), t(4;11) (q21;q23), t(6;11) (q27;q23), t(7;22) (p22;q12), t(8;14), t(8;22), t(9;11) (p22;q23), t(9;22), (q34; q11), t(10;14) (q24;q11), t(11;14), t(11;14) (p13;q11), t(11; 19) (q23;p13), t(14;18), (q23;q21), t(14;18), t(18;22) (q21; q11), and t(21;22) (q22;q12). n another embodiment, a molecular probe detects a deletion, such as a deletion of TAL1. In yet another embodiment, a molecular probe detects a gene amplification, such as an amplification of EGFR, MYC, TOP2A, or HER2. In such cases, a probe may be paired with a reference probe. For example, a probe that detects EGFR may be paired with a probe that detects CEN-7, a probe that detects MYC may be paired with a probe that detects CEN-8, and a probe that detects HER2 may be paired with a probe that detects CEN-17.

Exemplary targets for probes that may be used in the compositions and methods of the invention for detecting non-hemaetological diseases include, e.g., BASE, BRCA1, CCND1, CCNE1, DCD, E2F3, n-MYC/MYCN, COX-2/ PTGS2, LRIG1, ER a, hTERT, MLN64/ STARD3, PGR, SNAI1, SRC, TOP1, TUBB1, AIB1, DLC-1, EDD, Pip4k2b/ 5k, Sil, TBX2, c-Kit, VEGF, VCAM-1, Tie-1, Ts/TYMS, PSMA, PSA, PAP, P15, P16, BCL1, BCL2, MTOR, TIMP1, ESR1, PTEN, MDM2/CDK4, MET, C-MET, ERB1, FGFR1, IGF1R, NET, FGFR3, ABCB1, TMPRSS2, BRCA2, TOP2B, ERCC1, AKT1, AKT2, AKT3, HRAS, NRAS, RAF1, HER3, HER4, ENT1, RRM1, RRM2, RRM2B, PIK3CA, AURK4, AURKB, AURKC, MAPT/tau, TTBK1, TUBB, VEGFR, CCND3, CDK6, CDK2, CDC2, HDAC, ESR2, SCUBE2, BIRC5, FASN, DHFR, TP/ECGF1, TYMP, DPYD, TK1, HMGIC, ABCA2, ABCB11, ABCC1, ABCC2, ABCC3, ABCC4, ABCC5, ABCG2, MVP, ATP7A, ATP7B, SLC29A1, SLC28A1, SLC19A1, TUBB4, TUBA, MAP4, MAP7, STMN1, KIF5B, HSPA5, PSMD14, FPGS, GSTP1, GPX, GCLC, GGT2, MT, AKR1B1, HMGB1, HMGB2, XPA, XPD, MSH2, MLH1, PMS2, APEX1, MGMT, GLO1, RB1, GML, CDKN1A, CDKN2A, CDKN1B, ERBB2, KRAS2, ITGB1, JUN, FOS, NFKB1, TP53, TP73, BCL2L1, MCL1, BAX, BIRC4, TNFRSF6, CASP3, CASP8, HSPB1, MALAT1(alpha) t(11;19)(q11;q13.4), MHLB1 t(11;19) (q11;q13.4), COL1A1 t(17;22)(q22;q13), PDGFB t(17;22) (q22;q13), FKHR t(2;13) & t(1;13), ETV6 t(12;15)(p13; q25), NTRK3 t(12;15)(p13;q25), TLS/FUS t(12;16)(q13; p11), CHOP t(12;16)(q13;p11), EWS t(12;22)(q13;q12), EWS/FLI1 t(11;22)(q24;q12), and FLI1 t(11;22)(q24;q12).

Exemplary targets for probes that may be used in the compositions and methods of the invention for detecting hematological diseases include, e.g., probes for detecting targets of chronic myeloproliferative diseases such as, e.g., ABL t(9;22)(q34;q11), PRDM16 del(1p36.32), del(21q22.12), RUNX1/AML1 del(1p36.32), del(21q22.12), CEP8, PDGFRB, NUP98, FGFR1, and ASS; probes for detecting targets of acute myeloid leukemia, such as, e.g., ETO t(8;21)(q22; q22), AML1 t(8;21)(q22;q22), CBFbeta inv(16)(p13q22) or t(16;16)(p13;q22), MYH11 inv(16)(p13q22) or t(16;16) (p13;q22), AF9 t(9;11), PML t(15;17)(q22;q21), PLZF t(11; 17)(q23;q21), NuMA t(11;17)(q13;q21), NPM t(5;17)(q23; q12), RAR alpha t(15;17)(q22;q21) t(11;17)(q23;q21) t(11; 17)(q13;q21) t(5;17)(q23;q21), EVI1 t(3;v)(q26;v), GR6 t(3; 3)(q21; q26), RPN1 t(3;3)(q21;q26), DEK t(6;9), CAN t(6; 9), MLF1 t(3;5)( . . . ;q23), FUS t(16;21), ERG t(16;21), NUP98 t(7;11), HOX9A t(7;11), MOZ/MYST3 t(8;16)(p11; p13), CBP t(8;16)(p11;p13), p300 t(8;22)(p11;q13), TIF2/GRIP-1/NCoA-2 inv(8)(p11q13), and MKL1; probes for detecting targets of precursor B- and T-cell neoplasms, such as, e.g., PBX1 t(1;19)(q23;p13.3)+var., ABL t(9;22)(q34; q11), AF4/AFF1 t(4;11)(q21;q23), AML1/RUNX1 t(12;21) (p13;q22), IL3 t(5;14)(q31;q32), HLF t(17;19), IKZF1 del(7) (p12.2), CDKN2A/CDKN2B del(9)(p21.3), TAL1 1p32 aberrations, LMO2 t(11;14)(p13;q11)+var., LMO1 t(11;14) (p15;q11), HOX11 t(10;14)(q24;q11)+var TAL2 t(7;9)(q34; q32), and TAN1 t(7;9)(q34;q34); probes for detecting targets of mature B-cell neoplasms, such as, e.g., CEP12, ATM, D13S25, D13S319, TP53, P53, TNFAIP3 del(6)(q23.3-q24.1), CDK6 BCL1 t(11;14)(q13;q32)+var., IRF4 t(6;14) (p25; q32), C-MAF t(14;16)(q32;q23), FGFR3 t(4;14)(p16; q32), and MUM2/3 t(1;14)(q21;q32); and probes for detecting targets of mature T-cell and NK-cell neoplasms, such as, e.g., NPM t(2;5)(p23;q35), ASS, RB1, and ATM.

Exemplary targets for probes that may be used in the compositions and methods of the invention for detecting centromeres include, e.g., CEP1, CEP2, CEP3, CEP4, CEP5, CEP6, CEP7, CEP8, CEP9, CEP10, CEP11, CEP12, CEP13, CEP14, CEP15, CEP16, CEP17, CEP18, CEP19, CEP20, CEP21, CEP22, CEP23, CEP X, and CEP Y.

Exemplary targets for probes that may be used in the compositions and methods of the invention also include, e.g., CEP 18 (18p11.1-q11.1) , CEP X (Xp11.1-q11.1), CEP Y (Yp11.1-q11.1), LSI 13 (13q14), LSI 21 (21q22.13-q22.2), CEP 3 (3p11.1-q11.1), CEP 7 (7p11.1-q11.1), LSI (p16 9p21), CEP 17 (17p11.1-q11.1), CEP 1 (D1Z5) 1p11.1-q11.1, CEP 1 1q12, CEP 2 (D2Z1) 2p11.1-q11.1, CEP 3 (D3Z1) 3p11.1-q11.1, CEP 4 4p11-q11, CEP 6 (D6Z1) 6p11.1-q11, CEP 6 (D6Z1) 6p11.1-q11.1, CEP 7 (D7Z1) 7p11.1-q11.1, CEP 8 (D8Z2) 8p11.1-q11.1, CEP 9 9p11-q11, CEP 10 10p11.1-q11.1, CEP 11 (D11Z1) 11p11.11-q11.11, CEP 11 (D11Z1) 11p11.11-q11, CEP 12 (D12Z3) 12p11.1-q11, LSI 13 (13q14), LSI 13 (RB1), CEP 15 (D15Z1) 15p11.2, CEP 15 (D15Z4) 15p11.1-q11.1, CEP 16 (D16Z3) 16q11.2, CEP 17 (D17Z1) 17p11.1-q11.1, CEP 18 (D18Z1) 18p11.1-q11.1, CEP 20 (D20Z1) 20p11.1-q11.1, LSI 21, LSI 22 (BCR), CEP X (DXZ1) Xp11.1-q11.1, CEP X (DXZ1)/Y (DYZ1)*Xp11.1-q11.1 Yq12, CEP X (DXZ1)/Y (DYZ3) Xp11.1-q11.1 Yp11.1-q11.1, CEP Y (DYZ1) Yq12, CEP Y (DYZ1), Yq12, CEP Y (DYZ1), CEP Y (DYZ3) Yp11.1-q11.1, LSI 1p36/LSI 1q25 and LSI 19q13/19p13, LSI 4q12, LSI 9q34, LSI 13 (RB1) 13q14, LSI 13 (RB1), LSI (13q34), LSI 13 (13q14), LSI 21, LSI 22 (BCR), LSI ALK, LSI AML1/ETO, LSI Androgen Receptor Gene (Xq12), LSI API2/MALT1 t(11;18) (q21;q21), LSI ATM (11q22.3), LSI ATM/CEP 11, LSI BCL2, LSI BCR/ABL+9q34, LSI BCR/ABL, LSI CBFB, LSI CCND1 (11q13), LSI CHOP (12q13), LSI CSF1R (5q33-q34)/D5S23,D5S721, LSI C-MYC (8q24.12-q24.13), LSI Cyclin D1 (11q13)/CEP 11, LSI D13S25 (13q14.3), LSI D13S319 (13q14.3), LSI D13S319 (13q14.3)/LSI 13q34, LSI D20S108 (20q12), LSI D5S23/D5S721, CEP9, CEP15, LSI D7S486 (7q31)/CEP 7, LSI D7S522 (7q31)/CEP 7, LSI EGFR/CEP 7, LSI EGR1 (5q31)/D5S23, D5S721, LSI ETV6 (TEL) (12p13), LSI EWSR1 (22q12), LSI FKHR (13q14), LSI FUS (16p11), LSI IGH, LSI IGH/BCL2, LSI IGH/CCND1, LSI IGH/FGFR3, LSI IGH/MAF, LSI IGH/MALT1 t(14;18) (q32;q21), LSI IGH/MYC, CEP 8, LSI MALT1 (18q21), LSI MLL, LSI MYB (6q23), LSI MYC, LSI N-MYC (2p24.1), LSI N-MYC(2p24)/CEP 2 S, LSI p16 (9p21) /CEP 9, LSI p53 (17p13.1), LSI p53/LSI ATM and LSI D13S319/LSI 13q34/CEP 12, LSI PML/RARA, LSI PTEN (10q23)/ CEP 10, LSI RARA, LSI SYT (18q11.2), LSI TEL/AML1, LSI TCF3/PBX1, LSI TCR alpha/delta, LSI TOP2A, LSI TP53/CEP 17, LSI ZNF217 (20q13.2), LSI p58 (1p36) LSI 1q25, LSI D5S23, D5S721, LSI EGR1/LSI D5S23, D5S721, LSI N25/ARSA, LSI TUPLE 1/LSI ARSA, LSI TUPLE1 (HIRA)/TelVysion 22q S, LSI KAL/CEP X, LSI LIS1/LSI RARA, LSI D15S10/CEP 15 (D15Z1)/PML, LSI D15S11/CEP 15 (D15Z1), LSI GABRB3/CEP 15 (D15Z1), LSI SNRPN/CEP 15 (D15Z1)/LSI PML, LSI SMS Region/LSI RARA, LSI NSD1 (5q35), LSI SRY/CEP X, LSI SRY, LSI STS/LSI CEP X, LSI ELNe/LSI D7S486, D7S522, LSI WHS/CEP 4, CEB108/T7 1p, VIJ2yRM2052 (U32389) 2p, 3PTEL25 (D3S4559) 3p, 4p022 (D4S3359, 6244599) 4p, C84c11/T7 5p, 6PTEL48 6p, VIJ2yRM2185 (G31341) 7p, AFM 197XG5 (D8S504, 199153) 8p, 305J7-T7 9p, 10p006 (Z96139) 10p, VIJ2 (D11S2071, U12896) 11p, VIJ3 (sAVH27,U57865) 12p, STSG608831 STSG608938 16p, 282M16/SP6 17p, VIJ2yRM2102 (D18S552) 18p, 129F16/SP6 19p, 20p18 (D20S1157) 20p, DXYS129,DXYS153 Xp/Yp, VIJ2yRM2123 1QTEL10 (D1S3738, 9043912) 1q, VIJ2yRM2112 (D2S447) 2QTEL47 2q, 3QTEL05 (D3S4560) 3q, AFM A224XH1 (D4S2930) 4q, GS35o8/T7 5QTEL702 (D5S2907) 5q, VIJ2yRM2158 6q, VIJ2yRM2185 (STS 2000H, G31341) 7q, VIJ2yRM2053 8q, VIJ2yRM2241 (D9S325) 9q, 10QTEL24 (D10S2490, 6244631) 10q, D11S1037 11q, VIJ2yRM2196 12q, VIJ2yRM2002 (D13S327) 13q, D14S1420 14q, WI-5214 (D15S396) (G04801) 15q, 16q013 (Z96319) 16q, D17S928 Z23646 17q, VIJ2yRM2050 18QTEL11 STSG193 AFM254VD5 CU18-010L/CU18-010R STS-F04195 TIGR-A008P37 STSG52963 18q, D19S238E 19q, 20QTEL14 20q, VIJ2yRM2029 21q, MS607 (X58044) ACR 22q, and EST Cdy 16c07 for SYBL1—maps within cosmid C8.2 (Z43206) Xq/Yq.

Exemplary probes that may be used in the compositions and methods of the invention also include, e.g., probes that bind within the IN region of the POL gene of HIV subtypes A, B, C, D, AE, F, AG, G and O; probes that bind within the PR gene and the RT region of the POL gene of HW-1; and probes for detecting the cryptic plasmid of Chlamydia trachomatis; probes for detecting the Opa gene of Neisseria gonorrhoeae; probes that bind to p and q subtelomeres of chromosomes 1-12 and 16-20, q subtelomeres of the acrocentric chromosomes 13, 14, 15, 21, and 22, and Xp/Yp and Xq/Yq pseudoautosomal region subtelomeres; probes that bind in Exons 2 or 3 of HLA-A; probes that bind in Exons 2 or 3 of HLA-B; probes that bind in Exons 2 or 3 of HLA-C; probes that bind in Exon 2 of HLA-DRB1; probes that bind in Exon 2 of HLA-DPB1; and probes that bind in Exon 2 of HLA-DQB 1.

B. Aqueous Compositions (1) Solvent Selection

Suitable polar aprotic solvents for use in the invention may be selected based on their Hansen Solubility Parameters. Methods for experimentally determining and/or calculating HSP for a solvent are known in the art, and HSP have been reported for over 1200 chemicals.

For example, the D parameter may be calculated with reasonable accuracy based on refractive index, or may be derived from charts by comparison with known solvents of similar size, shape, and composition after establishing a critical temperature and molar volume. The P parameter may be estimated from known dipole moments (see, e.g., McClellan A. L., Tables of Experimental Dipole Moments (W.H. Freeman 1963)) using Equation 1:

$$\delta_P = 37.4 \text{(Dipole Moment)} / V^{1/2} \quad \text{Equation 1:}$$

where V is the molar volume. There are no equations for calculating the H parameter. Instead, the H parameter is usually determined based on group contributions.

HSP characterizations are conveniently visualized using a spherical representation, with the HSP of an experimentally-determined suitable reference solvent at the center of the sphere. The radius of the sphere (R) indicates the maximum tolerable variation from the HSP of the reference solvent that still allows for a "good" interaction to take place. Good solvents are within the sphere and bad ones are outside. The distance, $R_a$, between two solvents based on their respective HSP values can be determined using Equation 2:

$$(R_a)^2 = 4(\delta_{D1} - \delta_{D2})^2 + (\delta_{P1} - \delta_{P2})^2 (\delta_{H1} - \delta_{H2})^2 \quad \text{Equation 2:}$$

where subscript 1 indicates the reference sample, subscript 2 indicates the test chemical, and all values are in $MPa^{1/2}$. Good solubility requires that $R_a$ be less than the experimentally-determined radius of the solubility sphere $R_o$. The relative energy difference between two solvents, i.e., RED number, can be calculated by taking the ratio of $R_a$ to $R_o$, as shown in Equation 3.

$$RED = R_a / R_o \quad \text{Equation 3:}$$

RED numbers less than 1.0 indicate high affinity; RED numbers equal or close to 1.0 indicate boundary conditions; and progressively higher RED numbers indicate progressively lower affinities.

In some embodiments, the D parameters of the polar aprotic solvents of the invention are between 17.7 to 22.0 $MPa^{1/2}$. Such relatively high D parameters are generally associated with solvents having cyclic structures and/or structures with sulfur or halogens. Linear compounds are not likely to be among the most suitable solvents for use in the invention, but may be considered if their P and H parameters are within the ranges discussed below. Since the D parameter is multiplied by 4 in Equation 2, the limits are one-half of $R_o$. In addition, it should be noted that D values of around 21 or higher are often characteristic of a solid.

In some embodiments, the P parameters of the polar aprotic solvents of the invention are between 13 to 23 $MPa^{1/2}$. Such exceptionally high P paramaters are generally associated with solvents having a high dipole moment and presumably also a relatively low molecular volume. For example, for V near 60 cc/mole, the dipole moment should be between 4.5 and 3.1. For V near 90 cc/mole, the dipole moment should be between 5.6 and 3.9.

In some embodiments, the H parameters of the polar aprotic solvents of the invention are between 3 to 13 $MPa^{1/2}$. Generally, polar aprotic solvents having an alcohol group are not useful in the compositions and methods of the invention, since the H parameters of such solvents would be too high.

The molar volume of the polar aprotic solvent may also be relevant, since it enters into the evaluation of all three Hansen Solubility Parameters. As molar volume gets smaller, liquids tend to evaporate rapidly. As molar volume gets larger, liquids tend to enter the solid region in the range of D and P parameters recited above. Thus, the polar aprotic solvents of the invention are rather close to the liquid/solid boundary in HSP space.

In some embodiments, the polar aprotic solvents of the invention have lactone, sulfone, nitrile, sulfite, and/or carbonate functionality. Such compounds are distinguished by their relatively high dielectric constants, high dipole moments, and solubility in water. An exemplary polar aprotic solvent with lactone functionality is γ-butyrolactone (GBL), an exemplary polar aprotic solvent with sulfone functionality is sulfolane (SL; tetramethylene sulfide-dioxide), an exemplary polar aprotic solvent with nitrile functionality is acetonitrile (AN), an exemplary polar aprotic solvent with sulfite functionality is glycol sulfite/ethylene sulfite (GS), and an exemplary polar aprotic solvents with carbonate functionality are ethylene carbonate (EC), propylene carbonate (PC), or ethylene trithiocarbonate (ETC). The structures of these exemplary solvents are provided below and their Hansen Solubility Parameters, RED numbers, and molar volumes are given in Table 1.

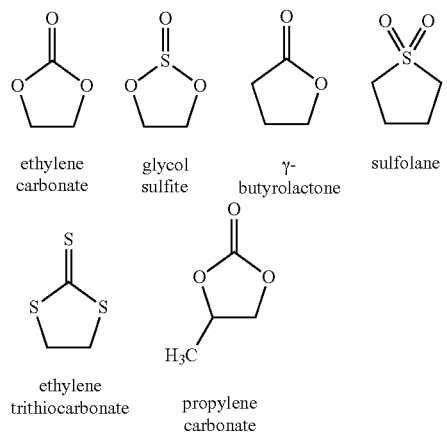

ethylene carbonate, glycol sulfite, γ-butyrolactone, sulfolane, ethylene trithiocarbonate, propylene carbonate

TABLE 1

| | D | P | H | RED | Molar Volume (cm³/mole) |
|---|---|---|---|---|---|
| Correlation ($R_0$ = 3.9) | 19.57 | 19.11 | 7.71 | — | — |
| GBL | 19.0 | 16.6 | 7.4 | 0.712 | 76.5 |
| PC | 20.0 | 18.0 | 4.1 | 0.993 | 85.2 |
| SL | 20.3 | 18.2 | 10.9 | 0.929 | 95.7 |
| EC | 19.4 | 21.7 | 5.1 | 0.946 | 66.0 |
| ETC | n/a | n/a | n/a | n/a | n/a |
| GS | 20.0 | 15.9 | 5.1 | n/a | 75.1 | n/a = not available.

Other suitable polar aprotic solvents that may be used in the invention are cyclic compounds such as, e.g., ε-caprolactone and N-methylpyrrolidone. In addition, substituted pyrolidinones and related structures with nitrogen in a 5- or 6-membered ring, and cyclic structures with two nitrile groups, or one bromine and one nitrile group, may also be suitable for use in the invention. Other suitable polar aprotic solvents may contain a ring urethane group (NHCOO—). However, not all such compounds are suitable, since 1,3-dimethyl-2-imidazolidinone produces no signals when used in the hybridization compositions of the invention. One of skill in the art may screen for compounds useful in the compositions and methods of the invention as described herein. Exemplary chemicals that may be suitable for use in the invention are set forth in Tables 2 and 3 below.

TABLE 2

| Solvent | D | P | H |
|---|---|---|---|
| Acetanilide | 20.6 | 13.3 | 12.4 |
| N-Acetyl Pyrrolidone | 17.8 | 13.1 | 8.3 |
| 4-Amino Pyridine | 20.4 | 16.1 | 12.9 |
| Benzamide | 21.2 | 14.7 | 11.2 |
| Benzimidazole | 20.6 | 14.9 | 11.0 |
| 1,2,3-Benzotriazole | 18.7 | 15.6 | 12.4 |
| Butadienedioxide | 18.3 | 14.4 | 6.2 |
| 2,3-Butylene Carbonate | 18.0 | 16.8 | 3.1 |
| Caprolactone (Epsilon) | 19.7 | 15.0 | 7.4 |
| Chloro Maleic Anhydride | 20.4 | 17.3 | 11.5 |
| 2-Chlorocyclohexanone | 18.5 | 13.0 | 5.1 |
| Chloronitromethane | 17.4 | 13.5 | 5.5 |
| Citraconic Anhydride | 19.2 | 17.0 | 11.2 |
| Crotonlactone | 19.0 | 19.8 | 9.6 |
| Cyclopropylnitrile | 18.6 | 16.2 | 5.7 |
| Dimethyl Sulfate | 17.7 | 17.0 | 9.7 |
| Dimethyl Sulfone | 19.0 | 19.4 | 12.3 |
| Dimethyl Sulfoxide | 18.4 | 16.4 | 10.2 |
| 1,2-Dinitrobenzene | 20.6 | 22.7 | 5.4 |
| 2,4-Dinitrotoluene | 20.0 | 13.1 | 4.9 |
| Dipheynyl Sulfone | 21.1 | 14.4 | 3.4 |
| 1,2-Dinitrobenzene | 20.6 | 22.7 | 5.4 |
| 2,4-Dinitrotoluene | 20.0 | 13.1 | 4.9 |
| Dipheynyl Sulfone | 21.1 | 14.4 | 3.4 |
| Epsilon-Caprolactam | 19.4 | 13.8 | 3.9 |
| Ethanesulfonylchloride | 17.7 | 14.9 | 6.8 |
| Furfural | 18.6 | 14.9 | 5.1 |
| 2-Furonitrile | 18.4 | 15.0 | 8.2 |
| Isoxazole | 18.8 | 13.4 | 11.2 |
| Maleic Anhydride | 20.2 | 18.1 | 12.6 |
| Malononitrile | 17.7 | 18.4 | 6.7 |
| 4-Methoxy Benzonitrile | 19.4 | 16.7 | 5.4 |
| 1-Methoxy-2-Nitrobenzene | 19.6 | 16.3 | 5.5 |
| 1-Methyl Imidazole | 19.7 | 15.6 | 11.2 |
| 3-Methyl Isoxazole | 19.4 | 14.8 | 11.8 |
| N-Methyl Morpholine-N-Oxide | 19.0 | 16.1 | 10.2 |
| Methyl Phenyl Sulfone | 20.0 | 16.9 | 7.8 |
| Methyl Sulfolane | 19.4 | 17.4 | 5.3 |
| Methyl-4-Toluenesulfonate | 19.6 | 15.3 | 3.8 |
| 3-Nitroaniline | 21.2 | 18.7 | 10.3 |
| 2-Nitrothiophene | 19.7 | 16.2 | 8.2 |
| 9,10-Phenanthrenequinone | 20.3 | 17.1 | 4.8 |
| Phthalic Anhydride | 20.6 | 20.1 | 10.1 |
| 1,3-Propane Sultone | 18.4 | 16.0 | 9.0 |
| beta-Propiolactone | 19.7 | 18.2 | 10.3 |
| 2-Pyrrolidone | 19.4 | 17.4 | 11.3 |
| Saccharin | 21.0 | 13.9 | 8.8 |
| Succinonitrile | 17.9 | 16.2 | 7.9 |
| Sulfanilamide | 20.0 | 19.5 | 10.7 |
| Sulfolane | 20.3 | 18.2 | 10.9 |
| 2,2,6,6-Tetrachlorocyclohexanone | 19.5 | 14.0 | 6.3 |
| Thiazole | 20.5 | 18.8 | 10.8 |
| 3,3,3-Trichloro Propene | 17.7 | 15.5 | 3.4 |
| 1,1,2-Trichloro Propene | 17.7 | 15.7 | 3.4 |
| 1,2,3-Trichloro Propene | 17.8 | 15.7 | 3.4 |

Table 2 sets forth an exemplary list of potential chemicals for use in the compositions and methods of the invention based on their Hansen Solubility Parameters. Other compounds, may of course, also meet these requirements. Some of these chemicals have been used in hybridization and/or PCR solutions in the prior art (e.g., dimethyl sulfoxide (DMSO) has been used in hybridization and PCR solutions, and sulfolane (SL) has been used in PCR solutions), but most have not. However, the prior art did not recognize that these compounds may be advantageously used to decrease hybridization times and/or temperatures, as disclosed in this application.

TABLE 3

| Chemical (dipole moment) | RED | Melting Point ° C. |
|---|---|---|
| Chloroethylene carbonate (4.02) | 0.92 | — |
| 2-Oxazolidinone (5.07) | 0.48 | 86-89 |
| 2-Imidazole | 1.49 | 90-91 |
| 1,5-Dimethyl Tetrazole (5.3) | ~1.5 | 70-72 |
| N-Ethyl Tetrazole (5.46) | ~1.5 | |
| Trimethylene sulfide-dioxide (4.49) | — | — |
| Trimethylene sulfite (3.63) | — | — |
| 1,3-Dimethyl-5-Tetrazole (4.02) | — | — |
| Pyridazine (3.97) | 1.16 | −8 |
| 2-Thiouracil (4.21) | — | — |
| N-Methyl Imidazole (6.2) | 1.28 | — |
| 1-Nitroso-2-pyrolidinone | ~1.37 | — |
| Ethyl Ethyl Phosphinate (3.51) | — | — |
| 5-cyano-2-Thiouracil (5.19) | — | — |
| 4H-Pyran-4-thione (4.08) | 1.35 | 32-34 |
| 4H-Pyran-4-one = gamma pyrone (4.08) | 1.49 | Boiling Point (BP) 80 |
| 2-Nitrofuran (4.41) | 1.14 | 29 |
| Methyl alpha Bromo Tetronate (6.24) | — | — |
| Tetrahydrothiapyran oxide (4.19) | 1.75 | 60-64 |
| Picolinonitrile (2-cyanopyridine) (5.23) | 0.40 | 26-28 (BP 212-215) |
| Nitrobenzimidazole (6.0) | 0.52 | 207-209 |
| Isatin (5.76) | — | 193-195 |
| N-phenyl sydnone (6.55) | — | — |
| Glycol sulfate (Ethylene glycol) | — | 99° C. |
| Note: not soluble at 40% | | |

Not all of the chemicals listed in Tables 2 and 3 are suitable for use in the compositions and methods of the invention. For example, although DMSO is listed in Table 2 because its Hansen Solubility Parameters (HSPs) fall within the ranges recited above, DMSO does not function to decrease hybridization times and/or temperatures in the compositions and methods of the invention. Thus, in some embodiments, the aqueous composition does not contain DMSO as a polar aprotic solvent. However, it is well within the skill of the ordinary artisan to screen for suitable compounds using the guidance provided herein including testing a compound in one of the examples provided. For example, in some embodiments, suitable polar aprotic solvents will have HSPs within the ranges recited above and a structure shown in Formulas 1-9 above.

(2) Compositions, Buffers, and Solutions
(a) Hybridization Solutions

Traditional hybridization solutions are known in the art. Such solutions may comprise, for example, buffering agents, accelerating agents, chelating agents, salts, detergents, and blocking agents.

For example, the buffering agents may include SSC, HEPES, SSPE, PIPES, TMAC, TRIS, SET, potassium phosphate, citric acid, sodium pyrrophosphate, etc. The buffering agents may be present at concentrations from 0.5× to 50×. Typically, the buffering agents are present at concentrations from 2× to 10×.

The accelerating agents may include polymers such as FICOLL, PVP, heparin, dextran sulfate, proteins such as BSA, glycols such as ethylene glycol, glycerol, 1,3 propanediol glycerol, propylene glycol, or diethylene glycol, combinations thereof such as Dernhardt's solution and BLOTTO, and organic solvents such as formamide, dimethylformamide, DMSO, etc. The accelerating agent may be present at concentrations from 1% to 80% or 0.1× to 10×. Typically, formamide is present at concentrations from 25% to 75%, while DMSO, dextran sulfate, and glycol are present at concentrations from 5% to 10%.

The chelating agents may include EDTA, EGTA, etc. The chelating agents may be present at concentrations from 0.1 mM to 10 mM. Typically, the chelating agents are present at concentrations from 0.5 mM to 5 mM.

The salts may include sodium chloride, sodium phosphate, magnesium phosphate, etc. The salts may be present at concentrations from 1 mM to 750 mM. Typically, the salts are present at concentrations from 10 mM to 500 mM.

The detergents may include Tween, SDS, Triton, CHAPS, deoxycholic acid, etc. The detergent may be present at concentrations from 0.01% to 10%. Typically, the detergents are present at concentrations from 0.1% to 1%.

The nucleic acid blocking agents may include, yeast tRNA, homopolymer DNA, denatured salmon sperm DNA, herring sperm DNA, total human DNA, COT1 DNA, etc.

The blocking nucleic acids may be present at concentrations of 0.05 mg/mL to 100 mg/mL.

A great variation exists in the literature regarding traditional hybridization solutions. For example, a traditional hybridization solution may comprise 5× or 6×SSC, 0.01 M EDTA, 5×Dernhardt's solution, 0.5% SDS, and 100 mg/mL sheared, denatured salmon sperm DNA. Another traditional hybridization solution may comprise 50 mM HEPES, 0.5 M NaCl, and 0.2 mM EDTA. A typical hybridization solution for FISH on biological specimens for RNA detection may comprise, e.g., 2×SSC, 10% dextran sulfate, 2 mM vanadyl-ribonucleoside complex, 50% formamide, 0.02% RNAse-free BSA, and 1 mg/mL E. coli tRNA. A typical hybridization solution for FISH on biological specimens for DNA detecttion may comprise, e.g., 2×SSC, 10% dextran sulfate, 50% formamide, and e.g., 0.3 mg/mL salmon sperm DNA or 0.1 mg/mL COT1 DNA. Other typical hybridization solutions may comprise 40% formamide, 10% dextran sulfate, 30 mM NaCl, 5 mM phosphate buffer, blocking-PNA or COT-1 DNA, and in some cases 0.1 μg/μL total human DNA (THD).

The compositions of the invention may comprise a hybridization solution comprising any of the components of traditional hybridization solutions recited above in combination with at least one polar aprotic solvent. The traditional components may be present at the same concentrations as used in traditional hybridization solutions, or may be present at higher or lower concentrations, or may be omitted completely.

For example, if the compositions of the invention compriseNaCl and/or phosphate buffer, they may be present at concentrations of 0-1200 mM NaCl and/or 0-200 mM phosphate buffer. In some embodiments, the concentrations of salts may be, for example, 300 mM NaCl and 5 mM phosphate buffer, or 600 mM NaCl and 10 mM phosphate buffer.

If the compositions of the invention comprise accelerating agents such as dextran sulfate, glycol, or DMSO, the dextran sulfate may be present at concentrations of from 5% to 40%, the glycol may be present at concentrations of from 0.1% to 10%, and the DMSO may be from 0.1% to 10%. In some embodiments, the concentration of dextran sulfte may be 10% or 20% and the concentration of ethylene glycol, 1,3 propanediol, or glycerol may be 1% to 10%. In some embodiments, the concentration of DMSO may be 1%. In some embodiments, the aqueous composition does not comprise DMSO as an accelerating agent. In some embodiments, the aqueous composition does not comprise formamide as an accelerating agent, or comprises formamide with the proviso that the composition contains less than 10%, or less than 5%, or less than 2%, or less than 1%, or less than 0.5%, or less than 0.1%, or less than 0.05%, or less than 0.01%.

If the compositions of the invention comprise citric acid, the concentrations may range from 1 mM to 50 mM and the pH may range from 5.0 to 8.0. In some embodiments the concentration of citric acid may be 10 mM and the pH may be 6.2.

The compositions of the invention may comprise agents that reduce non-specific binding to, for example, the cell membrane, such as salmon sperm or small amounts of total human DNA or, for example, they may comprise blocking agents to block binding of, e.g., repeat sequences to the target such as larger amounts of total human DNA or repeat enriched DNA or specific blocking agents such as PNA or LNA fragments and sequences. These agents may be present at concentrations of from 0.01-100 μg/μL or 0.01-100 μM. For example, in some embodiments, these agents will be 0.1 μg/μL total human DNA, or 0.1 μg/μL non-human DNA, such as herring sperm, salmon sperm, or calf thymus DNA, or 5 μM blocking PNA.

One aspect of the invention is a composition or solution for use in hybridization. Compositions for use in the invention include an aqueous composition comprising a nucleic acid sequence and at least one polar aprotic solvent in an amount effective to denature double-stranded nucleotide sequences. An amount effective to denature double-stranded nucleotide sequences is an amount that enables hybridization. For example, one way to test for whether the amount of polar aprotic solvent is effective to enable hybridization is to determine whether the polar aprotic solvent, when used in the hybridization methods and compositions described herein, such as example 1, yield a detectable signal and/or an amplified nucleic acid product.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, or 50% to 60% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

Where one or more nucleic acid probes are present in the compositions of the invention, the probes may be directly or indirectly labeled with detectable compounds (such as, e.g., enzymes, chromophores, fluorochromes, and haptens), as described supra. The DNA probes may be present at concentrations of 0.1 to 100 ng/μL. For example, in some embodiments, the probes may be present at concentrations of 1 to 10 ng/μL. The PNA probes may be present at concentrations of 0.5 to 5000 nM. For example, in some embodiments, the probes may be present at concentrations of 5 to 1000 nM.

In one embodiment, a composition of the invention comprises a mixture of 40% polar aprotic solvent (v/v) (e.g., ethylene carbonate, "EC"), 10% dextran sulfate, 300 mM NaCl, 5 mM phosphate buffer, and 1-10 ng/μL probe. Another exemplary composition of the present invention comprises a mixture of 15% EC, 20% dextran sulfate, 600 mM NaCl, 10 mM phosphate buffer, and 0.1 μg/μl total human DNA. Yet another exemplary composition comprises 15% EC, 20% dextran sulfate, 600 mM NaCl, 10 mM citric acid pH 6.2, and 0.1 μg/μL non-human DNA (e.g., herring sperm, salmon sperm, or calf thymus) OR 0.5% formamide OR 1% glycol (e.g., ethylene glycol, 1,3 propanediol, or glycerol).

(b) Polar Aprotic Solvent(s)

Different polar aprotic solvents may impart different properties on the compositions of the invention. For example, the choice of polar aprotic solvent may contribute to the stability of the composition, since certain polar aprotic solvents may degrade over time. For example, the polar aprotic solvent ethylene carbonate breaks down into ethylene glycol, which is a relatively stable molecule, and carbon dioxide, which can interact with water to form carbonic acid, altering the acidity of the compositions of the invention. Without being bound by theory, it is believed that the change in pH upon breakdown of ethylene carbonate makes the compositions of the invention less effective for hybridization. However, stability can be improved by reducing the pH of the composition, by adding citric acid as a buffer at pH 6.2 instead of the traditional phosphate buffer, which is typically used at about pH 7.4, and/or by adding ethylene glycol at concentrations, e.g., between 0.1% to 10%, or between 0.5% to 5%, such as, for example, 1%, 2%, 3%, etc. For example, with 10 mM citrate buffer, the compositions of the invention are stable at 2-8° C. for approximately 8 months. Stability can also be improved if the compositions are stored at low temperatures (e.g., −20° C.).

In addition, certain polar aprotic solvents may cause the compositions of the invention to separate into multi-phase systems under certain conditions. The conditions under which multi-phase systems are obtained may be different for different polar aprotic solvents. Generally, however, as the concentration of polar aprotic solvent increases, the number of phases increases. For example, compositions comprising low concentrations ethylene carbonate (i.e., less than 20%) may exist as one phase, while compositions comprising higher concentrations of ethylene carbonate may separate into two, or even three phases. For instance, compositions comprising 15% ethylene carbonate exist as a single phase at room temperature, while compositions comprising 40% ethylene carbonate consist of a viscous lower phase (approximately 25% of the total volume) and a less viscous upper phase (approximately 75% of the total volume) at room temperature.

On the other hand, some polar aprotic solvents may exist in two phases at room temperature even at low concentrations. For example, sulfolane, γ-butyrolactone, ethylene trithiocarbonate, glycol sulfite, and propylene carbonate exist as two phases at concentrations of 10, 15, 20, or 25% (20% dextran sulfate, 600 mM NaCl, 10 mM citrate buffer) at room temperature.

It may also be possible to alter the number of phases by adjusting the temperature of the compositions of the invention. Generally, as temperature increases, the number of phases decreases. For example, at 2-8° C., compositions comprising 40% ethylene carbonate may separate into a three-phase system.

It may also be possible to alter the number of phases by adjusting the concentration of dextran sulfate and/or salt in the composition. Generally speaking, lowering the dextran sulfate concentration (traditional concentration is 10%) and/or salt concentration may reduce the number of phases. However, depending on the particular polar aprotic solvent and its concentration in the composition, single phases may be produced even with higher concentrations of salt and dextran sulfate. For example, a composition comprising low amounts of EC (e.g., 15%, 10%, 5%) can work well by increasing the dextran sulfate and salt concentrations, while still keeping a one phase system. In a particular embodiment, compositions comprising a HER2 gene DNA probe, a CENT PNA probe, 15% EC, 20% dextran sulfate, 600 mM NaCl, and 10 mM phosphate buffer exist as one phase even at −20° C. In other embodiments, the compositions are liquid at −20° C.

Some polar aprotic solvents may produce stronger signals in one phase or another. For example, 40% glycol sulfite produces strong signals in the lower phase and no signals in the upper phase. Similarly, certain types of probes may produce stronger signals in one phase or another. For example, PNA probes tend to show stronger signals in the lower phase than the upper phase.

Accordingly, the multiphase systems of the invention may be used to conveniently examine different aspects of a sample. For example, a two-phase system could be used to separate samples labeled with PNA probes from samples labeled with DNA probes. Other uses include isolation of a specific phase exhibiting, e.g., certain hybridization advantages such that the isolated phase can be used as a single phase system. The probe and/or sample may be added prior to, or after isolation of a particular phase.

Hybridizations may be performed with a one-phase composition of the invention, with individual phases of the multiphase compositions of the invention, or with mixtures of any one or more of the phases in a multiphase composition of the invention. For example, in a one phase system, a volume of the sample may be extracted for use in the hybridization. In a mulitphase system, one may extract a volume of sample from the phase of interest (e.g., the upper, lower, or middle phase) to use in the hybridization. Alternatively, the phases in a multiphase system may be mixed prior to extracting a volume of the mixed sample for use in the hybridization. However, the multiphase system may yield strong and uneven local background staining depending on the composition. While, the addition of low amounts of formamide will reduce background in a one phase system, it has little effect on a multiphase system with high concentrations (e.g., 40%) of a polar aprotic solvent. In addition, as the concentration of formamide increases, higher concentrations of probe and/or longer hybridization times are required to maintain strong signal intensity.

(c) Optimization for Particular Applications

The compositions of the invention can be varied in order to optimize results for a particular application. For example, the concentration of polar aprotic solvent, salt, accelerating agent, blocking agent, and hydrogen ions (i.e. pH) may be varied in order to improve results for a particular application.

For example, the concentration of polar aprotic solvent may be varied in order to improve signal intensity and background staining. Generally, as the concentration of polar aprotic solvent increases, signal intensity increases and background staining decreases. For example, compositions comprising 15% EC tend to show stronger signals and less background than compositions comprising 5% EC. However, signal intensity may be improved for compositions having low concentrations of polar aprotic solvent (e.g., 0% to 20%) if the concentrations of salt and/or dextran sulfate are increased. For example, strong signals may be observed with 5% to 10% EC when the salt concentration is raised approximately 8 to 16 times traditional salt concentrations (i.e., approximately 1200 mM NaCl, 20 mM phosphate buffer). Likewise, as lower concentrations of polar aprotic solvent are used, higher concentrations of dextran sulfate are generally required to maintain good signal and background intensity.

Accordingly, the concentrations of salt and dextran sulfate may also be varied in order to improve signal intensity and background staining. Generally, as the concentrations of salt and dextran sulfate increase, the signal intensity increases and background decreases. For example, salt concentrations that are approximately two to four times traditional concentrations (i.e., 300 mM NaCl 5 mM phosphate buffer) produce strong signals and low background. Surprisingly, however, hybridization occurs using the compositions of the invention even in the complete absence of salt. Signal intensities can be improved under no-salt conditions by increasing the concentrations of accelerating agent and/or polar aprotic solvent.

Likewise, signal intensity increases as dextran sulfate concentration increases from 0% to 20%. However, good signals may even be observed at dextran sulfate concentrations of 0%. Signal intensity may be improved under low dextran sulfate conditions by increasing the polar aprotic solvent and/or salt concentrations.

In addition, the types probes used in the compositions of the invention may be varied to improve results. For example, in some aspects of the invention, combinations of DNA/DNA probes may show less background than combinations of DNA/PNA probes in the compositions of the invention or vice versa. On the other hand, PNA probes tend to show stronger signals than DNA probes under low salt and/or low polar aprotic solvent concentrations. In fact, PNA probes also show signals when no polar aprotic solvent is present, whereas DNA probes show weak or no signals without polar aprotic solvent.

II. Kits

The present invention also provides kits comprising compositions of the invention. Thus, a kit may comprise one or more molecular probes (as elaborated supra) and an aqueous composition (as elaborated supra). In one embodiment, the probe is not readily visualized (e.g., because it is not labeled with a fluorophore or chromophore), and the kit further comprises a visualization reagent, such as, e.g., an antibody (which may be monoclonal, and which may be labeled with a detectable label), a fluorogenic or chromogenic enzyme substrate, a streptavidin conjugate, or any other suitable visualization reagent known to the skilled artisan.

In one embodiment, the kit further comprises other reagents and/or compositions that may be used to detect a chromosomal aberration. In one embodiment, a kit may further comprise a protease, such as, e.g., pepsin or proteinase K. In one embodiment, a kit may further comprise one or more of a pre-treatment solution, protease, stringent wash buffer, fluorescence mounting medium, wash buffer, signal amplification solution, and coverslip sealant. For example, in one embodiment, a cytology FISH kit may further comprise one or more of wash buffer, stringency buffer, fluorescence mounting medium, and coverslip sealant. In one embodiment, a histology FISH kit may further comprise one or more of pre-treatment solution, pepsin, wash buffer, stringency buffer, fluorescence mounting medium, and coverslip sealant. In one embodiment, a CISH kit may further comprise peroxidase block, CISH antibody mix, a red substrate buffer, a blue substrate buffer, a red chromogen, and a blue chromogen. In another embodiment, a kit may further comprise instructions.

III. Applications, Methods and Uses

The invention further provides methods of using the compositions and kits described above for detection of chromosomal aberrations, diagnosis of disease, monitoring progress of therapeutic treatment, monitoring a patient who has completed treatment for recurrence of disease. In general, such methods use one or more of the hybridization conditions described infra.

For example, the invention provides a method of detecting a chromosomal aberration using compositions of the invention. Detection may be relevant to diagnosis, selection of an appropriate treatment, and/or monitoring of a patient for disease recurrence. In one embodiment, the invention provides a method of determining whether a chromosomal aberration is present in a nucleic acid sequence, the method comprising:

providing a molecular probe that detects the chromosomal aberration,
providing the nucleic acid sequence,
providing an aqueous composition comprising 1% (v/v) to 95% (v/v) of at least one polar aprotic solvent,
combining the molecular probe and the nucleic acid sequence and the aqueous composition for at least a time period sufficient to hybridize the molecular probe and the nucleic acid sequence, and
determining whether the molecular probe has hybridized to the nucleic acid sequence,
thereby determining whether the chromosomal aberration is present in the nucleic acid sequence.

In another embodiment, the invention provides a method of determining whether a chromosomal aberration is present in a nucleic acid sequence, the method comprising:

providing the nucleic acid sequence,
applying an aqueous composition comprising a molecular probe that detects the chromosomal aberration and 1% (v/v) to 95% (v/v) of at least one polar aprotic solvent to said nucleic acid for at least a time period sufficient to hybridize the molecular probe and nucleic acid sequence, and
determining whether the molecular probe has hybridized to the nucleic acid sequence,
thereby determining whether the chromosomal aberration is present in the nucleic acid sequence.

In another embodiment, the invention provides a method of determining whether a chromosomal aberration is present in a nucleic acid sequence, the method comprising:

providing the nucleic acid sequence,
applying an aqueous composition of the invention comprising at least one polar aprotic solvent and a molecular probe that detects the chromosomal aberration to said nucleic acid sequence for at least a time period sufficient to hybridize the molecular probe and nucleic acid sequence, and
determining whether the molecular probe has hybridized to the nucleic acid sequence,
thereby determining whether the chromosomal aberration is present in the nucleic acid sequence.

The invention further provides a method of diagnosing a congenital genetic disorder, cancer, or infection associated with a chromosomal aberration, providing a tissue sample from a subject, wherein the tissue sample comprises a nucleic acid sequence,
determining whether a chromosomal aberration is present in a nucleic acid sequence, according to the methods of the invention, and
diagnosing the congenital genetic disorder, cancer, or infection if the chromosomal aberration is present in the tissue sample.

In one embodiment, the methods of the invention may be used to determine whether a patient would benefit from a particular treatment. For example, a breast cancer patient in whom HER2 is amplified may benefit from treatment with Herceptin™ (trastuzumab) and a colorectal cancer patient in whom EGFR is overexpressed may benefit from treatment with Erbitux® (cetuximab) or Vectibix™ (panitumumab).

In one embodiment, the methods of the invention may be used to monitor disease progression or remission. In another embodiment, the methods of the invention may be used to assess a patient's prognosis. For example, the methods of the invention may be used, together with clinicopathologic data, to assess a patient's prognosis. In one embodiment, the methods may be used determine the presence of HER2 gene amplification, and to use that information to provide a prognosis for a stage II, node-positive breast cancer patient. The presence of TOP2A deletions or amplifications may also be used to assess prognosis of breast cancer patients.

A. Analytical Samples

The methods and compositions of the invention may be used fully or partly in all types of hybridization applications in the fields of cytology, histology, or molecular biology.

According to one embodiment, the first or the second nucleic acid sequence in the methods of the invention is present in a biological sample. Examples of such samples include, tissue samples, cell preparations, cell fragment preparations, and isolated or enriched cell component preparations. The sample may originate from various tissues such as, e.g., breast, lung, colorectal, prostate, lung, head & neck, stomach, pancreas, esophagus, liver, and bladder, or other relevant tissues and neoplasia thereof, any cell suspension, blood sample, fine needle aspiration, ascites fluid, sputum, peritoneum wash, lung wash, urine, faeces, cell scrape, cell smear, cytospin or cytoprep cells.

The sample may be isolated and processed using standard protocols. Cell fragment preparations may, e.g., be obtained by cell homogenizing, freeze-thaw treat-ment or cell lysing. The isolated sample may be treated in many different ways depending on the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixed followed by paraffin-embedding and cryo-preservation.

Cytology involves the examination of individual cells and/or chromosme spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells are then fixed on the microscope slide before analysis by any of the techniques discussed below.

For metaphase spreads, cell cultures are generally treated with colcemid, or anther suitable spindle pole disrupting agent, to stop the cell cycle in metaphase. The cells are then fixed and spotted onto microscope slides, treated with formaldehyde, washed, and dehydrated in ethanol. Probes are then added and the samples are analyzed by any of the techniques discussed below.

In a traditional hybridization experiment using a cytological sample, slides containing the specimen are immersed in a formaldehyde buffer, washed, and then dehydrated in ethanol. The probes are then added and the specimen is covered with a coverslip. The slide is incubated at a temperature sufficient to denature any nucleic acid in the specimen (e.g. 5 minutes at 82° C.) and then incubated at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

Histology involves the examination of cells in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixatives, and then infused with dehydrating reagent prior to analysis of the sample.

In a traditional hybridization experiment using a histological sample, formalin-fixed paraffin embedded tissue specimens are cut into sections of 2-6 μm and collected on slides. The paraffin is melted (e.g., 30-60 minutes at 60° C.) and then removed (deparaffinated) by washing with xylene (or a xylene substitute), e.g., 2×5 mintes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip and the slide is incubated at a temperature sufficient to denature any nucleic acid in the specimen (e.g. 5 minutes at 82° C.), followed by incubation at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

B. Hybridization Techniques

The compositions and methods of the present invention can be used fully or partly in all types of nucleic acid hybridization techniques known in the art for cytological and histological samples. Such techniques include, for example, in situ hybridization (ISH), fluorescent in situ hybridization (FISH; including multi-color FISH, Fiber-FISH, etc.), chromogenic in situ hybridization (CISH), silver in situ hybridization (SISH), comparative genome hybridization (CGH), chromosome paints, and arrays in situ.

In general, hybridization techniques such as CGH, FISH, CISH, and SISH, employ large, mainly unspecified, nucleic acid probes that hybridize with varying stringency to genes or gene fragments in the chromosomes of cells. Such probes may be derived from cosmic clones, YAC clones, or other cloned DNA fragments. Using large probes renders the in situ hybridization technique very sensitive. However, the successful use of large genomic probes in traditional hybridization assays depends on blocking the undesired background staining derived from, e.g., repetitive sequences that are present throughout the genome. Such blocking steps are time-consuming and expensive. As discussed herein, the methods and compositions of the invention advantageously reduce and/or eliminate the need for such blocking steps. However, in one embodiment, repetitive sequences may be suppressed according to the methods known in the art, e.g., as disclosed in PCT/US02/30573.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLD-FISH). Thus, depending on the method of detection, populations of cells obtained from a sample to be tested may be visualized via fluorescence microscopy or conventional brightfield light microscopy.

Hybridization assays on cytological and histological samples are important tools for determining the number, size, and/or location of specific DNA sequences. For example, in CGH, whole genomes are stained and compared to normal reference genomes for the detection of regions with aberrant copy number. Typically, DNA from subject tissue and from normal control tissue is labeled with different colored probes. The pools of DNA are mixed and added to a metaphase spread of normal chromosomes (or to a microarray chip, for array- or matrix-CGH). The ratios of colors are then compared to identify regions with aberrant copy number.

FISH is typically used when multiple color imaging is required and/or when the protocol calls for quantification of signals. The technique generally entails preparing a cytological sample, labeling probes, denaturing target chromosomes and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. DNA sequences ranging from whole genomes down to several kilobases can be studied using FISH. FISH may also be used on metaphase spreads and interphase nuclei.

FISH has been used successfully for mapping repetitive and single-copy DNA sequences on metaphase chromosomes, interphase nuclei, chromatin fibers, and naked DNA molecules, and for chromosome identification and karyotype analysis through the localization of large repeated families, typically the ribosomal DNAs and major tandem array families. One of the most important applications for FISH has been in detecting single-copy DNA sequences, in particular disease related genes in humans and other eukaryotic model species, and the detection of infections agents. FISH may be used to detect, e.g., chromosomal aneuploidy in prenatal diagnoses, hematological cancers, and solid tumors; gene abnormalities such as oncogene amplifications, gene deletions, or gene fusions; chromosomal structural abnormalities such as translocatoins, duplications, insertions, or inversions; contiguous gene syndromes such as microdeletion syndrome; the genetic effects of various therapies; viral nucleic acids in somatic cells and viral integration sites in chromosomes; etc.

In multi-color FISH, each chromosome is stained with a separate color, enabling one to determine the normal chromosomes from which abnormal chromosomes are derived. Such techniques include multiplex FISH (m-FISH; Speicher et al. *Nat. Genet.*, 12:368-75 (1996)), spectral karyotyping (SKY; Schrock et al., Science, 273:494-97 (1996)), combined binary ration labeling (COBRA; Tanke et al., Eur. J. Hum. Genet., 7:2-11 (1999)), color-changing karyotyping (Henegariu et al., Nat. Genet., 23:263-64 (1999)), cross-species color banding (Muller et al., Hum. Genet., 100:271-78 (1997)), high resolution multicolor banding (Chudoba et al., Cytogenet. Cell Genet., 84:156-60 (1999)), telomeric multiplex FISH (TM-FISH; Henegariu et al., Lab. Invest., 81:483-91 (2001)), split-signal FISH (ssFISH), and fusion-signal FISH. CISH and SISH may be used for many of the same applications as FISH, and have the additional advantage of allowing for analysis of the underlying tissue morphology, for example in histopathology applications.

The compositions of the invention may also be used fully or partly in all types of molecular biology techniques involving hybridization, including blotting and probing (e.g., Southern, northern, etc.), arrays, and amplification techniques including traditional PCR, RT-PCR, mutational PCR, asymmetric PCR, hot-start PCR, inverse PCR, multiplex PCR, nested PCR, quantitiative PCR, and in situ PCR. In situ PCR is a polymerase chain reaction that takes place inside a cell on a slide, e.g., the cytology and histology samples described above. Typically, after adhering the sample to a microscope slide, the cells are re-hydrated and permeabilized, and then combined with an appropriate mixture of PCR reagents including polymerase, dNTPs, and primers. The PCR may be carried out in a dedicated instrument, such as the GeneAmp In situ PCR System 1000 (Perkin Elmer Biosystems, Foster City, CA), and the amplified product may be detected using labeled probes or by incorporating labeled dNTPs during the amplification. The compositions of the invention will improve the efficiency of traditional and in situ PCR analysis, e.g., by reducing the denaturation and hybridization temperatures and/or the time required in order to run the amplication cycles.

C. Hybridization Conditions

Hybridization methods using the compositions of the invention may involve applying the compositions to a sample comprising a target nucleic acid sequence, most likely in a double stranded form. Usually, in order to secure access for the probe to hybridize with the target sequence, the sample and composition are heated to denature the target nucleic acids. During denaturation the polar aprotic solvent interacts with the sequence and facilitates the denaturation of the target and the re-annealing of the probe to target. The polar aprotic solvents specified in the present invention speed up this process considerably and reduce the harshness and toxicity of the hybridization conditions compared to formamide.

Hybridizations using the compositions of the invention may be performed using the same assay methodology as for hybridizations performed with traditional solutions. However, the compositions of the invention allow for shorter hybridization times. For example, the heat pre-treatment, digestion, denaturation, hybridization, washing, and mounting steps may use the same conditions in terms of volumes, temperatures, reagents and incubation times as for traditional solutions. A great variation exists in the traditional hybridization protocols known in the art. For example, some protocols specify a separate denaturation step of potential double stranded nucleotides without probe present, before the following hybridization step. The compositions of the invention may be used in any of traditional hybridization protocols known in the art.

Alternatively, assays using the compositions of the invention can be changed and optimized from traditional methodologies, for example, by decreasing the hybridization time, increasing or decreasing the denaturation and/or hybridization temperatures, and/or increasing or decreasing the hybridization volumes.

For example, in some embodiments, the compositions of the invention will produce strong signals when the denaturation temperature is from 60 to 100° C. and the hybridization temperature is from 20 to 60° C. In other embodiments, the compositions of the invention will produce strong signals when the denaturation temperature is from 60 to 70° C., 70 to 80° C., 80 to 90° C. or 90 to 100° C., and the hybridization temperture is from 20 to 30° C., 30 to 40° C., 40 to 50° C., or 50 to 60° C. In other embodiments, the compositions of the invention will produce strong signals when the denaturation temperature is 72, 82, or 92° C., and the hybridization temperature is 40, 45, or 50° C.

In other embodiments, the compositions of the invention will produce strong signals when the denaturation time is from 0 to 10 minutes and the hybridization time is from 0 minutes to 24 hours. In other embodiments, the compositions of the invention will produce strong signals when the denaturation time is from 0 to 5 minutes and the hybridization time is from 0 minutes to 8 hours. In other embodiments, the compositions of the invention will produce strong signals when the denaturation time is 0, 1, 2, 3, 4, or 5 minutes, and the hybridization time is 0 minutes, 5 minutes, 15 minutes, 30 minutes, 60 minutes, 180 minutes, or 240 minutes. It will be understood by those skilled in the art that in some cases, e.g., RNA detection, a denaturation step is not required.

Figure 2:
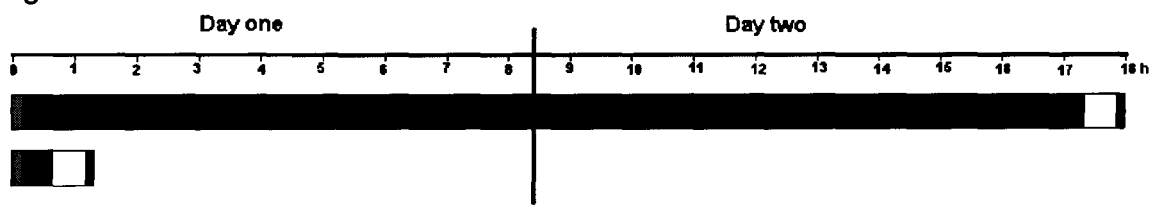
FIG. 2 depicts a typical time-course for single locus detection with primary labeled FISH probes on cytological specimens. The bars represent a hybridization performed using a traditional solution (top) and a typical time-course for a hybridization performed using a composition of the invention (bottom). The first bar on the left in each time-course represents the fixation step; the second bar represents the denaturation and hybridization step; the third bar represents the stringency wash step; and the fourth bar represents the mounting step.

Accordingly, hybridizations using the compositions of the invention may be performed in less than 8 hours. In other embodiments, the hybridization is performed in less than 6 hours. In still other embodiments, the hybridization is performed within 4 hours. In other embodiments, the hybridization is performed within 3 hours. In yet other embodiments, the hybridization is performed within 2 hours. In other embodiments, the hybridization is performed within 1 hour. In still other embodiments, the hybridization is performed within 30 minutes. In other embodiments, they hybridization can take place within 15 minutes. The hybridization can even take place within 10 minutes or in less than 5 minutes. FIGS. 1 and 2 illustrate a typical time-course for hybridizations performed on histological and cytological samples, respectively, using the compositions of the invention compared to hybridizations using a traditional solutions.

As hybridization time changes, the concentration of probe may also be varied in order to produce strong signals and/or reduce background. For example, as hybridization time decreases, the amount of probe may be increased in order to improve signal intensity. On the other hand, as hybridization time decreases, the amount of probe may be decreased in order to improve background staining.

The compositions of the invention surprisingly eliminate the need for a blocking step during hybridization by improving signal and background intensity by blocking the binding of, e.g., repetitive sequences to the target DNA. Thus, there is no need to use total human DNA, blocking-PNA, COT-1 DNA, or DNA from any other source as a blocking agent. However, background levels can be further reduced by adding agents that reduce non-specific binding, such as to the cell membrane, such as small amounts of total human DNA or non-human-origin DNA (e.g., salmon sperm DNA) to a hybridization reaction using the compositions of the invention.

The aqueous compositions of the invention furthermore provide for the possibility to considerably reduce the concentration of nucleic acid sequences included in the composition. Generally, the concentration of probes may be reduced from 2 to 8-fold compared to traditional concentrations. For example, if HER2 DNA probes and CEN17 PNA probes are used in the compositions of the invention, their concentrations may be reduced by ¼ and ½, respectively, compared to their concentrations in traditional hybridization solutions. This feature, along with the absence of any requirement for blocking DNA, such as blocking-PNA or COT1, allows for an increased probe volume in automated instrument systems compared to the traditional 10 µL volume used in traditional composition systems, which reduces loss due to evaporation, as discussed in more detail below.

Reducing probe concentration also reduces background. However, reducing the probe concentration is inversely related to the hybridization time, i.e., the lower the concentration, the higher hybridization time required. Nevertheless, even when extremely low concentrations of probe are used with the aqueous compositions of the invention, the hybridization time is still shorter than with traditional solutions.

The compositions of the invention often allow for better signal-to-noise ratios than traditional hybridization solutions. For example, with certain probes, a one hour hybridization with the compositions of the invention will produce similar background and stronger signals than an overnight hybridization in a traditional solutions. Background is not seen when no probe is added.

Traditional assay methods may also be changed and optimized when using the compositions of the invention depending on whether the system is manual, semi-automated, or automated. For example, a semi- or an automated system will benefit from the short hybridization times obtained with the compositions of the invention. The short hybridization time may reduce the difficulties encountered when traditional solutions are used in such systems. For example, one problem with semi- and automated systems is that significant evaporation of the sample can occur during hybridization, since such systems require small sample volumes (e.g., 10-150 µL), elevated temperatures, and extended hybridization times (e.g., 14 hours). Thus, the proportions of the components in traditional hybridization solutions are fairly invariable. However, since the compositions of the invention allow for faster hybridizations, evaporation is reduced, allowing for increased flexibility in the proportions of the components in hybridization compositions used in semi- and automated systems.

For example, two automated instruments have been used to perform hybridizations using the compositions of the invention. Compositions comprising 40% ethylene carbonate have been used in the apparatus disclosed in PCT application DK2008/000430, and compositions comprising 15% ethylene carbonate have been used in the HYBRIMASTER HS-300 (Aloka CO. LTD, Japan). When the compositions of the invention are used in the HYBRIMASTER HS-300, the instrument can perform rapid FISH hybridization with water in place of the traditional toxic formamide mix, thus improving safety and reducing evaporation. If water wetted strips are attached to the lid of the inner part of the Aloka instrument's reaction unit (hybridization chamber) as described in U.S. Patent Application Pub. No. 2005/0281711, evaporation is reduced even further.

Another problem with automated imaging analysis is the number of images needed, the huge amount of storage place required, and the time required to take the images. The compositions of the invention address this problem by producing very strong signals compared to traditional solutions. Because of the very strong signals produced by the compositions of the invention, the imaging can be done at lower magnification than required for traditional solutions and can still be detected and analyzed, e.g., by algorithms. Since the focal plane becomes wider with lower magnification, the compositions of the invention reduce or eliminate the requirement to take serial sections of a sample. As a result, the overall imaging is much faster, since the compositions of the invention require fewer or no serial sections and each image covers much greater area. In addition, the overall time for analysis is faster, since the total image files are much smaller.

Thus, the compositions and methods of the invention solve many of the problems associated with traditional hybridization solutions and methods.

The disclosure may be understood more clearly with the aid of the non-limiting examples that follow, which constitute preferred embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements. The examples that follow illustrate the present invention and should not in any way be considered as limiting the invention.

EXAMPLES

Reference will now be made in detail to specific embodiments of the invention. While the invention will be described in conjunction with these embodiments, it will be understood that they are not intended to limit the invention to those embodiments. On the contrary, the invention is intended to cover alternatives, modifications, and equivalents, which may be included within the invention as defined by the appended claims.

The reagents used in the following examples are from Dako's Histology FISH Accessory Kit (K5599) and Cytology FISH Accessory Kit (K5499) (Dako Denmark A/S, Glostrup Denmark). The kits contain all the key reagents, except for probe, required to complete a FISH procedure for formalin-fixed, paraffin-embedded tissue section specimens. All samples were prepared according to the manufacturer's description. The Dako Hybridizer (S2450, Dako) was used for the digestion, denaturation, and hybridization steps.

Evaluation of FISH slides was performed within a week after hybridization using a Leica DM6000B fluorescence microscope, equipped with DAPI, FITC, Texas Red single filters and FITC/Texas Red double filter under 10×, 20×, 40×, and 100× oil objective.

Evaluation of CISH slides was performed using an Olympus BX51 light microscope, under 4×, 10×, 20×, 40×, and 60× objective.

In the Examples that follow, "dextran sulfate" refers to the sodium salt of dextran sulfate (D8906, Sigma) having a molecular weight $M_w$>500,000. All concentrations of polar aprotic solvents are provided as v/v percentages. Phosphate buffer refers to a phosphate buffered solution containing $NaH_2PO_4$, $2H_2O$ (sodium phosphate dibasic dihydrate) and $Na_2HPO_4$, $H_2O$ (sodium phosphate monobasic monohydrate). Citrate buffer refers to a citrate buffered solution containing sodium citrate ($Na_3C_6H_5O_7$, $2H_2O$; 1.06448, Merck) and citric acid monohydrate ($C_6H_8O_7$, $H_2O$; 1.00244, Merck).

General Histology FISH/CISH Procedure (Examples 1-20)

The slides with cut formalin-fixed paraffin embedded (FFPE) multiple tissue array sections from humans (tonsils, mammacarcinoma, kidney and colon) were baked at 60° C. for 30-60 min, deparaffinated in xylene baths, rehydrated in ethanol baths and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then incubated with 10 μL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity, morphology, and background of the stained slides performed the scoring.

General Cytology FISH Procedure (Examples 21-22)

Slides with metaphases preparation were fixed in 3.7% formaldehyde for 2 min, washed 2×5 min, dehydrated in a series of ethanol evaporations, and air-dried. The samples were then incubated with 10 μL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity and background of the stained slides performed the scoring as described in the scoring for guidelines for tissue sections.

Scoring Guidelines of Tissue Sections

The signal intensities were evaluated on a 0-3 scale with 0 meaning no signal and 3 equating to a strong signal. The cell/tissue structures are evaluated on a 0-3 scale with 0 meaning no structure and no nuclei boundaries and 3 equating to intact structure and clear nuclei boundaries. Between 0 and 3 there are additional grades 0.5 apart from which the observer can assess signal intensity, tissue structure, and background.

The signal intensity is scored after a graded system on a 0-3 scale.

0 No signal is seen.
1 The signal intensity is weak.
2 The signal intensity is moderate.
3 The signal intensity is strong.
The scoring system allows the use of ½ grades.

The tissue and nuclear structure is scored after a graded system on a 0-3 scale.

0 The tissue structures and nuclear borders are completely destroyed.
1 The tissue structures and/or nuclear borders are poor. This grade includes situations where some areas have empty nuclei.
2 Tissue structures and/or nuclear borders are seen, but the nuclear borders are unclear. This grade includes situations where a few nuclei are empty.
3 Tissue structures and nuclear borders are intact and clear.
The scoring system allows the use of ½ grades.

The background is scored after a graded system on a 0-3 scale.

0 Little to no background is seen.
1 Some background.
2 Moderate background.
3 High Background.
The scoring system allows the use of ½ grades.

Example 1

This example compares the signal intensity and cell morphology from samples treated with the compositions of the invention or traditional hybridization solutions as a function of denaturation temperature.

FISH Probe composition I: 10% dextran sulfate, 300 mM NaCl, 5 mM phosphate buffer, 40% formamide (15515-026, Invitrogen), 5 µM blocking PNAs (see Kirsten Yang Nielsen et al., *PNA Suppression Method Combined with Fluorescence In Situ Hybridisation (FISH) Technique* inPRINS and PNA Technologies in Chromosomal Investigation, Chapter 10 (Franck Pellestor ed.) (Nova Science Publishers, Inc. 2006)), 10 ng/µL Texas Red labeled CCND1 gene DNA probe (RP11-1143E20, size 192 kb).

FISH Probe composition II: 10% dextran sulfate, 300 mM NaCl, 5 mM phosphate buffer, 40% Ethylene carbonate (03519, Fluka), 5 µM blocking PNAs, 10 ng/µL Texas Red labeled CCND1 gene DNA probe (RP11-1143E20, size 192 kb).

Phases of different viscosity, if present, were mixed before use. The FISH probes were denatured as indicated for 5 min and hybridized at 45° C. for 60 minutes.

Results:

|  | Signal | | Cell morphology | |
| --- | --- | --- | --- | --- |
|  | (I) | (II) | | |
| Denaturation temperature | Formamide | EC | Formamide | EC |
| 72° C. | 0 | 2 | Good | Good |
| 82° C. | ½ | 3 | Good | Good |
| 92° C. | ½ | 3 | Not good | Not good |

Signals scored as "3" were clearly visible in a 20x objective.

Example 2

This example compares the signal intensity and background staining from samples treated with the compositions of the invention or traditional hybridization solutions as a function of hybridization time.

FISH Probe composition I: 10% dextran sulfate, 300 mM NaCl, 5 mM phosphate buffer, 40% formamide, 5 µM blocking PNAs, 10 ng/µL Texas Red labeled CCND1 gene DNA probe.

FISH Probe composition II: 10% dextran sulfate, 300 mM NaCl, 5 mM phosphate buffer, 40% Ethylene carbonate, 5 µM blocking PNAs, 10 ng/µL Texas Red labeled CCND1 gene DNA probe.

Phases of different viscosity, if present, were mixed before use. The FISH probes were incubated at 82° C. for 5 min and then at 45° C. for 14 hours, 4 hours, 2 hours, 60 minutes, 30 minutes, 15 minutes, 0 minutes.

Results:

|  | Signal | | Background staining | |
| --- | --- | --- | --- | --- |
|  | (I) | (II) | | |
| Hybridization time | Formamide | EC | Formamide | EC |
| 14 hours | 3 | 3 | +½ | +2 |
| 4 hours | 1 | 3 | +½ | +1 |
| 2 hours | ½ | 3 | +0 | +1 |
| 60 min. | ½ | 3 | +0 | +1 |
| 30 min. | 0 | 2½ | +0 | +1 |
| 15 min. | 0 | 2 | +0 | +1 |
| 0 min. | 0 | 1 | +0 | +½ |

Signals scored as "3" were clearly visible in a 20x objective.

Example 3

This example compares the signal intensity from samples treated with the compositions of the invention having different polar aprotic solvents or traditional hybridization solutions.

FISH Probe composition I: 10% dextran sulfate, 300 mM NaCl, 5 mM phosphate buffer, 40% formamide, 5 µM blocking PNAs, 10 ng/µL Texas Red labeled CCND1 gene DNA probe.

FISH Probe composition II: 10% dextran sulfate, 300 mM NaCl, 5 mM phosphate buffer, 40% Ethylene carbonate (EC), 5 µM blocking PNAs, 10 ng/µL Texas Red labeled CCND1 gene DNA probe.

FISH Probe composition III: 10% dextran sulfate, 300 mM NaCl, 5 mM phosphate buffer, 40% Propylene carbonate (PC) (540013, Aldrich), 5 µM blocking PNAs, 10 ng/µL Texas Red labeled CCND1 gene DNA probe.

FISH Probe composition IV: 10% dextran sulfate, 300 mM NaCl, 5 mM phosphate buffer, 40% Sulfolane (SL) (T22209, Aldrich), 5 µM blocking PNAs, 10 ng/µL Texas Red labeled CCND1 gene DNA probe.

FISH Probe composition V: 10% dextran sulfate, 300 mM NaCl, 5 mM phosphate buffer, 40% Aceto nitrile (AN) (C02CIIX, Lab-Scan), 5 µM blocking PNAs, 10 ng/µL Texas Red labeled CCND1 gene DNA probe.

FISH Probe composition VI: 10% dextran sulfate, 300 mM NaCl, 5 mM phosphate buffer, 40% γ-butyrolactone (GBL) (B103608, Aldrich), 5 µM blocking PNAs, 7.5 ng/µL Texas Red labeled CCND1 gene DNA probe.

Phases of different viscosity, if present, were mixed before use. The FISH probes were incubated at 82° C. for 5 min and then at 45° C. for 60 minutes.

Results:

| Signal | | | | | |
| --- | --- | --- | --- | --- | --- |
| (I) | (II) | (III) | (IV) | (V) | (VI) |
| Formamide | EC | PC | SL | AN | GBL |
| ½ | 3 | 3 | 3 | 2 | 3 |

Signals scored as "3" were clearly visible in a 20x objective.

Example 4

This example compares the signal intensity from samples treated with the compositions of the invention having different concentrations of polar aprotic solvent.

FISH Probe Compositions: 10% dextran sulfate, 300 mM NaCl, 5 mM phosphate buffer, 10-60% Ethylene carbonate (as indicated), 5 µM blocking PNAs, 7.5 ng/µL Texas Red labeled /GK-constant DNA gene probe ((CTD-3050E15, RP11-1083E8; size 227 kb) and 7.5 ng/µL FITC labeled /GK-variable gene DNA probe (CTD-2575M21, RP11-122B6, RP11-316G9; size 350 and 429 kb).

Phases of different viscosity, if present, were mixed before use. The FISH probes were incubated at 82° C. for 5 min and then at 45° C. for 60 minutes.

Results:

|  |  | Ethylene carbonate (EC) | | | | |
|---|---|---|---|---|---|---|
|  |  | 10% | 20% | 30% | 40% | 60% |
| Signal intensity | Texas Red | 1½ | 2 | 3 | 3 | 2 |
|  | FITC | 1 | 1½ | 2 | 2½ | 2 |

Signals scored as "3" were clearly visible in a 20x objective.

Example 5

This example compares the signal intensity and background intensity from samples treated with the compositions with and without PNA blocking.

FISH Probe Compositions: 10% dextran sulfate, 300 mM NaCl, 5 mM phosphate buffer, 40% Ethylene carbonate, 7.5 ng/µL Texas Red labeled CCND1 gene DNA probe.

Phases of different viscosity, if present, were mixed before use. The FISH probes were incubated at 82° C. for 5 min and then at 45° C. for 60 minutes.
Results:

|  | Ethylene carbonate (EC) | |
|---|---|---|
|  | PNA- blocking | Non- PNA blocking |
| Signal intensity | 3 | 3 |
| Background intensity | ½+ | ½+ |

Signals scored as "3" were clearly visible in a 20x objective.

Example 6

This example compares the signal intensity from samples treated with the compositions of the invention as a function of probe concentration and hybridization time.

FISH Probe Compositions: 10% dextran sulfate, 300 mM NaCl, 5 mM phosphate buffer, 40% Ethylene carbonate, and 10, 7.5, 5 or 2.5 ng/µL Texas Red labeled CCND1 gene DNA probe (as indicated).

Phases of different viscosity, if present, were mixed before use. The FISH probes were incubated at 82° C. for 5 min and then at 45° C. for 3 hours, 2 hours and 1 hours.
Results:

|  | Signal Intensity | | | |
|---|---|---|---|---|
| Hybridization time | (I) 10 ng/µL | (II) 7.5 ng/µL | (III) 5 ng/µL | (IV) 2.5 ng/µL |
| 3 hours | 3 | 3 | 3 | 3 |
| 2 hours | 3 | 3 | 3 | 1 |
| 1 hours | 3 | 3 | 3 | ½ |

Signals scored as "3" were clearly visible in a 20x objective.

Example 7

This example compares the signal intensity from samples treated with the compositions of the invention as a function of salt, phosphate, and buffer concentrations.

FISH Probe Compositions: 10% dextran sulfate, ([NaCl], [phosphate buffer], [TRIS buffer] as indicated in Results), 40% Ethylene carbonate, 7.5 ng/µL Texas Red labeled CCND1 gene DNA probe.

Phases of different viscosity, if present, were mixed before use. The FISH probes were incubated at 82° C. for 5 min and then at 45° C. for 60 minutes.
Results:

|  | [NaCl] | | |
|---|---|---|---|
|  | 300 mM | 100 mM | 0 mM |
| Signal intensity phosphate [0 mM] | 2 | 1 | ½ |
| Signal intensity phosphate [5 mM] | 3 | 2½ | ½ |
| Signal intensity phosphate [35 mM] | — | — | 3 |
| Signal intensity TRIS [40 mM] | — | — | 2 |

Signals scored as "3" were clearly visible in a 20x objective.

Example 8

This example compares the signal intensity from samples treated with the compositions of the invention as a function of dextran sulfate concentration.

FISH Probe Compositions: 0, 1, 2, 5, or 10% dextran sulfate (as indicated), 300 mM NaCl, 5 mM phosphate buffer, 40% Ethylene carbonate, 5 ng/µL Texas Red labeled SIL-TAL1 gene DNA probe (RP1-278013; size 67 kb) and 6 ng/µL FITC SIL-TAL1 (ICRFc112-112C1794, RP11-184J23, RP11-8J9, CTD-2007B18, 133B9; size 560 kb).

Phases of different viscosity, if present, were mixed before use. The FISH probes were incubated at 82° C. for 5 min and then at 45° C. for 60 minutes. No blocking.
Results:

|  | Signal Intensity | |
|---|---|---|
| % Dextran Sulfate | Texas Red Probe | FITC Probe |
| 0% | 1 | 1 |
| 1% | 1 | 1 |
| 2% | 1½ | 1½ |
| 5% | 2 | 2½ |
| 10% | 2 | 2½ |

NOTE:
this experiment did not produce results scored as "3" because the SIL-TAL1 Texas Red labeled probe is only 67 kb and was from a non-optimized preparation.

Example 9

This example compares the signal intensity from samples treated with the compositions of the invention as a function of dextran sulfate, salt, phosphate, and polar aprotic solvent concentrations.

FISH Probe Composition Ia: 34% dextran sulfate, 0 mM NaCl, 0 mM phosphate buffer, 0% ethylene carbonate, 10 ng/µL Texas Red labeled HER2 gene DNA probe (size 218 kb) and 50 nM of FITC-labeled CEN-7 PNA probe.

FISH Probe Composition Ib: 34% dextran sulfate, 300 mM NaCl, 5 mM phosphate buffer, 0% ethylene carbonate, 10 ng/µL Texas Red labeled HER2 gene DNA probe (size 218 kb) and 50 nM of FITC-labeled CEN-7 PNA probe.

FISH Probe Composition Ic: 34% dextran sulfate, 600 mM NaCl, 10 mM phosphate buffer, 0% ethylene carbonate, 10 ng/µL Texas Red labeled HER2 gene DNA probe (size 218 kb) and 50 nM of FITC-labeled CEN-7 PNA probe.

FISH Probe Composition IIa: 32% dextran sulfate, 0 mM NaCl, 0 mM phosphate buffer, 5% ethylene carbonate, 10 ng/µL Texas Red labeled HER2 gene DNA probe (size 218 kb) and 50 nM of FITC-labeled CEN-7 PNA probe.

FISH Probe Composition IIb: 32% dextran sulfate, 300 mM NaCl, 5 mM phosphate buffer, 5% ethylene carbonate, 10 ng/µL Texas Red labeled HER2 gene DNA probe (size 218 kb) and 50 nM of FITC-labeled CEN-7 PNA probe.

FISH Probe Composition IIc: 32% dextran sulfate, 600 mM NaCl, 10 mM phosphate buffer, 5% ethylene carbonate, 10 ng/µL Texas Red labeled HER2 gene DNA probe (size 218 kb) and 50 nM of FITC-labeled CEN-7 PNA probe.

FISH Probe Composition IIIa: 30% dextran sulfate, 0 mM NaCl, 0 mM phosphate buffer, 10% ethylene carbonate, 10 ng/µL Texas Red labeled HER2 gene DNA probe (size 218 kb) and 50 nM of FITC-labeled CEN-7 PNA probe.

FISH Probe Composition IIIb: 30% dextran sulfate, 300 mM NaCl, 5 mM phosphate buffer, 10% ethylene carbonate, 10 ng/µL Texas Red labeled HER2 gene DNA probe (size 218 kb) and 50 nM of FITC-labeled CEN-7 PNA probe.

FISH Probe Composition IIIc: 30% dextran sulfate, 600 mM NaCl, 10 mM phosphate buffer, 10% ethylene carbonate, 10 ng/µL Texas Red labeled HER2 gene DNA probe (size 218 kb) and 50 nM of FITC-labeled CEN-7 PNA probe.

FISH Probe Composition IVa: 28% dextran sulfate, 0 mM NaCl, 0 mM phosphate buffer, 15% ethylene carbonate, 10 ng/µL Texas Red labeled HER2 gene DNA probe (size 218 kb) and 50 nM of FITC-labeled CEN-7 PNA probe.

FISH Probe Composition IVb: 28% dextran sulfate, 300 mM NaCl, 5 mM phosphate buffer, 15% ethylene carbonate, 10 ng/µL Texas Red labeled HER2 gene DNA probe (size 218 kb) and 50 nM of FITC-labeled CEN-7 PNA probe.

FISH Probe Composition IVc: 28% dextran sulfate, 600 mM NaCl, 10 mM phosphate buffer, 15% ethylene carbonate, 10 ng/µL Texas Red labeled HER2 gene DNA probe (size 218 kb) and 50 nM of FITC-labeled CEN-7 PNA probe.

FISH Probe Reference V: Standard sales vial of HER2 PharmDx probe mix (K5331, Dako) containing blocking PNA. Overnight hybridization for 20 hours.

All compositions were present as a single phase. The FISH probes were incubated at 82° C. for 5 min and then at 45° C. for 60 minutes with no blocking, except for FISH Probe Reference V, which had PNA blocking and was hybridized for 20 hours.

Results:

| | Signal Strength | |
|---|---|---|
| | DNA Probes | PNA Probes |
| Composition Ia | 0 | ½ |
| Composition Ib | 0 | ½ |
| Composition Ic | ½ | 2½ |
| Composition IIa | ½ | 3 |
| Composition IIb | 1 | 2 |
| Composition IIc | ½ | 3 |
| Composition IIIa | 1 | 2½ |
| Composition IIIb | 1½ | 2½ |
| Composition IIIc | 2 | 3 |
| Composition IVa | 2½-3 | 3 |
| Composition IVb | 3 | 3 |
| Composition IVc | 3 | 3 |
| Reference V | 2 | 2½ |

NOTE:
Composition IVa gave strong DNA signals with no salt. This is not possible with standard FISH compositions, where DNA binding is salt dependent.

Example 10

This example compares the signal intensity from samples treated with the compositions of the invention as a function of polar aprotic solvent and dextran sulfate concentration under high salt (4× normal) conditions.

FISH Probe Composition I: 0% ethylene carbonate, 29% dextran sulfate, 1200 mM NaCl, 20 mM phosphate buffer, 10 ng/µL Texas Red labeled HER2 gene DNA probe and 50 nM of FITC-labeled CEN-7 PNA probe. Composition was a single phase.

FISH Probe Composition II: 5% ethylene carbonate, 27% dextran sulfate, 1200 mM NaCl, 20 mM phosphate buffer, 10 ng/µL Texas Red labeled HER2 gene DNA probe and 50 nM of FITC-labeled CEN-7 PNA probe. Composition was a single phase.

FISH Probe Composition III: 10% ethylene carbonate, 25% dextran sulfate, 1200 mM NaCl, 20 mM phosphate buffer, 10 ng/µL Texas Red labeled HER2 gene DNA probe and 50 nM of FITC-labeled CEN-7 PNA probe. Composition was a single phase.

FISH Probe Composition IV (not tested): 20% ethylene carbonate, 21% dextran sulfate, 1200 mM NaCl, 20 mM phosphate buffer, 10 ng/µL Texas Red labeled HER2 gene DNA probe and 50 nM of FITC-labeled CEN-7 PNA probe. Composition had two phases.

Results:

| | Signal Strength | |
|---|---|---|
| | DNA Probes | PNA Probes |
| Composition I | ½ | 3 |
| Composition II | 2 | 2½ |
| Composition III | 3 | 3 |
| Composition IV | — | — |

Note:
Composition II gave good DNA signals with only 5% EC and strong DNA signals with 10% EC.

Example 11

This example compares the signal intensity and background from samples treated with different phases of the compositions of the invention.

FISH Probe Composition: 10% dextran sulfate, 300 mM NaCl, 5 mM phosphate buffer, 40% Ethylene carbonate, 8 ng/µL Texas Red labeled HER2 gene DNA probe and 600 nM FITC-labeled CEN-17 PNA probe. The FISH probes were incubated at 82° C. for 5 min and then at 45° C. for 60 minutes. No blocking.

Results:

| | Signal Intensity | | |
|---|---|---|---|
| | DNA Probe | PNA Probe | Background |
| Upper Phase | 3 | 1½ | +2 |
| Lower Phase | 3 | 2½ | +1 |
| Mix of Upper and Lower Phases | 2½ | 3 | +½ |

NOTE:
the upper phase had more background than the lower phase in these experiments.

Example 12

This example is similar to the previous example, but uses a different DNA probe and GBL instead of EC.

FISH Probe Composition: 10% dextran sulfate, 300 mM NaCl, 5 mM phosphate buffer, 40% GBL, 10 ng/µL Texas Red labeled CCND1 gene DNA probe and 600 nM FITC-labeled CEN-17 PNA probe.

The FISH probes were incubated at 82° C. for 5 min and then at 45° C. for 60 minutes. No blocking.

Results:

|  | Signal Strength | | |
|---|---|---|---|
|  | DNA Probe | PNA Probe | Background |
| Top Phase | 3 | 0-½ | +1½ |
| Bottom Phase | 2 | ½ | +3 |
| Mixed Phases | 2½ | ½ | +2½ |

Example 13

This example examines the number of phases in the compositions of the invention as a function of polar aprotic solvent and dextran sulfate concentration.

FISH Probe Compositions: 10 or 20% dextran sulfate; 300 mM NaCl; 5 mM phosphate buffer; 0, 5, 10, 15, 20, 25, 30% EC; 10 ng/μL probe.

Results:

| % EC | Number of Phases 10% Dextran | Number of Phases 20% Dextran |
|---|---|---|
| 0 | 1 | 1 |
| 5 | 1 | 1 |
| 10 | 1 | 1 |
| 15 | 1 | 1 |
| 20 | 2 | 2 |
| 25 | 2 | 2 |
| 30 | 2 | 2 |

NOTE:
15% EC, 20% dextran sulfate produces the nicest high signal intensities of the above one phase solution. Two phases 20% EC has even higher signal intensities than 15%. (Data not shown).

Example 14

This example compares the signal intensity and background from samples treated with different compositions of the invention as a function of probe concentration and hybridization time.

FISH Probe Composition I: 10 ng/μL HER2 TxRed labeled DNA probe (standard concentration) and standard concentration of CEN7 FITC labeled PNA probe (50 nM); 15% EC; 20% dextran sulfate; 600 mM NaCl; 10 mM phosphate buffer.

FISH Probe Composition II: 5 HER2 TxRed labeled DNA probe (½ of standard concentration) and standard concentration (50 nM) of FITC labeled CEN7 PNA probes; 15% EC; 20% dextran sulfate; 600 mM NaCl; 10 mM phosphate buffer.

FISH Probe Composition III: 2.5 ng/μL HER2 TxRed labeled DNA probe (¼ of standard concentration) and ½ of the standard concentration (25 nM) of CEN7 PNA probes; 15% EC; 20% dextran sulfate; 600 mM NaCl; 10 mM phosphate buffer.

Compositions I-III existed as a single phase. The FISH probes were incubated at 82° C. for 5 min and then at 45° C. for 3 hours, 2 hours and 1 hours.

Results:

| Hybridization time | Signal Intensity | | | | | | | | |
|---|---|---|---|---|---|---|---|---|---|
|  | I | | | II | | | III | | |
|  | DNA | PNA | B.G. | DNA | PNA | B.G. | DNA | PNA | B.G. |
| 3 hours | 3 | 3 | +3 | 3 | 3 | +2.5 | 3 | 3 | +1.5 |
| 2 hours | 2.5 | 2.5 | +3 | 3 | 3 | +3 | 3 | 3 | +1.5 |
| 1 hours | 2.5 | 2.5 | +3 | 3 | 3 | +1.5 | 2.5 | 3 | +1 |

Signals scored as "3" were clearly visible in a 20x objective. B.G.: Back ground.

Example 15

This example compares the signal intensity and background from samples treated with the compositions of the invention as a function of blocking agent.

FISH Probe Compositions: 15% EC; 20% dextran sulfate; 600 mM NaCl; 10 mM phosphate buffer; 2.5 ng/μL HER2 TxRed labeled DNA probe (¼ of standard concentration) and ½ of the standard concentration (300 nM) FITC labeled CEN17 PNA probe. Samples were blocked with: (a) nothing; (b) 0.1 μg/μL COT1 (15279-011, Invitrogen); (c) 0.3 μg/μL COT1; or (d) 0.1 μg/μL total human DNA before hybridization using the compositions of the invention.

All samples were present as a single phase. The FISH probes were incubated at 82° C. for 5 min and then at 45° C. for 60 minutes.

Results:

| Blocking Agent | Background | Signal Intensity | |
|---|---|---|---|
|  |  | DNA | PNA |
| Nothing | +1-1.5 | 3 | 2.5 |
| 0.1 μg/μL COT1 | +1 | 3 | 2.5 |
| 0.3 μg/μL COT1 | +1.5 | 3 | 2.5 |
| 0.1 μg/μL total human DNA | +½ | 3 | 2.5 |

NOTE:
Background levels without blocking are significantly lower than what is normally observed by standard FISH with no blocking. In contrast, if a standard FISH composition does not contain a blocking agent, signals normally cannot be read.

Example 16

This experiment compares different ways of removing background staining using the compositions of the invention.

All compositions contained 15% EC, 20% dextran sulfate, 600 mM NaCl, 10 mM phosphate buffer, 2.5 ng/μL HER2 DNA probes (¼ of standard concentration), 300 nM CEN17 PNA probe (½ of standard concentration), and one of the following background-reducing agents:
A) 5 μM blocking-PNA (see Kirsten Vang Nielsen et al., *PNA Suppression Method Combined with Fluorescence In Situ Hybridisation (FISH) Technique* inPRINS and PNA Technologies in Chromosomal Investigation, Chapter 10 (Franck Pellestor ed.) (Nova Science Publishers, Inc. 2006))
B) 0.1 μg/μL COT-1 DNA
C) 0.1 μg/μL total human DNA (THD) (sonicated unlabelled THD)
D) 0.1 μg/μL sheared salmon sperm DNA (AM9680, Ambion)
E) 0.1 μg/μL calf thymus DNA (D8661, Sigma)
F) 0.1 μg/μL herring sperm DNA (D7290, Sigma)
G) 0.5% formamide
H) 2% formamide
I) 1% ethylene glycol (1.09621, Merck)

J) 1% glycerol (1.04095, Merck)
K) 1% 1,3-Propanediol (533734, Aldrich)
L) 1% H$_2$O (control)

All samples were present as a single phase. The probes were incubated at 82° C. for 5 minutes and then at 45° C. on FFPE tissue sections for 60 and 120 minutes.

Results:

|  |  |  | Signal Intensity | |
| --- | --- | --- | --- | --- |
| Background blocking | Hybridization/min | Background | DNA | PNA |
| Blocking-PNA | 60 | +1 | 3 | 2.5 |
| Blocking-PNA | 120 | +1-1½ | 3 | 2.5 |
| COT-1 | 60 | +½ | 3 | 2.5 |
| COT-1 | 120 | +0-½ | 3 | 2.5 |
| THD | 60 | +0 | 3 | 3 |
| THD | 120 | +½ | 3 | 2.5 |
| Salmon DNA sperm | 60 | +0 | 3 | 3 |
| Salmon DNA sperm | 120 | +0 | 3 | 3 |
| Calf Thymus DNA | 60 | +0 | 2.5 | 3 |
| Calf Thymus DNA | 120 | +½ | 3 | 2.5 |
| Hearing sperm DNA | 60 | +0 | 3 | 3 |
| Hearing sperm DNA | 120 | +½ | 2.5 | 3 |
| 0.5% formamide | 60 | +0 | 2.5 | 3 |
| 0.5% formamide | 120 | +0 | 3 | 3 |
| 2% formamide | 60 | +½ | 2.5 | 3 |
| 2% formamide | 120 | +½ | 3 | 3 |
| 1% Ethylene Glycol | 60 | +½ | 2.5 | 3 |
| 1% Ethylene Glycol | 120 | +1½ | 3 | 2.5 |
| 1% Glycerol | 60 | +½ | 0.5 | 3 |
| 1% Glycerol | 120 | +1 | 3 | 2.5 |
| 1% 1,3-Propanediol | 60 | +0 | 3 | 2.5 |
| 1% 1,3-Propanediol | 120 | +1 | 3 | 2.5 |
| Nothing | 60 | +1 | 2.5 | 2.5 |
| Nothing | 120 | +1½ | 3 | 2.5 |

NOTE:
all background reducing reagents, except for blocking-PNA, showed an effect in background reduction. Thus, specific blocking against repetitive DNA sequences is not required.

Example 17

This experiment compares the signal intensity from the upper and lower phases using two different polar aprotic solvents.

FISH Probe Composition I: 10% dextran sulfate, 300 mM NaCl, 5 mM phosphate buffer, 40% ethylene trithiocarbonate (ET) (E27750, Aldrich), 5 µM blocking PNAs, 10 ng/µL Texas Red labeled CCND1 gene DNA probe.

FISH Probe Composition II: 10% dextran sulfate, 300 mM NaCl, 5 mM phosphate buffer, 40% glycol sulfite (GS) (G7208, Aldrich), 5 µM blocking PNAs, 10 ng/µL Texas Red labeled CCND1 gene DNA probe.

The FISH probes were incubated at 82° C. for 5 min and then at 45° C. for 60 minutes.

Results:

|  | Signal Intensity | |
| --- | --- | --- |
|  | I (ET) | II (GS) |
| Upper Phase | 1½ | 0 |
| Lower Phase | 0 | 3 |
| Mix of Upper and Lower Phases | 2½ | 3 |

Example 18

This experiment examines the ability of various polar aprotic solvents to form a one-phase system.

All compositions contained: 20% dextran sulfate, 600 mM NaCl, 10 mM phosphate buffer, and either 10, 15, 20, or 25% of one of the following polar aprotic solvents:
Sulfolane
γ-Butyrolactone
Ethylene trithiocarbonate
Glycol sulfite
Propylene carbonate Results: all of the polar aprotic solvents at all of the concentrations examined produced at least a two-phase system in the compositions used. However, this does not exclude that these compounds can produce a one-phase system under other composition conditions.

Example 19

This experiment examines the use of the compositions of the invention in chromogenic in situ hybridization (CISH) analysis on multi FFPE tissue sections.

FISH Probe Composition I: 4.5 ng/µL TCRAD FITC labelled gene DNA probe (¼ of standard concentration) (RP11-654A2, RP11-246A2, CTP-2355L21, RP11-158G6, RP11-780M2, RP11-481Cb14; size 1018 kb); 15% EC; 20% dextran sulfate; 600 mM NaCl; 10 mM citrate buffer, pH 6.0.

FISH Probe Composition II: 4.5 ng/µL TCRAD FITC labelled gene DNA probe (¼ of standard concentration) (size 1018 kb); 15% EC; 20% dextran sulfate; 600 mM NaCl; 10 mM citrate buffer, pH 6.0; 0.1 ug/uL sheared salmon DNA sperm.

FISH Probe Composition III: 300 nM of each individual FITC labelled PNA CEN17 probe (½ of standard concentration); 15% EC; 20% dextran sulfate; 600 mM NaCl; 10 mM citrate buffer, pH 6.0.

All samples were analyzed using the Dako DuoCISH protocol (SK108) and compositions for split probes with the exception that the stringency wash was conducted for 20 minutes instead of 10 minutes, and without using the DuoCISH red chromogen step.

Results:

|  | Signal Strength | |
| --- | --- | --- |
| Composition | FITC DNA | FITC PNA |
| I | 3 | — |
| II | 3 | — |
| III | — | 3 |

Note:
The signal intensities were very strong. Due to the high levels of background, it was not possible to discriminate if addition of salmon sperm DNA in Composition II reduced the background. Signals were clearly visible using a 10x objective in e.g. tonsils, which in general had less background. If tissues possessed high background, the signals were clearly visible using a 20x objective.

Example 20

This example compares the signal intensity and background from FFPE tissue sections treated with the compositions of the invention with two DNA probes.

FISH Probe Composition I: 9 ng/µL IGH FITC labelled gene DNA probe (RP11-151B17, RP11-112H5, RP11-101G24, RP11-12F16, RP11-47P23, CTP-3087C18; size 612 kb); 6.4 ng/µL MYC Tx Red labeled DNA probe (CTD- 2106F24, CTD-2151C21, CTD-2267H22; size 418 kb); 15% EC; 20% dextran sulfate; 600 mM NaCl; 10 mM citrate buffer, pH 6.0.

FISH Probe Composition II: 9 ng/µL IGH FITC labelled gene DNA probe; 6.4 ng MYC TxRed labeled DNA probe; 15% EC, 20% dextran sulfate; 600 mM NaCl; 10 mM citrate buffer, pH 6.0; 0.1 ug/uL sheared salmon sperm DNA.

| | Signal Strength | | |
|---|---|---|---|
| Salmon DNA | FITC probe | Texas Red probe | Background |
| − | 2½ | 2½ | +2.5 |
| + | 3 | 3 | +1.5 |

NOTE:
the high background was probably due to the fact that standard probe concentrations were used.

Example 21

This experiment examines the use of the compositions of the invention on cytological samples.

FISH Probe Composition: 15% EC; 20% dextran sulfate; 600 mM NaCl; 10 mM phosphate buffer; 5 ng/µL HER2 TxRed labeled DNA probe (½ of standard concentration) and ½ of the standard concentration of CENT (25 nM).

The FISH probes were incubated on metaphase chromosome spreads at 82° C. for 5 minutes, then at 45° C. for 30 minutes, all without blocking.

Results:

| Signal Strength | | |
|---|---|---|
| DNA Probe | PNA Probe | Background |
| 3 | 3 | +1 |

No chromosome banding (R-banding pattern) was observed with the compositions of the invention, in contrast with traditional ISH solutions, which typically show R-banding. A low homogenously red background staining of the interphase nuclei and metaphase chromosomes was observed.

Example 22

This example compares the signal intensity and background from DNA probes on cytology samples, metaphase spreads, with and without blocking.

FISH Probe Composition I: 6 ng/µL TCRAD Texas Red labelled gene DNA probe (standard concentration) (CTP-31666K20, CTP-2373N7; size 301 kb) and 4.5 ng/µL FITC labelled gene DNA probe (¼ of standard concentration); 15% EC, 20% dextran sulfate; 600 mM NaCl; 10 mM citrate buffer, pH 6.0.

FISH Probe Composition II: 6 ng/µL TCRAD Texas Red labelled gene DNA probe (standard concentration) (size 301 kb) and 4.5 ng/µL FITC labelled gene DNA probe (¼ of standard concentration); 15% EC, 20% dextran sulfate; 600 mM NaCl; 10 mM citrate buffer, pH 6.0; 0.1 ug/uL sheared salmon sperm DNA.

The FISH probes were incubated on metaphase spreads at 82° C. for 5 min, then at 45° C. for 60 min.

Results:

| | | Signal Intensity | |
|---|---|---|---|
| Blocking Agent | Background | Tx Red | FITC |
| Nothing | +0 | 3 | 3 |
| 0.1 µg/µL Salmon DNA | +0 | 3 | 3 |

Again, no chromosome banding (R-banding pattern) was observed with the compositions of the invention. In addition, no background staining of the interphase nuclei or the metaphase chromosomes were observed.

Further Embodiments

Embodiment 1. A hybridization composition comprising:
(a) a first molecular probe that detects a nucleotide sequence associated with a chromosomal aberration,
(b) at least one polar aprotic solvent in an amount effective to denature double-stranded nucleotide sequences, and
(c) a hybridization solution,
wherein the nucleotide sequence is a marker for a chromosomal aberration, and wherein the polar aprotic solvent is not dimethyl sulfoxide (DMSO).

Embodiment 2. The hybridization composition according to embodiment 1, wherein the chromosomal aberration is aneuploidy, potential breakpoint, insertion, inversion, deletion, duplication, gene amplification, rearrangement, or translocation.

Embodiment 3. The hybridization composition according to embodiments 1-2, wherein the chromosomal aberration is associated with a congenital genetic disorder, cancer, or infection.

Embodiment 4. The hybridization composition according to embodiment 3, wherein the chromosomal aberration is associated with cancer.

Embodiment 5. The hybridization composition according to embodiment 4, wherein the first molecular probe detects ALK, BCL2, BCL3, BCL6, BCL10, BCL12, BCR, CCND1, E2A, EGFR, ETV6, FIP1L1, HER2, IGH, IGK, IGL, MALT1, MLL (ALL-1, HTRX1, HRX), MYC (c-Myc), PAX5, PDGFRA, PDGFRB, SIL, TCF3 (E2A, ITF1), TCL1A, TCRAD, TCRB, TCRG, telomere, TLX1, TLX3 (HOX11L2, RNX), or TOP2A.

Embodiment 6. The hybridization composition according to any of embodiments 1-4, wherein the first molecular probe detects a target for a non-haematological disease selected from the group consisting of: BASE, BRCA1, CCND1, CCNE1, DCD, E2F3, n-MYC/MYCN, COX-2/PTGS2, LRIG1, ER a, hTERT, MLN64/STARD3, PGR, SNAI1, SRC, TOP1, TUBB1, AIB1, DLC-1, EDD, Pip4k2b/5k, Sil, TBX2, c-Kit, VEGF, VCAM-1, Tie-1, Ts/TYMS, PSMA, PSA, PAP, P15, P16, BCL1, BCL2, MTOR, TIMP1, ESR1, PTEN, MDM2/CDK4, MET, C-MET, ERB1, FGFR1, IGF1R, NET, FGFR3, ABCB1, TMPRSS2, BRCA2, TOP2B, ERCC1, AKT1, AKT2, AKT3, HRAS, NRAS, RAF1, HER3, HER4, ENT1, RRM1, RRM2, RRM2B, PIK3CA, AURK4, AURKB, AURKC, MAPT/tau, TTBK1, TUBB, VEGFR, CCND3, CDK6, CDK2, CDC2, HDAC, ESR2, SCUBE2, BIRC5, FASN, DHFR, TP/ECGF1, TYMP, DPYD, TK1, HMGIC, ABCA2, ABCB11, ABCC1, ABCC2, ABCC3, ABCC4, ABCC5, ABCG2, MVP, ATP7A, ATP7B, SLC29A1, SLC28A1, SLC19A1, TUBB4, TUBA, MAP4, MAP7, STMN1, KIF5B, HSPA5, PSMD14, FPGS, GSTP1, GPX, GCLC, GGT2, MT, AKR1B1, HMGB1, HMGB2, XPA, XPD, MSH2, MLH1, PMS2, APEX1, MGMT, GLO1, RB1, GML, CDKN1A, CDKN2A, CDKN1B, ERBB2, KRAS2, ITGB1, JUN, FOS, NFKB1, TP53, TP73, BCL2L1, MCL1, BAX, BIRC4, TNFRSF6, CASP3, CASP8, HSPB1, MALAT1(alpha) t(11;19)(q11;q13.4), MHLB1 t(11;19) (q11;q13.4), COL1A1 t(17;22)(q22;q13), PDGFB t(17;22) (q22;q13), FKHR t(2;13) & t(1;13), ETV6 t(12;15)(p13; q25), NTRK3 t(12;15)(p13;q25), TLS/FUS t(12;16)(q13; p11), CHOP t(12;16)(q13;p11), EWS t(12;22)(q13;q12), EWS/FLI1 t(11;22)(q24;q12), and FLI1 t(11;22)(q24;q12).

Embodiment 7. The hybridization composition according to any of embodiments 1-4, wherein the first molecular probe detects a target for a haematological disease selected from the group consisting of: ABL t(9;22)(q34;q11), PRDM16 del (1p36.32) del(21q22.12), RUNX1/AML1 del(1p36.32) del (21q22.12), CEP8, PDGFRB, NUP98, FGFR1, ASS, ETO t(8;21)(q22;q22), AML1 t(8;21)(q22;q22), CBFbeta inv(16) (p13q22) t(16;16)(p13;q22), MYH11 inv(16)(p13q22) t(16; 16)(p13;q22), AF9 t(9;11), PML t(15;17)(q22;q21), PLZF t(11;17)(q23;q21), NuMA t(11;17)(q13;q21), NPM t(5;17) (q23;q12), RAR alpha t(15;17)(q22;q21) t(11;17)(q23;q21) t(11;17)(q13;q21) t(5;17)(q23;q21), EVI1 t(3;v)(q26;v), GR6 t(3;3)(q21;q26), RPN1 t(3;3)(q21;q26), DEK t(6;9), CAN t(6;9), MLF1 t(3;5)( . . . ;q23), FUS t(16;21), ERG t(16;21), NUP98 t(7;11), HOX9A t(7;11), MOZ/MYST3 t(8; 16)(p11;p13), CBP t(8;16)(p11;p13), p300 t(8;22)(p11;q13), TIF2/GRIP-1/NCoA-2 inv(8)(p11q13), MKL1, PBX1 t(1; 19)(q23;p13.3)+var., ABL t(9;22)(q34;q11), AF4/AFF1 t(4; 11)(q21;q23) AML1/RUNX1 t(12;21)(p13;q22), IL3 t(5;14) (q31;q32), HLF t(17;19), IKZF1 del(7)(p12.2), CDKN2A/ CDKN2B del(9)(p21.3), TAL1 1p32 aberrations, LMO2 t(11; 14)(p13;q11)+var., LMO1 t(11;14)(p15;q11), HOX11 t(10; 14)(q24;q11)+var., TAL2 t(7;9)(q34;q32), TAN1 t(7;9)(q34; q34), CEP12, ATM, D13S25, D13S319, TO53, P53, TNFAIP3 del(6)(q23.3-q24.1), CDK6 BCL1 t(11;14)(q13; q32)+var., IRF4 t(6;14)(p25;q32), C-MAF t(14;16)(q32; q23), FGFR3 t(4;14)(p16;q32), MUM2/3 t(1;14)(q21;q32), NPM t(2;5)(p23;q35), ASS, RB1, and ATM.

Embodiment 8. The hybridization composition according to any of embodiments 1-4, wherein the first molecular probe detects a centromere selected from the group consisting of: CEP1, CEP2, CEP3, CEP4, CEPS, CEP6, CEP7, CEP8, CEP9, CEP10, CEP11, CEP12, CEP13, CEP14, CEP15, CEP16, CEP17, CEP18, CEP19, CEP20, CEP21, CEP22, CEP23, CEP X, and CEP Y.

Embodiment 9. The hybridization composition according to embodiment 4, wherein the cancer is adrenocortical carcinoma, bladder cancer, brain cancer, burn cancer, breast cancer, cervical cancer, colorectal cancer, colon cancer, rectal cancer, endometrial cancer, esophageal cancer, kidney (renal) cancer, leukemia, liver cancer, lung cancer, gastric cancer, glioma, hematological cancer, head and neck cancer, melanoma, lymphoma, leukemia, non-Hodgkin lymphoma, ovarian cancer, pancreatic cancer, prostate cancer, retinoblastoma, sarcoma, skin cancer (nonmelanoma), testicular cancer, thyroid cancer, or uterine cancer.

Embodiment 10. The hybridization composition according to embodiment 9, wherein the cancer is breast cancer and the first molecular probe detects HER2.

Embodiment 11. The hybridization composition according to embodiment 9, wherein the cancer is colorectal cancer and the first molecular probe detects EGF2.

Embodiment 12. The hybridization composition according to embodiment 4, wherein the cancer is a hematopoietic malignancy.

Embodiment 13. The hybridization composition according to embodiment 12, wherein the first molecular probe detects a chromosomal aberration chosen from t(1;14) (q34;q11), t(1;19) (q23;p13), t(2;5), t(2;18) (q12;q21), t(2;8), t(4;11), t(4;11) (q21; q23), t(6;11) (q27;q23), t(7;22) (p22;q12), t(8; 14), t(8;22), t(9;11) (p22;q23), t(9;22) (q34;q11), t(10;14) (q24;q11), t(11;14), t(11;14) (p13;q11), t(11;19) (q23;p13), t(14;18) (q23; q21), t(14;18), t(18;22) (q21;q11), and t(21; 22) (q22;q12).

Embodiment 14. The hybridization composition according to any one of embodiments 1 to 13, further comprising a second molecular probe.

Embodiment 15. The hybridization composition according to embodiment 14, wherein the second molecular probe detects a reference sequence.

Embodiment 16. The hybridization composition according to embodiment 15, wherein the reference sequence is a centromere sequence.

Embodiment 17. The hybridization composition according to embodiment 16, wherein the molecular probe is defined in embodiment 8.

Embodiment 18. The hybridization composition according to embodiment 14, wherein the first molecular probe and the second molecular probe detect sequences flanking or within one or more potential breakpoint.

Embodiment 19. The hybridization composition according to any one of embodiments 14 to 18, further comprising a third molecular probe.

Embodiment 20. The hybridization composition according to any one of embodiments 1 to 19, wherein the first molecular probe is a DNA probe, a PNA probe, or an LNA probe.

Embodiment 21. The hybridization composition according to any one of embodiments 14 to 20, wherein the second molecular probe is a DNA probe, a PNA probe, or an LNA probe.

Embodiment 22. The hybridization composition according to any of embodiments 19-21, wherein the third molecular probe is a DNA probe, a PNA probe, or an LNA probe.

Embodiment 23. The hybridization composition according to any one of embodiments 1 to 22, wherein the molecular probe further comprises a label.

Embodiment 24. The hybridization composition according to embodiment 23, wherein the label is a chromophore, fluorophore, biotin, DIG, antibody-hapten, dye, or enzyme.

Embodiment 25. The hybridization composition according to any of embodiments 1 to 24, wherein the concentration of polar aprotic solvent in the hybridization composition ranges from 1% (v/v) to 95% (v/v).

Embodiment 26. The hybridization composition according to any one of embodiments 1 to 25, wherein the concentration of polar aprotic solvent in the hybridization composition ranges from 5% (v/v) to 10% (v/v).

Embodiment 27. The hybridization composition according to any one of embodiments 1 to 25, wherein the concentration of polar aprotic solvent in the hybridization composition ranges from 10% (v/v) to 20% (v/v).

Embodiment 28. The hybridization composition according to any one of embodiments 1 to 25, wherein the concentration of polar aprotic solvent in the hybridization composition ranges from 20% (v/v) to 30% (v/v).

Embodiment 29. The hybridization composition according to any of embodiments 1 to 28, wherein the polar aprotic solvent is non-toxic.

Embodiment 30. The hybridization composition according to any of embodiments 1 to 29, with the proviso that the hybridization composition does not contain formamide.

Embodiment 31. The hybridization composition according to any of embodiments 1 to 30, with the proviso that the hybridization composition contains less than 10% formamide.

Embodiment 32. The hybridization composition according to any of embodiments 1 to 31, wherein the polar aprotic solvent has lactone, sulfone, sulfite, nitrile and/or carbonate functionality.

Embodiment 33. The hybridization composition according to any one of embodiments 1 to 32, wherein the polar aprotic solvent has a dispersion solubility parameter ranging from 17.7 MPa$^{1/2}$ to 22.0 MPa$^{1/2}$, a polar solubility parameter ranging from 13 MPa$^{1/2}$ to 23 MPa$^{1/2}$, and a hydrogen bonding solubility parameter ranging from 3 MPa$^{1/2}$ to 13 MPa$^{1/2}$.

Embodiment 34. The hybridization composition according to any one of embodiments 1 to 33, wherein the polar aprotic solvent has a cyclic base structure.

Embodiment 35. The hybridization composition according to any one of embodiments 1 to 34, wherein the polar aprotic solvent is selected from the group consisting of

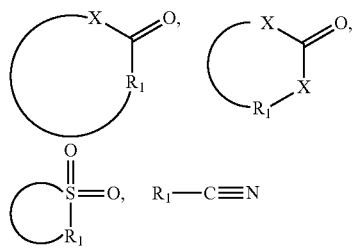

where X is O and R1 is alkyldiyl, and

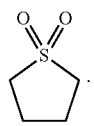

where X is optional and if present, is chosen from O or S,
where Z is optional and if present, is chosen from O or S,
where A and B independently are O or N or S or part of the alkyldiyl or a primary amine,
where R is alkyldiyl, and
where Y is O or S or C.

Embodiment 36. The hybridization composition according to any one of embodiments 1 to 35, wherein the polar aprotic solvent is selected from the group consisting of: acetanilide, acetonitrile, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, dipheynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, ethylene glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

Embodiment 37. The hybridization composition according to any one of embodiments 1 to 35, wherein the polar aprotic solvent is selected from the group consisting of:

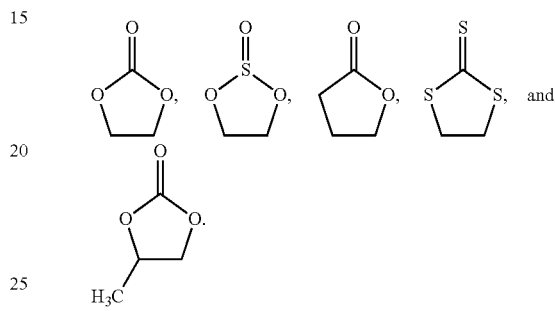

Embodiment 38. The hybridization composition according to any one of embodiments 1 to 35, wherein the polar aprotic solvent is:

Embodiment 39. The hybridization composition according to any one of embodiments 1 to 38, further comprising at least one additional component selected from the group consisting of: buffering agents, salts, accelerating agents, chelating agents, detergents, and blocking agents Embodiment 40. The hybridization composition according to embodiment 39, wherein the accelerating agent is dextran sulfate and the salts are sodium chloride and/or sodium phosphate.

Embodiment 41. The hybridization composition according to embodiment 40, wherein the dextran sulfate is present at a concentration of 5% to 40%, the sodium chloride is present at a concentration of 0 mM to 1200 mM, and/or the sodium phosphate is present at a concentration of 0 mM to 50 mM.

Embodiment 42. The hybridization composition according to embodiment 41, wherein the dextran sulfate is present at a concentration of 10% to 30%, the sodium chloride is present at a concentration of 300 mM to 1200 mM, and/or the sodium phosphate is present at a concentration of 5 mM to 20 mM.

Embodiment 43. The hybridization composition according to embodiment 39, wherein the accelerating agent is selected from the group consisting of: formamide, glycerol, propylene glycol, 1,2-propanediol, diethylene glycol, ethylene glycol, glycol, and 1,3 propanediol, and the buffering agent is citric acid buffer.

Embodiment 44. The hybridization composition according to embodiment 43, wherein the formamide is present at a concentration of 0.1-5%, the glycerol, propylene glycol, 1,2-propanediol, diethylene glycol, ethylene glycol, glycol, and 1,3 propanediol are present at a concentration of 0.1% to 10%, and the citric acid buffer is present at a concentration of 1 mM to 50 mM.

Embodiment 45. The hybridization composition according to embodiment 39, wherein the blocking agent is selected from the group consisting of: total human DNA, herring sperm DNA, salmon sperm DNA, and calf thymus DNA.

Embodiment 46. The hybridization composition according to embodiment 45, wherein the total human DNA, herring sperm DNA, salmon sperm DNA, and calf thymus DNA are present at a concentration of 0.01 to 10 µg/µL.

Embodiment 47. The hybridization composition according to any one of embodiments 1 to 46, comprising 40% of at least one polar aprotic solvent, 10% dextran sulfate, 300 mM sodium chloride, and 5 mM sodium phosphate.

Embodiment 48. The hybridization composition according to any one of embodiments 1 to 46, comprising 15% of at least one polar aprotic solvent, 20% dextran sulfate, 600 mM sodium chloride, 10 mM sodium phosphate, and 0.1 µg/µl total human DNA.

Embodiment 49. The hybridization composition according to any one of embodiments 1 to 46, comprising 15% of at least one polar aprotic solvent, 20% dextran sulfate, 600 mM sodium chloride, 10 mM citric acid buffer pH 6.2, and 0.1 µg/µL herring sperm DNA, or salmon sperm DNA, or calf thymus DNA, or 0.5% formamide, or 1% ethylene glycol, or 1% 1,3 propanediol, or 1% glycerol.

Embodiment 50. The hybridization composition according to any one of embodiments 1 to 49, wherein the aqueous composition comprises more than one phase at room temperature.

Embodiment 51. A kit comprising the composition of any one of embodiments 1 to 41.

Embodiment 52. A kit comprising:
 (a) a first molecular probe that detects a nucleotide sequence associated with a chromosomal aberration, and
 (b) a hybridization composition comprising at least one polar aprotic solvent in an amount effective to denature double-stranded nucleotide sequences,
 wherein the polar aprotic solvent is not dimethyl sulfoxide (DMSO).

Embodiment 53. The kit according to either of embodiments 51 and 52, further comprising a visualization reagent.

Embodiment 54. The kit according to either of embodiments 51 and 52, wherein the kit is designed for use in cytology.

Embodiment 55. The kit according to either of embodiments 51 and 52, wherein the kit is designed for use in histology.

Embodiment 56. The kit according to embodiment 52, wherein the polar aprotic solvent is defined according to any of embodiments 25-38.

Embodiment 57. The kit according to any of embodiments 51-56, wherein the kit is designed for use in FISH or CISH experiments.

Embodiment 58. A method of detecting a target in chromosomal DNA comprising
 providing at least one molecular probe that hybridizes to the target in chromosomal DNA,
 providing chromosomal DNA,
 providing a hybridization composition comprising at least one polar aprotic solvent in an amount effective to denature double-stranded nucleotide sequences, wherein the polar aprotic solvent is not dimethyl sulfoxide (DMSO),
 combining the molecular probe, the chromosomal DNA and the hybridization composition for at least a time period sufficient to hybridize the molecular probe to the target, and
 detecting the target.

Embodiment 59. A method of determining the presence of a chromosomal aberration in a nucleic acid sequence, the method comprising:
 providing at least one molecular probe,
 providing the nucleic acid sequence,
 providing a hybridization composition comprising at least one polar aprotic solvent in an amount effective to denature double-stranded nucleotide sequences, wherein the polar aprotic solvent is not dimethyl sulfoxide (DMSO),
 combining the molecular probe and the nucleic acid sequence and the hybridization composition for at least a time period sufficient to hybridize the molecular probe and the nucleic acid sequence, and
 detecting the at least one molecular probe,
 and determining the presence of the chromosomal aberration.

Embodiment 60. A method of determining the presence of a chromosomal aberration in a nucleic acid sequence, the method comprising:
 providing the nucleic acid sequence,
 providing a hybridization composition comprising at least one molecular probe and at least one polar aprotic solvent in an amount effective to denature double-stranded nucleotide sequences,
 applying the hybridization composition to said nucleic acid for at least a time period sufficient to hybridize the molecular probe and nucleic acid sequence, and
 detecting the at least one molecular probe,
 and determining the presence of the chromosomal aberration,
 wherein the polar aprotic solvent is not dimethyl sulfoxide (DMSO).

Embodiment 61. The method according to any of embodiments 58 to 60, wherein the polar aprotic solvent is defined according to any one of embodiments 25-38.

Embodiment 62. A method of determining the presence of a chromosomal aberration in a nucleic acid sequence, the method comprising:
 providing the nucleic acid sequence,
 applying a composition according to any one of embodiments 1 to 50 to said nucleic acid sequence for at least a time period sufficient to hybridize the molecular probe and nucleic acid sequence, and
 determining whether the chromosomal aberration is present in the nucleic acid sequence.

Embodiment 63. The method according to any of embodiments 58 to 62, wherein a sufficient amount of energy to hybridize the first and second nucleic acids is provided.

Embodiment 64. The method according to embodiment 63, wherein the energy is provided by heating the hybridization composition and nucleic acid sequence.

Embodiment 65. The method according to embodiment 64, wherein the heating step is performed by the use of microwaves, hot baths, hot plates, heat wire, peltier element, induction heating or heat lamps.

Embodiment 66. The method according to any one of embodiments 58 to 65, wherein the nucleic acid sequence is double stranded and the molecular probe is single stranded, the nucleic acid sequence is double stranded and the molecular probe is double stranded, the nucleic acid sequence is single stranded and the molecular probe is single stranded, or the nucleic acid sequence is single stranded and the molecular probe is double stranded.

Embodiment 67. The method according to any one of embodiments 58 to 66, wherein the denaturation and hybridization steps occur separately.

Embodiment 68. The method according to any one of embodiments 58 to 67, wherein the step of hybridizing includes the steps of heating and cooling the hybridization composition, molecular probe, and nucleic acid sequence.

Embodiment 69. The method according to any one of embodiments 58 to 68, wherein the step of hybridization takes less than 8 hours.

Embodiment 70. The method according to embodiment 69, wherein the step of hybridization takes less than 1 hour.

Embodiment 71. The method according to any one of embodiments 58 to 70, wherein the cooling step takes less than 1 hour.

Embodiment 72. The method according to embodiment 71, wherein the cooling step takes less than 30 minutes.

Embodiment 73. The method according to any one of embodiments 58 to 72, wherein the nucleic acid sequence is in a biological sample.

Embodiment 74. The method according to embodiment 73, wherein the biological sample is a tissue sample.

Embodiment 75. The method according to any one of embodiments 58 to 74, wherein the aqueous composition comprises one phase at room temperature.

Embodiment 76. The method according to any one of embodiments 58 to 74, wherein the aqueous composition comprises multiple phases at room temperature.

Embodiment 77. The method according to embodiment 76, wherein the layers of the aqueous composition are mixed.

Embodiment 78. The method according to any one of embodiments 58 to 77, further comprising a blocking step.

Embodiment 79. A method of diagnosing a congenital genetic disorder, cancer, or infection associated with a chromosomal aberration, the method comprising
providing a tissue sample from a subject, wherein the tissue sample comprises a nucleic acid sequence,
determining whether a chromosomal aberration is present in the nucleic acid sequence, according to the method of any of embodiments 58 to 78, and
diagnosing the congenital genetic disorder, cancer, or infection if the chromosomal aberration is present in the tissue sample.

Embodiment 80. Use of a composition comprising a molecular probe that detects a nucleotide sequence associated with a chromosomal aberration and a hybridization composition comprising 1% (v/v) to 95% (v/v) of at least one polar aprotic solvent in a hybridization assay for detecting the nucleotide sequence associated with a chromosomal aberration.

Embodiment 81. Use according to embodiment 80, of a composition according to any one of embodiments 1 to 50.

The invention claimed is:
1. A composition comprising:
(a) a first molecular probe that detects a nucleotide sequence associated with a chromosomal aberration,
(b) at least one polar aprotic solvent in an amount effective to denature double-stranded nucleotide sequences within a sample having a preserved cell morphology, and
(c) a hybridization solution,
wherein the nucleotide sequence is a marker for a chromosomal aberration,
wherein the polar aprotic solvent has lactone, sulfone, sulfite, nitrile, and/or carbonate functionality, and
wherein the polar aprotic solvent has a cyclic base structure.

2. The composition according to claim 1, wherein the chromosomal aberration is aneuploidy, potential breakpoint, insertion, inversion, deletion, duplication, gene amplification, rearrangement, or translocation.

3. The composition according to claim 1, wherein the chromosomal aberration is associated with a congenital genetic disorder, cancer, or infection.

4. The composition according to claim 3, wherein the chromosomal aberration is associated with cancer.

5. The composition according to claim 4, wherein the first molecular probe detects ALK, BCL2, BCL3, BCL6, BCL10, BCL12, BCR, CCND1, E2A, EGFR, ETV6, FIP1L1, HER2, IGH, IGK, IGL, MALT1, MLL (ALL-1, HTRX1, HRX), MYC (c-Myc), PAX5, PDGFRA, PDGFRB, SIL, TCF3 (E2A, ITF1), TCL1A, TCRAD, TCRB, TCRG, telomere, TLX1, TLX3 (HOX11L2, RNX), or TOP2A.

6. The composition according to claim 1, wherein the first molecular probe detects a target for a non-hematological disease selected from the group consisting of: BASE, BRCA1, CCND1, CCNE1, DCD,E2F3, n-MYC/MYCN, COX-2/PTGS2, LRIG1, ER a, hTERT, MLN64/STARD3, PGR, SNAI1, SRC, TOP1, TUBB1, AIB1, DLC-1, EDD, Pip4k2b/5k, Sil, TBX2, c-Kit, VEGF, VCAM-1, Tie-1, Ts/TYMS, PSMA, PSA, PAP, P15, P16, BCL1, BCL2, MTOR, TIMP1, ESR1, PTEN, MDM2/CDK4, MET, C-MET, ERB1, FGFR1, IGF1R, NET, FGFR3, ABCB1, TMPRSS2, BRCA2, TOP2B, ERCC1, AKT1, AKT2, AKT3, HRAS, NRAS, RAF1, HER3, HER4, ENT1, RRM1, RRM2, RRM2B, PIK3CA, AURK4, AURKB, AURKC, MAPT/tau, TTBK1, TUBB, VEGFR, CCND3, CDK6, CDK2, CDC2, HDAC, ESR2, SCUBE2, BIRC5, FASN, DHFR, TP/ECGF1, TYMP, DPYD, TK1, HMGIC, ABCA2, ABCB11, ABCC1, ABCC2, ABCC3, ABCC4, ABCC5, ABCG2, MVP, ATP7A, ATP7B, SLC29A1, SLC28A1, SLC19A1, TUBB4, TUBA, MAP4, MAP7, STMN1, KIF5B, HSPA5, PSMD14, FPGS, GSTP1, GPX, GCLC, GGT2, MT, AKR1B1, HMGB1, HMGB2, XPA, XPD, MSH2, MLH1, PMS2, APEX1, MGMT, GLO1, RB1, GML, CDKN1A, CDKN2A, CDKN1B, ERBB2, KRAS2, ITGB1, JUN, FOS, NFKB1, TP53, TP73, BCL2L1, MCL1, BAX, BIRC4, TNFRSF6, CASP3, CASP8, HSPB1, MALAT1(alpha) t(11;19)(q11; q13.4), MHLB1 t(11;19)(q11;q13.4), COL1A1 t(17;22) (q22;q13), PDGFB t(17;22)(q22;q13), FKHR t(2;13) & t(1; 13), ETV6 t(12;15)(p13;q25), NTRK3 t(12;15)(p13;q25), TLS/FUS t(12;16)(q13;p11), CHOP t(12;16)(q13;p11), EWS t(12;22)(q13;q12), EWS/FLI1 t(11;22)(q24;q12), and FLI1 t(11;22)(q24;q12).

7. The composition according to claim 1, wherein the first molecular probe detects a target for a hemaetological disease selected from the group consisting of: ABL t(9;22)(q34;q11), PRDM16 del(1p36.32) del(21q22.12), RUNX1/AML1 del (1p36.32) del(21q22.12), CEP8, PDGFRB, NUP98, FGFR1, ASS, ETO t(8;21)(q22;q22), AML1 t(8;21)(q22;q22), CBF-beta inv(16)(p13q22) t(16;16)(p13;q22), MYH11 inv(16) (p13q22) t(16;16)(p13;q22), AF9 t(9;11), PML t(15;17)(q22; q21), PLZF t(11;17)(q23;q21), NuMA t(11;17)(q13;q21), NPM t(5;17)(q23;q12), RAR alpha t(15;17)(q22;q21) t(11; 17)(q23;q21) t(11;17)(q13; q21) t(5;17)(q23;q21), EVI1 t(3; v)(q26;v), GR6 t(3;3)(q21;q26), RPN1 t(3;3) (q21;q26), DEK t(6;9), CAN t(6;9), MLF1 t(3;5)( . . . ;q23), FUS t(16; 21), ERG t(16;21), NUP98 t(7;11), HOX9A t(7;11), MOZ/MYST3 t(8;16)(p11;p13), CBP t(8;16)(p11;p13), p300 t(8; 22)(p11;q13), TIF2/GRIP-1/NCoA-2 inv(8)(p11q13), MKL1, PBX1 t(1;19)(q23;p13.3) +var., ABL t(9;22)(q34; q11), AF4/AFF1 t(4;11)(q21;q23), AML1/RUNX1 t(12;21) (p13;q22), IL3 t(5;14)(q31;q32), HLF t(17;19), IKZF1 del(7) (p12.2), CDKN2A/CDKN2B del(9)(p21.3), TAL1 1p32 aberrations, LMO2 t(11;14)(p13;q11)+var., LMO1 t(11;14) (p15;q11), HOX11 t(10;14)(q24;q11)+var., TAL2 t(7;9)(q34; q32), TAN1 t(7;9)(q34;q34), CEP12, ATM, D13S25, D13S319, TP53, P53, TNFAIP3 del(6)(q23.3-q24.1), CDK6 BCL1 t(11;14)(q13;q32)+var., IRF4 t(6;14)(p25;q32), C-MAF t(14;16)(q32;q23), FGFR3 t(4;14)(p16;q32), MUM2/3 t(1;14)(q21;q32), NPM t(2;5)(p23;q35), ASS, RB1, and ATM.

8. The composition according to claim 1, wherein the first molecular probe detects a centromere selected from the group consisting of: CEP1, CEP2, CEP3, CEP4, CEP5, CEP6, CEP7, CEP8, CEP9, CEP10, CEP11, CEP12, CEP13, CEP14, CEP15, CEP16, CEP17, CEP18, CEP19, CEP20, CEP21, CEP22, CEP23, CEP X, and CEP Y.

9. The composition according to claim 4, wherein the cancer is adrenocortical carcinoma, bladder cancer, brain cancer, burn cancer, breast cancer, cervical cancer, colorectal cancer, colon cancer, rectal cancer, endometrial cancer, esophageal cancer, kidney (renal) cancer, leukemia, liver cancer, lung cancer, gastric cancer, glioma, hematological cancer, head and neck cancer, melanoma, lymphoma, leukemia, non-Hodgkin lymphoma, ovarian cancer, pancreatic cancer, prostate cancer, retinoblastoma, sarcoma, skin cancer (nonmelanoma), testicular cancer, thyroid cancer, or uterine cancer.

10. The composition according to claim 9, wherein the cancer is breast cancer and the first molecular probe detects HER2.

11. The composition according to claim 9, wherein the cancer is colorectal cancer and the first molecular probe detects EGFR.

12. The composition according to claim 4, wherein the cancer is a hematopoietic malignancy.

13. The composition according to claim 12, wherein the first molecular probe detects a chromosomal aberration chosen from t(1;14) (q34;q11), t(1;19) (q23;p13), t(2;5), t(2;18) (q12;q21), t(2;8), t(4;11), t(4;11) (q21;q23), t(6;11) (q27; q23), t(7;22) (p22;q12), t(8;14), t(8;22), t(9;11) (p22;q23), t(9;22) (q34;q11), t(10;14) (q24;q11), t(11;14), t(11;14) (p13;q11), t(11;19) (q23;p13), t(14;18) (q23;q21), t(14;18), t(18;22) (q21;q11), and t(21;22) (q22;q12).

14. The composition according to claim 1, further comprising a second molecular probe.

15. The composition according to claim 14, wherein the second molecular probe detects a reference sequence.

16. The composition according to claim 15, wherein the reference sequence is a centromere sequence.

17. The composition according to claim 16, wherein the centromere sequence is selected from the group consisting of: CEP1, CEP2, CEP3, CEP4, CEP5, CEP6, CEP7, CEP8, CEP9, CEP10, CEP11, CEP12, CEP13, CEP14, CEP15, CEP16, CEP17, CEP18, CEP19, CEP20, CEP21, CEP22, CEP23, CEP X, and CEP Y.

18. The composition according to claim 14, wherein the first molecular probe and the second molecular probe detect sequences flanking or within one or more potential breakpoints.

19. The composition according to claim 14, further comprising a third molecular probe.

20. The composition according to claim 1, wherein the first molecular probe is a DNA probe, a PNA probe, or an LNA probe.

21. The composition according to claim 14, wherein the second molecular probe is a DNA probe, a PNA probe, or an LNA probe.

22. The composition according to claim 19, wherein the third molecular probe is a DNA probe, a PNA probe, or an LNA probe.

23. The composition according to claim 1, wherein the molecular probe further comprises a label.

24. The composition according to claim 23, wherein the label is a chromophore, fluorophore, biotin, DIG, antibody-hapten, dye, or enzyme.

25. The composition according claim 1, wherein the concentration of polar aprotic solvent in the composition ranges from 1% (v/v) to 95% (v/v).

26. The composition according to claim 1, wherein the concentration of polar aprotic solvent in the composition ranges from 5% (v/v) to 10% (v/v).

27. The composition according to claim 1, wherein the concentration of polar aprotic solvent in the composition ranges from 10% (v/v) to 20% (v/v).

28. The composition according to claim 1, wherein the concentration of polar aprotic solvent in the composition ranges from 20% (v/v) to 30% (v/v).

29. The composition according to claim 1, wherein the polar aprotic solvent is non-toxic.

30. The composition according to claim 1, with the proviso that the composition does not contain formamide.

31. The composition according to claim 1, wherein the polar aprotic solvent has a dispersion solubility parameter ranging from 17.7 MPa$^{1/2}$ to 22.0 MPa$^{1/2}$, a polar solubility parameter ranging from 13 MPa$^{1/2}$ to 23 MPa$^{1/2}$, and a hydrogen bonding solubility parameter ranging from 3 MPa$^{1/2}$ to 13 MPa$^{1/2}$.

32. The composition according to claim 1, wherein the polar aprotic solvent is selected from the group consisting of:

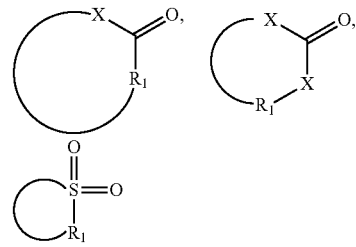

where X is O and R1 is alkyldiyl, and

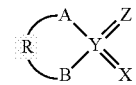

where X is optional and if present, is chosen from O or S,
where Z is optional and if present, is chosen from O or S,
where A and B independently are O or N or S or part of the alkyldiyl or a primary amine,
where R is alkyldiyl, and
wherein Y is O, S, or C, and wherein if Y is C, then either X or Z is not present.

33. The composition according to claim 1, wherein the polar aprotic solvent is selected from the group consisting of: 2,3-butylene carbonate, γ-butyrolactone, caprolactone (epsilon), chloro maleic anhydride, chloroethylene carbonate, citraconic anhydride, crotonlactone, 5-cyano-2-thiouracil, cyclopropylnitrile, dipheynyl sulfone, ethylene carbonate, ethylene glycol sulfite, 2-furonitrile, 4-methoxy benzonitrile, methyl alpha bromo tetronate, methyl phenyl sulfone, methyl sulfolane, methyl-4-toluenesulfonate, N-phenyl sydnone, phthalic anhydride, picolinonitrile (2-cyanopyridine), 1,3-propane sultone,β-propiolactone, propylene carbonate, saccharin, sulfanilamide, sulfolane, trimethylene sulfide-dioxide, and trimethylene sulfite.

34. The composition according claim 1, wherein the polar aprotic solvent is selected from the group consisting of:

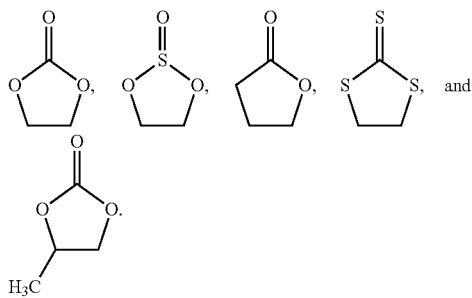

35. The composition according to claim 1, wherein the polar aprotic solvent is:

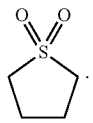

36. The composition according to claim 1, further comprising at least one additional component selected from the group consisting of: buffering agents, salts, accelerating agents, chelating agents, detergents, and blocking agents.

37. The composition according to claim 36, wherein the accelerating agent is dextran sulfate, the salt is sodium chloride, and/or the buffering agent is sodium phosphate.

38. The composition according to claim 37, wherein the dextran sulfate is present at a concentration of 5% to 40%, the sodium chloride is present at a concentration of 0 mM to 1200 mM, and/or the sodium phosphate is present at a concentration of 0 mM to 50 mM.

39. The composition according to claim 38, wherein the dextran sulfate is present at a concentration of 10% to 30%, the sodium chloride is present at a concentration of 300 mM to 1200 mM, and/or the sodium phosphate is present at a concentration of 5 mM to 20 mM.

40. The composition according to claim 36, wherein the buffering agent is citric acid buffer, and the accelerating agent is selected from the group consisting of: formamide, glycerol, propylene glycol, 1,2-propanediol, diethylene glycol, ethylene glycol, glycol, and 1,3 propanediol.

41. The composition according to claim 40, wherein:
the formamide is present at a concentration of 0.1-5%,
the glycerol, propylene glycol, 1,2-propanediol, diethylene glycol, ethylene glycol, glycol, or 1,3 propanediol is present at a concentration of 0.1% to 10%, and
the citric acid buffer is present at a concentration of 1 mM to 50 mM.

42. The composition according to claim 36, wherein the blocking agent is selected from the group consisting of: total human DNA, herring sperm DNA, salmon sperm DNA, and calf thymus DNA.

43. The composition according to claim 42, wherein the total human DNA, herring sperm DNA, salmon sperm DNA, or calf thymus DNA is present at a concentration of 0.01 to 10 μg/μL.

44. The composition according to claim 1, comprising 40% of the at least one polar aprotic solvent, 10% dextran sulfate, 300 mM sodium chloride, and 5 mM sodium phosphate.

45. The composition according to claim 1, comprising 15% of the at least one polar aprotic solvent, 20% dextran sulfate, 600 mM sodium chloride, 10 mM sodium phosphate, and 0.1 μg/μl total human DNA.

46. The composition according to claim 1, comprising:
15% of the at least one polar aprotic solvent,
20% dextran sulfate,
600 mM sodium chloride,
10 mM citric acid buffer pH 6.2,
0.1 μg/μL of herring sperm DNA, salmon sperm DNA, or calf thymus DNA, and
an accelerating agent selected from the group consisting of 0.5% formamide, 1% ethylene glycol, 1% 1,3 propanediol, and 1% glycerol.

47. The composition according claim 1, wherein the composition comprises more than one phase at room temperature.

48. A kit comprising the composition of claim 1.

49. A method of detecting a target in chromosomal DNA in a sample having a preserved cell morphology comprising
providing at least one molecular probe that hybridizes to the target in chromosomal DNA,
providing a sample having a preserved cell morphology comprising chromosomal DNA,
providing the composition of claim 1,
combining the molecular probe, the sample comprising chromosomal DNA, and the composition of claim 1 for at least a time period sufficient to hybridize the molecular probe to the target such that the cell morphology is preserved, and
detecting the target within the sample.

50. A method of determining the presence of a chromosomal aberration in a nucleic acid sequence within a sample having a preserved cell morphology, the method comprising:
providing at least one molecular probe,
providing a sample having a preserved cell morphology comprising a nucleic acid sequence,
providing the composition of claim 1,
combining the molecular probe, the sample comprising the nucleic acid sequence, and the composition of claim 1 for at least a time period sufficient to hybridize the molecular probe and the nucleic acid sequence such that the cell morphology is preserved,
detecting the at least one molecular probe within the sample,
and determining the presence of the chromosomal aberration.

51. A method of determining the presence of a chromosomal aberration in a nucleic acid sequence within a sample having a preserved cell morphology, the method comprising:
providing a sample having a preserved cell morphology comprising a nucleic acid sequence,
providing the composition of claim 1,
applying the composition of claim 1 to said sample comprising the nucleic acid for at least a time period sufficient to hybridize the molecular probe and nucleic acid sequence such that the cell morphology is preserved,
detecting the at least one molecular probe within the sample,
and determining the presence of the chromosomal aberration.

52. A method of determining the presence of a chromosomal aberration in a nucleic acid sequence within a sample having a preserved cell morphology, the method comprising:
    providing a sample having a preserved cell morphology comprising a nucleic acid sequence,
    applying a composition according to claim 1 to said sample comprising the nucleic acid sequence for at least a time period sufficient to hybridize the molecular probe and nucleic acid sequence such that the cell morphology is preserved, and
    determining whether the chromosomal aberration is present in the nucleic acid sequence within the sample.

\* \* \* \* \*